United States Patent
Dobrzanski et al.

(10) Patent No.: US 9,023,853 B2
(45) Date of Patent: May 5, 2015

(54) JANUS KINASE 2 (JAK2) INHIBITOR FOR THE TREATMENT OF LUPUS

(71) Applicant: Cephalon, Inc., Frazer, PA (US)

(72) Inventors: Pawel T. Dobrzanski, Downingtown, PA (US); Matthew M. Seavey, Secane, PA (US)

(73) Assignee: Cephalon, Inc., Frazer, PA (US)

( * ) Notice: Subject to any disclaimer, the term of this patent is extended or adjusted under 35 U.S.C. 154(b) by 160 days.

(21) Appl. No.: 13/911,447

(22) Filed: Jun. 6, 2013

(65) Prior Publication Data

US 2014/0024655 A1 Jan. 23, 2014

Related U.S. Application Data

(63) Continuation of application No. PCT/US2011/063427, filed on Dec. 6, 2011.

(60) Provisional application No. 61/420,053, filed on Dec. 6, 2010, provisional application No. 61/420,967, filed on Dec. 8, 2010.

(51) Int. Cl.
A61K 31/496 (2006.01)

(52) U.S. Cl.
CPC .................................... A61K 31/496 (2013.01)

(58) Field of Classification Search
CPC .................................................. A61K 31/496
See application file for complete search history.

(56) References Cited

PUBLICATIONS

Alperovich et al., "New immunosuppresor strategies in the treatment of murine lupus nephritis," *Lupus* (2007), vol. 16, pp. 18-24.
Aringer et al., "Tumour necrosis factor and other proinflammatory cytokines in systemic lupus erythematosus: a rationale for therapeutic intervention," *Lupus* (2004), vol. 13, pp. 344-347.
Bertsias et al., "Update on the management of lupus nephritis: let the treatment fit the patient," *Nature Clinical Practice Rheumatology* (2008), vol. 4, pp. 464-472.
Body et al., "Profiling the Safety and Tolerability of Bisphosphonates," *Seminars in Oncology* (2004), vol. 31, pp. 73-78.
Boumpas et al., "A Short Course of BG9588 (Anti-CD40 Ligand Antibody) Improves Serologic Activity and Decreases Hematuria in Patients with Proliferative Lupus Glomerulonephritis," *Arthritis & Rheumatism* (2003), vol. 48, pp. 719-727.
Bouzid et al., "C-telopeptides of type I collagen in postmenopausal women: An experience in a Tunisian Clinical Laboratory," *La Tunisie Medicate* (2010), vol. 88, pp. 467-469.
Chevrier et al., "CD93 is required for maintenance of antibody secretion and persistence of plasma cells in the bone marrow niche," *PNAS* (2009), vol. 106, pp. 3895-3900.
Chun et al., "Cytokine IL-6 and IL-10 as Biomarkers in Systemic Lupus Erythematosus," *J. Clin. Immunol.* (2007), vol. 27, pp. 461-466.
Coombs et al., "Improved pain, physical functioning and health status in patients with rheumatoid arthritis treated with CP-690,550, an orally active Janus kinase (JAK) inhibitor: results from a randomized, double-blind, placebo-controlled trial," *Ann. Rheum. Dis.* (2010), vol. 69, pp. 413-416.
Cunningham, "Pathogenesis and Prevention of Bone Loss in Patients Who Have Kidney Disease and Receive Long-Term Immunosuppression," *J. Am. Soc. Nephrol.* (2007), vol. 18, pp. 223-234.
Egner, "The use of laboratory tests in the diagnosis of SLE," *J. Clin. Pathol.* (2000), vol. 53, pp. 424-432.
Espeli et al., "Local Renal Autoantibody Production in Lupus Nephritis," *J. Am. Soc. Nephrol.* (2011), vol. 22, pp. 296-305.
Fairhurst et al., "Systemic Lupus Erythematosus: Multiple Immunological Phenotypes in a Complex Genetic Disease," *Advances in Immunology* (2006), vol. 92, pp. 1-69.
Fu et al., "Association of elevated transcript levels of interferon-inducible chemokines with disease activity and organ damage in systemic lupus erythematosus patients," *Arthritis Res. & Therapy* (2008), vol. 10, R112.
Houssiau et al., "Current treatment of lupus nephritis," *Lupus* (2008), vol. 17, pp. 426-430.
Kamen et al., "Skeletal manifestations of systemic autoimmune diseases," *Curr. Opin. Endocrinol. Diabetes Obes.* (2010), vol. 17, pp. 540-545.
Kiss et al., "Anti-nuscleosome antibody, a reliable indicator for lupus nephritis," *Autoimmunity* (2009), vol. 42, pp. 393-398.
Lacotte et al., "Idenification of New Pathogenic Players in Lupus: Autoantibody-Secreting Cells are Present in Nephritic Kidneys of (NZBxNZW)F1 Mice," *J. Immunology* (2010), vol. 184, pp. 3937-3945.
Meister et al., "Extensive Immunoglobulin Production Sensitizes Myeloma Cells for Proteasome Inhibition," *Cancer Res.* (2007), vol. 67, pp. 1783-1792.
Morel, "Genetics of SLE: evidence from mouse models," *Nat. Rev. Rheumatol.* (2010), vol. 6, pp. 348-357.
Morimoto et al., "The Increased Interleukin-13 in Patients with Systemic Lupus Erythematosus: Relations to Other Th1-, Th2-Related Cytokines and Clinical Findings," *Autoimmunity* (2001), vol. 34, pp. 19-25.
Muller et al., "Pathogenic anti-nucleosome antibodies," *Lupus* (2008), vol. 17, pp. 431-436.

(Continued)

*Primary Examiner* — Renee Claytor

(57) ABSTRACT

The present invention provides a method for treating lupus in a subject, comprising the step of administering to the subject COMPOUND A.

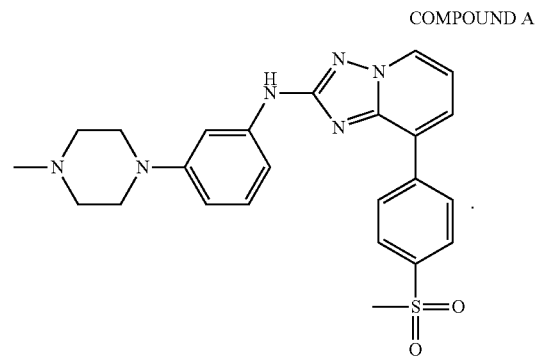

COMPOUND A

17 Claims, 50 Drawing Sheets

(56) References Cited

PUBLICATIONS

Neubert et al., "The proteasome inhibitor bortezomib depletes plasma cells and protects mice with lupus-like disease from nephritis," *Nature Medicine* (2008), vol. 14, pp. 748-755.

Niewold et al., "High serum IFN-α activity is a heritable risk factor for systemic lupus erythematosus," *Genes and Immunity* (2007), vol. 8, pp. 492-502.

Obeng et al., "Proteasome inhibitors induce a terminal unfolded protein response in multiple myeloma cells," *Blood* (2008), vol. 107, pp. 4907-4916.

Sanz et al., "B cells as therapeutic targets in SLE," *Nat. Rev. Rheumatol.* (2010), vol. 6, pp. 326-337.

Smith et al., A female preponderance for chemically induced lupus in SJL/J mice, *Clin. Immun.* (2007), vol. 122, pp. 101-107.

Smith-Bouvier et al., "A role for sex chromosome complement in the female bias in autoimmune disease," *J. Exp. Med.* (2008), vol. 205, pp. 1099-1108.

Sozzani et al., "Type I interferons in systemic autoimmunity," *Autoimmunity* (2010), vol. 43, pp. 196-203.

Tucci et al., "Overexpression of interleukin-12 and T helper 1 predominance in lupus nephritis," *Clin. & Exp. Immunology* (2008), vol. 154, pp. 247-254.

Fig. 1

COMPOUND A in MRL/lpr lupus model 8 wks old

| Randomize cages | Treatments 8-11 weeks of age | Stop Treatment Check ANAs | Treatments 18-21 weeks of age | Stop Check Urine |
|---|---|---|---|---|
| Age: 8wks | Age: 11wks | | Age: 18wks | Age: 21wks |
| Initial Body weight, & Bleeds | 1x weekly bleeds (serum) + Urine collection, body weight | Serum+Urine/2 weeks | 1x weekly bleeds (serum) + Urine collection, body weight | Stop PD/PK |

Groups
1. MRL/lpr + COMPOUND A-high (12)
2. MRL/lpr + COMPOUND A-med (12)
3. MRL/lpr + COMPOUND A-low (12)
4. MRL/lpr + DEX (12)
5. MRL/lpr + Vehicle (12)

Treatments
1. COMPOUND A = 100mg/kg, b.i.d., p.o.
2. COMPOUND A = 55mg/kg, b.i.d., p.o.
3. COMPOUND A = 30mg/kg, b.i.d., p.o.
4. DEX = Dexamethasone = 1.5mg/kg/2d (M,W,F), i.p.
5. Vehicle = PEG400, bid, p.o.

Read-outs:
- DURING: ANA antibodies (Sm, dsDNA, Chromatin)
- DURING: Urine protein – Assay and sticks
- END: Serum cytokines (Luminex)
- END: PK – Blood/Spleen/Kidney; PD – Spleen/Kidney
- END: Spleen T+B cell Elispots (T: Sm, Chromatin), (B: dsDNA, Sm, Chromatin)
- END: Spleen FACS (Plasma cells, B cells)
- END: Kidney pathology – fixed and frozen Fig. 4
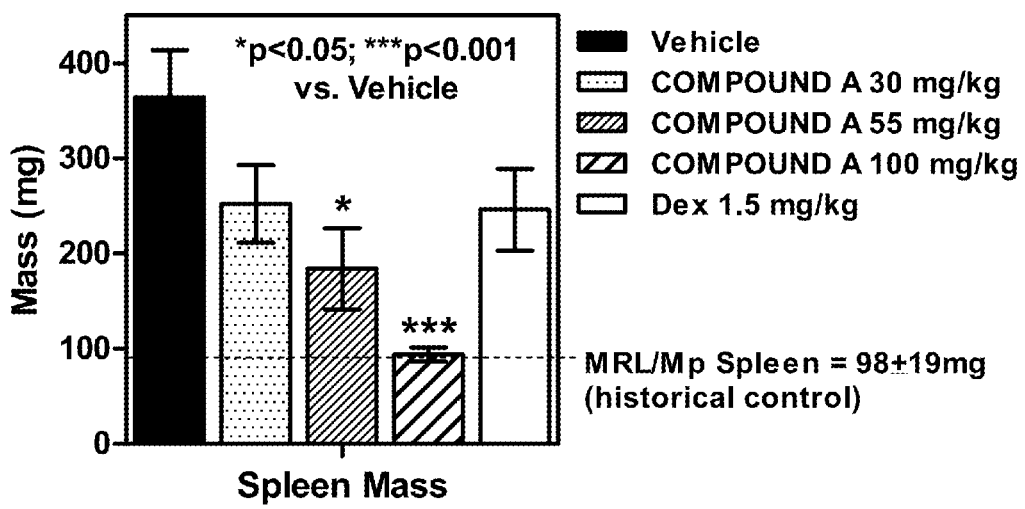
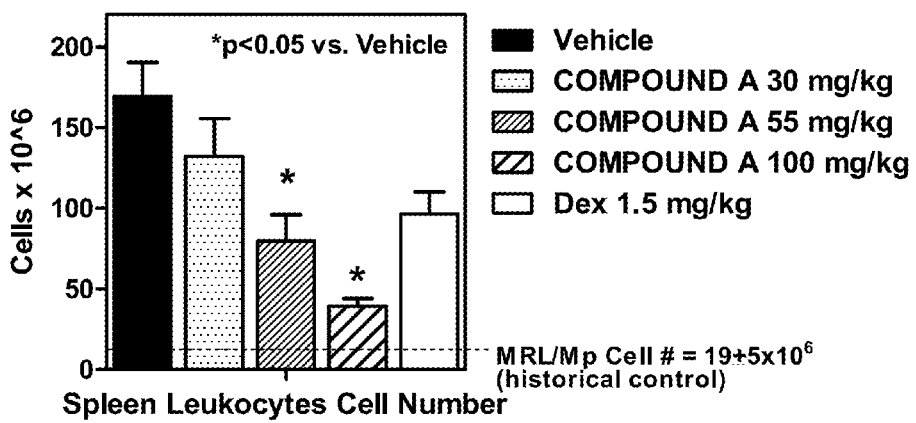

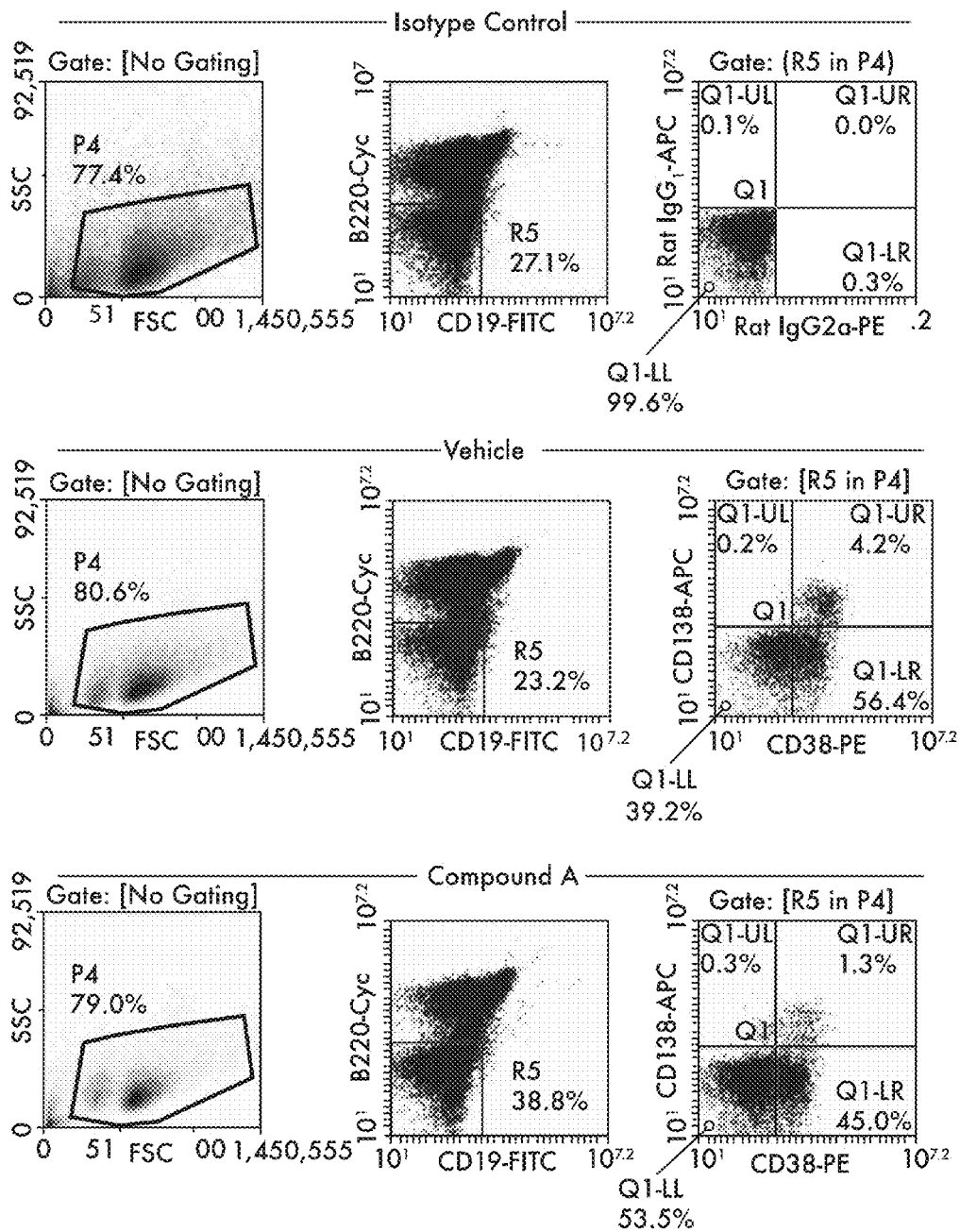

COMPOUND A in NZBWF1 (NZM) Lupus Experiment

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

*Outliers for CTX group excluded from analysis and graphing as values exceeded 2.5x greater than the standard deviation for the group

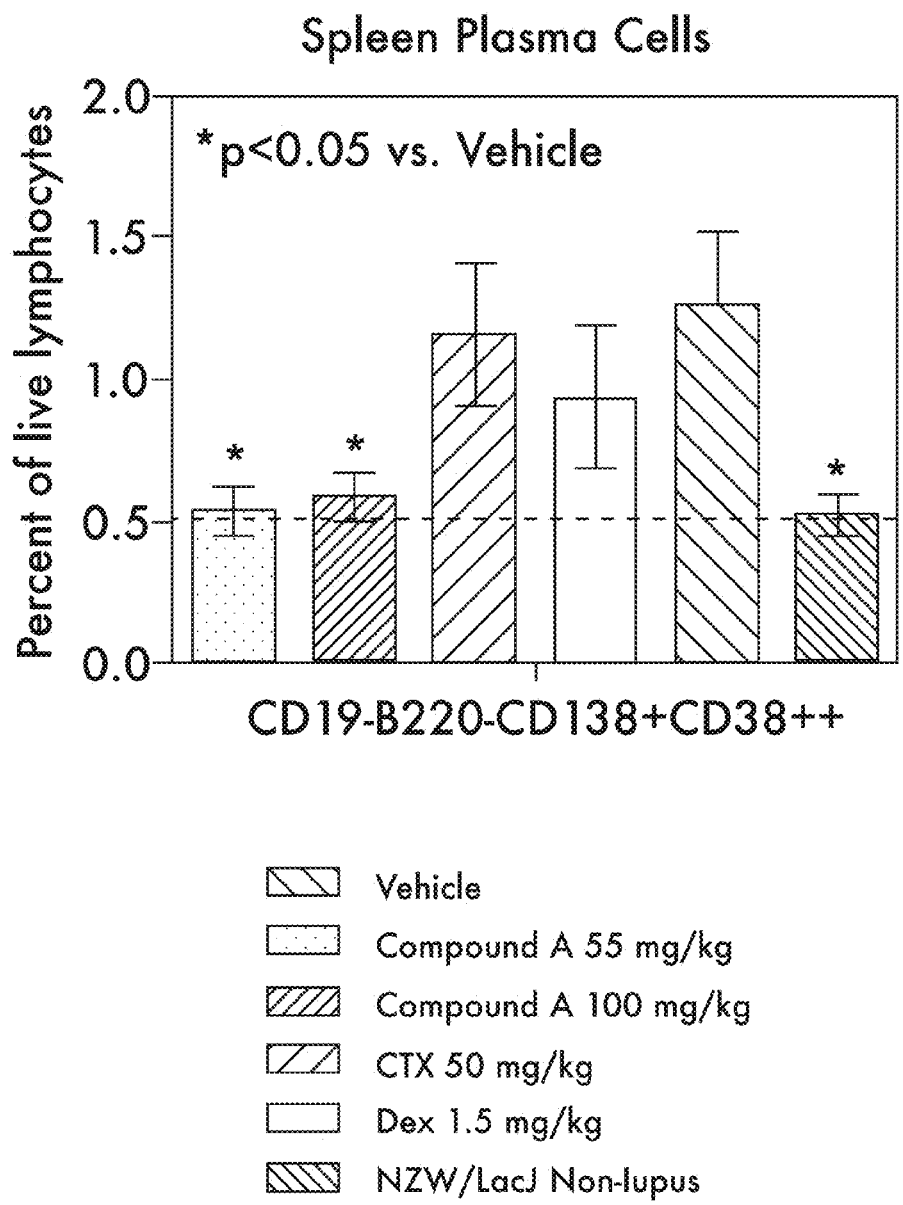

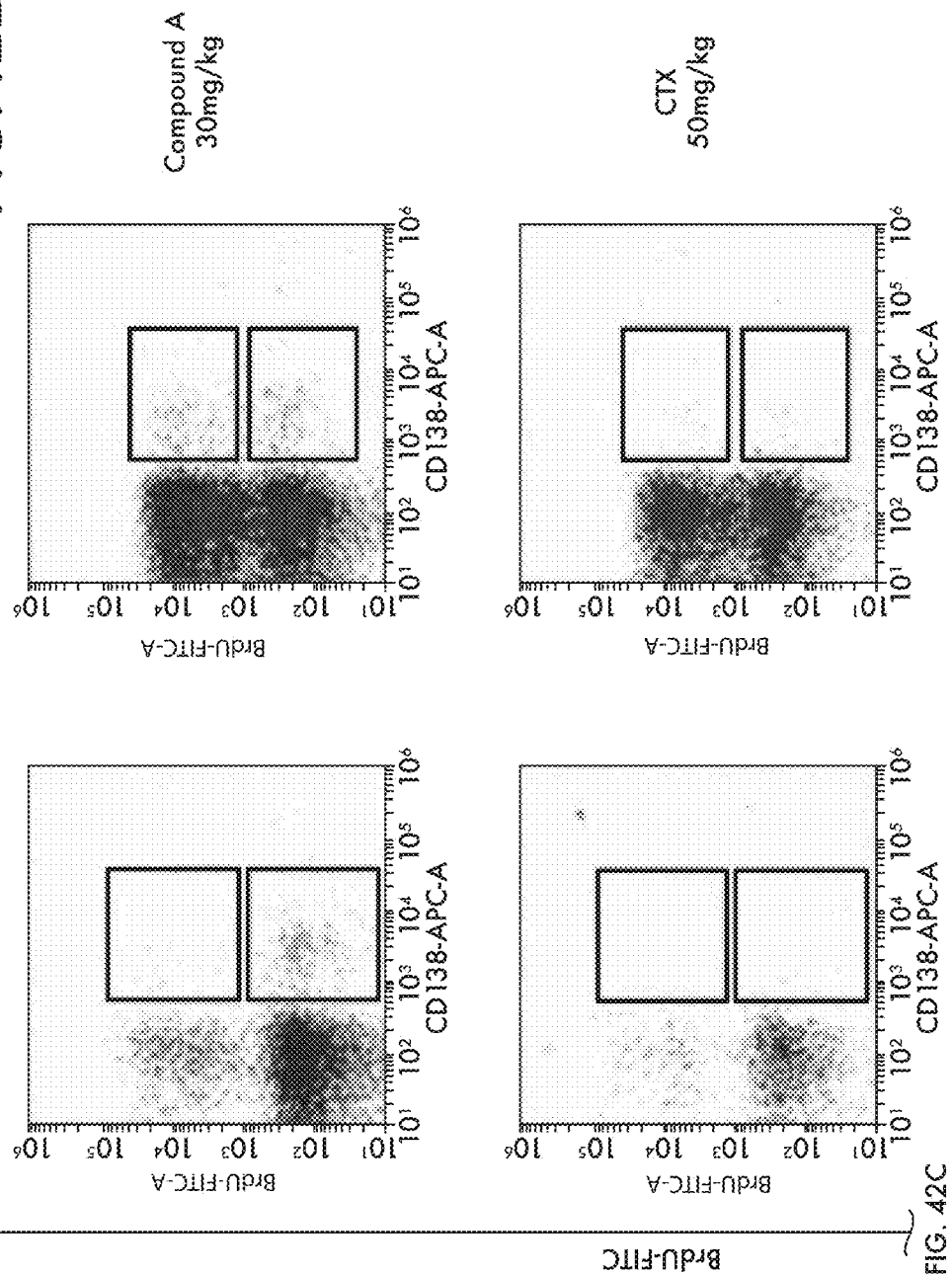

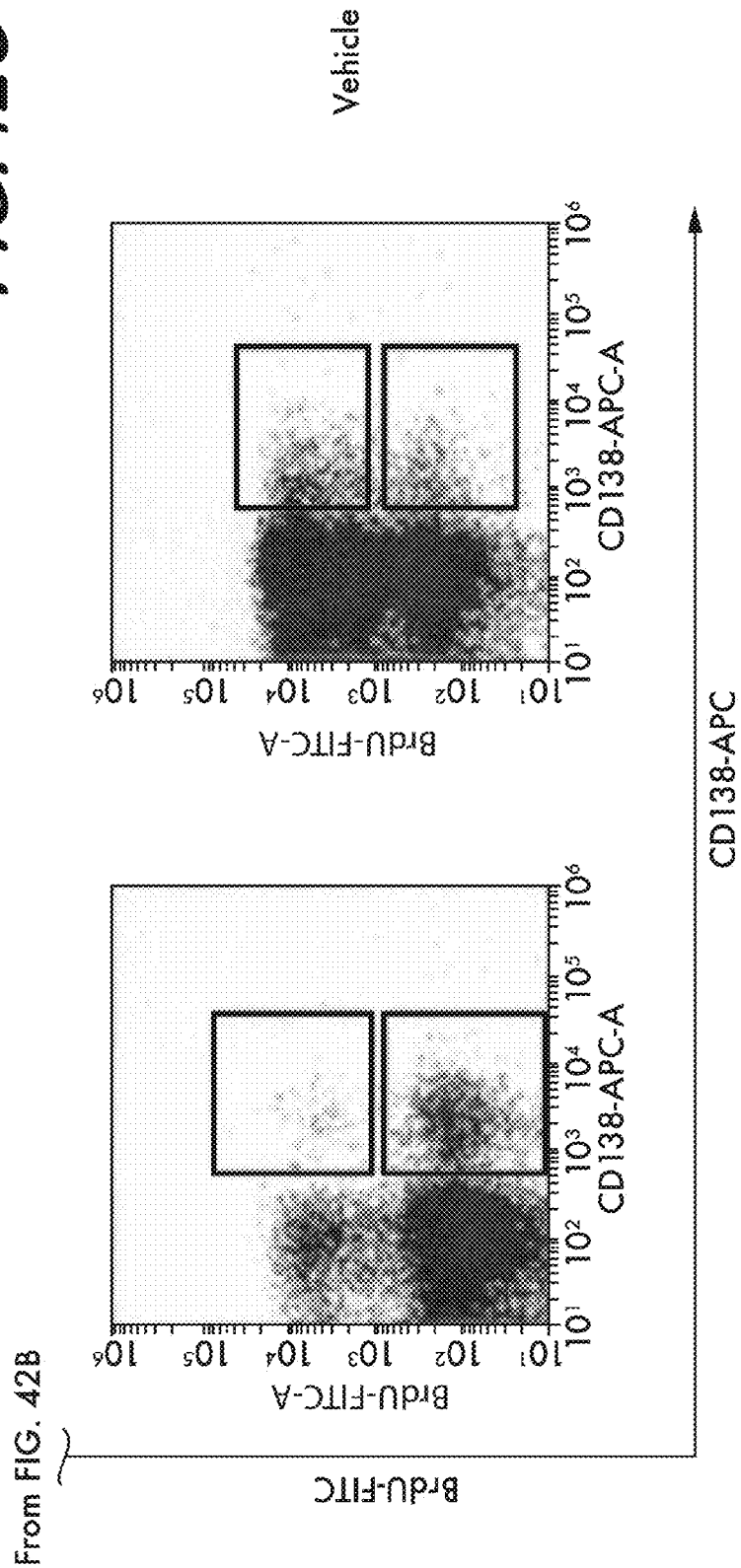

JANUS KINASE 2 (JAK2) INHIBITOR FOR THE TREATMENT OF LUPUS

CROSS REFERENCE TO RELATED APPLICATIONS

This application is a continuation of International Application No. PCT/US2011/063427, filed Dec. 6, 2011, which claims the benefit of U.S. Provisional Application Nos. 61/420,053, filed Dec. 6, 2010 and 61/420,967, filed Dec. 8, 2010, the disclosures of which are incorporated herein by reference in their entireties.

TECHNICAL FIELD

Lupus therapy.

BACKGROUND

Lupus (systemic lupus erythematosus, SLE) is a chronic autoimmune disease characterized by the presence of activated T and B cells, autoantibodies and chronic inflammation that attacks various parts of the body including the joints, skin, kidneys, CNS, cardiac tissue and blood vessels. In severe cases, antibodies are deposited in the cells (glomeruli) of the kidneys, leading to inflammation and possibly kidney failure, a condition known as lupus nephritis.

Although the cause of lupus remains unknown, manifestations of the disease have been linked to genetic polymorphisms, environmental toxins and pathogens (Morel; Fairhurst, Wandstrat et al. 2006). In addition, gender, hormonal influences and cytokine dysregulation have been tightly linked to the development of lupus (Aringer and Smolen 2004; Smith-Bouvier, Divekar et al. 2008). Lupus affects nine times as many women as men. It may occur at any age, but appears most often in people between the ages of 10 and 50 years. African Americans and Asians are affected more often than people from other races.

There is no cure for lupus. Current treatments for lupus are aimed at controlling symptoms and are limited to toxic and immunosuppressive agents with severe side-effects such as high dose glucocorticoids and/or hydroxchloroquine. Severe disease (e.g., patients that have signs of renal involvement) require more aggressive drugs including mycophenolate mofetil (MMF), azathioprine (AZA) and/or cyclophosphamide (CTX) (Bertsias and Boumpas 2008). CTX, AZA and MMF are very toxic and immunosuppressive, and only 50% of treated patients enter complete remission, with relapse rates up to 30% over a 2-year period.

Memory B cells, and more important, long-lived plasma cells (LL-PCs) which differentiate from memory B cells, are key cell types involved in lupus (Neubert, Meister et al. 2008; Sanz and Lee 2010). Long-lived plasma cells synthesize and secrete large quantities of high-affinity isotype switched antibodies (Meister, Schubert et al. 2007; Muller, Dieker et al. 2008). Circulating antinuclear antibodies (ANAs) increase the chances of antibody depositing onto self tissues, forming immune-complexes and eventually leading to tissue destruction, epitope spreading and involvement of other organ systems. LL-PCs are commonly found to be chemo- and radio-resistant, over expressing various heat shock proteins and drug pumps (Obeng, Carlson et al. 2006; Neubert, Meister et al. 2008). In addition, LL-PCs primarily reside in the bone marrow where they are protected from current lupus therapies such as cyclophosphamide and glucocorticoids.

A need exists for new treatments for lupus, including lupus nephritis. A need particularly exists for lupus treatments that can target and reduce LL-PCs.

SUMMARY

Provided are methods for treating lupus in a subject with COMPOUND A. In one embodiment, the subject is a human. In one embodiment, the COMPOUND A is administered orally. In one embodiment, the COMPOUND A is administered once per day. In one embodiment, the COMPOUND A is administered twice per day. In one embodiment, the COMPOUND A is administered as a prodrug.

In one embodiment, the COMPOUND A is administered at a dose in the range of about 1 mg/kg to about 100 mg/kg. In one embodiment, the COMPOUND A is administered at a dose of about 50 mg/kg to about 100 mg/kg. In one embodiment, the COMPOUND A is administered at a dose of about 50 mg/kg. In one embodiment, the COMPOUND A is administered at a dose of about 1 mg to about 1 g. In one embodiment, the COMPOUND A is administered at a dose of about 5 mg to about 100 mg. In one embodiment, the COMPOUND A is administered at a dose of about 5 mg to about 20 mg.

In one embodiment, the subject experiences a decrease in serum IL-12 during treatment. In one embodiment, the subject experiences a decrease in kidney pSTAT3 during treatment. In one embodiment, the subject experiences a decrease in spleen plasma cells during treatment. In one embodiment, the subject experiences a decrease in serum antinuclear antibodies during treatment. In one embodiment, the subject experiences a decrease in serum IFNα during treatment. In one embodiment, the subject experiences a decrease in proteinuria during treatment.

BRIEF DESCRIPTION OF THE DRAWINGS

FIG. 1 depicts an overview of how COMPOUND A was tested in the acute lupus MRL/lpr mouse model.

FIG. 4 depicts the reduction in spleen size and total spleen leukocyte cell number in MRL/lpr mice treated with various doses of COMPOUND A.

FIGS. 10A-10B depict the reduction in the percent of plasma cells after treatment with 100 mg/kg COMPOUND A in MRL/lpr mice.

FIGS. 35A-35B depict the proportion of CD19/B220- CD38+ CD138+ spleen plasma cells in NZM mice treated with COMPOUND A, top portion shows graphed percent data, below portion provides a representative raw dot plot image from flow cytometry.

FIGS. 42A-42C depict representative flow cytometry dot plots of live gate, CD19-negative, CD38-positive, spleen and bone marrow plasma cells from NZM mice treated with COMPOUND A and gated according to the markers on the X and Y axis.

DETAILED DESCRIPTION OF ILLUSTRATIVE EMBODIMENTS

Figure 2:
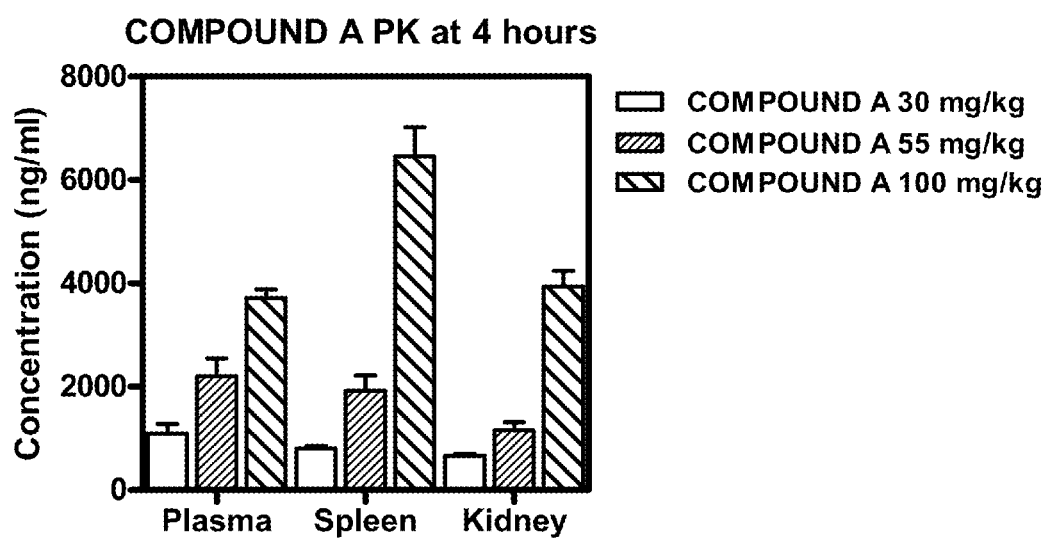
FIG. 2 depicts the levels of COMPOUND A in various tissues 4 hours post po administration at various doses in the MRL/lpr mouse.

The term "about" as used herein when referring to a measurable value such as an amount, a temporal duration, and the like, is meant to encompass reasonable variations of the value, such as, for example, ±10% from the specified value. For example, the phrase "about 50%" can include ±10% of 50, or from 45% to 55%.

As used herein, the term "subject" includes warm blooded animals, preferably mammals, including humans. In a preferred embodiment, the subject is a primate. In an even more preferred embodiment, the subject is a human.

Provided are methods for treating lupus in a subject using COMPOUND A. COMPOUND A is a JAK2 inhibitor with the chemical name [8-(4-methanesulfonyl-phenyl)-[1,2,4]triazolo[1,5-a]pyridin-2-yl]-[3-(4-methyl-piperazin-1-yl)-phenyl]-amine. COMPOUND A has the following structure:

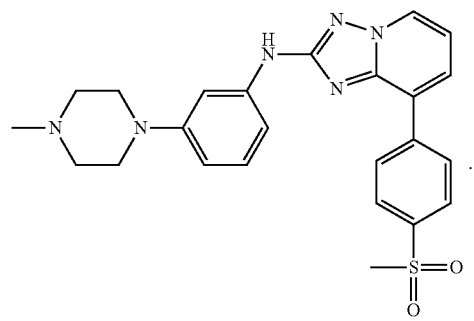 [SMILES: CN1CCN(c2cccc(Nc3nc4c(-c5ccc(S(C)(=O)=O)cc5)cccn4n3)c2)CC1]

The COMPOUND A used in the present invention may be administered in any suitable chemical form, including as a prodrug. Suitable prodrugs include pharmaceutically acceptable salt forms of the parent compound. Preferably, the prodrug converts to the parent compound (i.e., COMPOUND A) after administration. As used herein, "pharmaceutically acceptable salt" refers to a derivative of the parent compound in which the compound is modified by making an acid or base salt thereof. Examples of pharmaceutically acceptable salts include, but are not limited to, mineral or organic acid salts of basic amine residues.

Therefore, in one embodiment the COMPOUND A is administered as a salt derivative of the parent compound. In one embodiment, the COMPOUND A is administered as an acid salt of COMPOUND A.

Any suitable method of administration may be used. Examples include injection (subcutaneous, intravenous, parenterally, intraperitoneally, intrathecal, etc.), oral, rectal, transmucosal, inhalation, and transdermal. When administered by injection, the injection can be bolus or continuous infusion.

COMPOUND A is preferably administered by IV injection or by oral dosage form, such as in a tablet or capsule. For example, the COMPOUND A may be provided as a sterile lyophilized powder, which may be reconstituted with, e.g., sterile Water for Injection, aqueous saline (NaCl), or aqueous mannitol before injection. Therefore, in one embodiment the COMPOUND A is administered by intravenous (IV) injection. In another embodiment, the COMPOUND A is administered orally. In one embodiment, the COMPOUND A is administered orally in a tablet. In another embodiment, the COMPOUND A is administered orally in a capsule.

For oral administration, COMPOUND A may be formulated readily by combining COMPOUND A with pharmaceutically acceptable carriers well known to those in the art. Such carriers enable the COMPOUND A to be formulated as tablets, pills, dragees, capsules, liquids, gels, syrups, slurries, suspensions, emulsions, and the like, for oral ingestion by a subject to be treated. Pharmaceutical preparations for oral use can be obtained by combining COMPOUND A with a solid excipient, optionally grinding the resulting mixture, and processing the mixture of granules, after adding suitable auxiliaries, if desired, to obtain tablets or dragee cores. Suitable excipients include fillers or diluents, binders, disintegrants, lubricants, antiadherents, glidants, wetting and surface active agents, colors and pigments, flavoring agents, sweeteners, adsorbents, and taste-maskers.

Diluents are typically added to a small amount of the active drug to increase the size of the tablet. The most common diluent is lactose, which exists in two isomeric forms, alpha-lactose or beta-lactose, and can be either crystalline or amorphous. Various types of lactose include spray dried lactose monohydrate (such as Super-Tab™), alpha-lactose monohydrate (such as Fast Flo®), anhydrous alpha-lactose, anhydrous beta-lactose, and agglomerated lactose. Other diluents include sugars, such as compressible sugar NF, dextrose excipient NF, and dextrates NF. A preferred diluent is lactose monohydrate (such as Fast Flo®)). Other preferred diluents include microcrystalline cellulose (such as Avicel® PH, and Ceolus™), and microtine cellulose (such as Elcema®).

Diluents may include starch and starch derivatives. Starches include native starches obtained from wheat, corn, rice and potatoes. Other starches include pregelatinized starch NF, and sodium starch glycolate NF. Starches and starch derivatives also function as disintegrants. Other diluents include inorganic salts, such as dibasic calcium phosphate USP (such as Di-Tab® and Emcompress®), tribasic calcium phosphate NF (such as Tri-Tab® and Tri-Cafos®), and calcium sulfate NF (such as Compactrol®). Such polyols as mannitol USP, sorbitol NF, and xylitol NF may also serve as diluents. Many diluents also function as disintegrants and binders, and these additional properties must be taken into account when developing a formulation.

Disintegrants are included in tablet formulations to break the tablets into particles of the active pharmaceutical ingredient and excipients which will facilitate dissolution of the active ingredient and enhance bioavailability of the active ingredient. Starch and starch derivatives, including cross-linked sodium salt of a carboxymethyl ether of starch (such as sodium starch glycolate NF, Explotab®, and Primogel®) are useful disintegrants. A preferred disintegrant is pregelatinized starch, such as Starch 1500®. Another preferred disintegrant is cross-linked sodium carboxymethyl cellulose (such as Croscarmellose Sodium NF, Ac-Di-Sol®). Other disintegrants include cross-linked polyvinylpyrrolidone (such as Crospovidone NF), microcrystalline cellulose (such as Avicel® PH).

Binders are used as a wet granulation excipient to agglomerate the active pharmaceutical ingredient and the other excipients. A binder is selected to improve powder flow and to improve compactibility. Binders include cellulose derivatives such as microcrystalline cellulose NF, methylcellulose USP, carboxymethycellulose sodium USP, hydroxypropyl methylcellulose USP, hydroxyethyl cellulose NF, and hydroxypropyl cellulose NF. Other binders include polyvidone, polyvinyl pyrrolidone, gelatin NF, natural gums (such as acacia, tragacanth, guar, and pectin), starch paste, pregelatinized starch NF, sucrose NF, corn syrup, polyethylene glycols, and sodium alginate, ammonium calcium alginate, magnesium aluminum silicate, polyethylene glycols. A preferred binder is polyvinyl pyrrolidone, in particular, Povidone USP, and preferably, povidone K-29/32.

Lubricants are used in tablet formulation to prevent sticking of the tablet to the punch faces and to reduce friction during the compression stages. Lubricants typically include vegetable oils (such as corn oil), mineral oils, polyethylene glycols (such as PEG-4000 and PEG-6000), salts of stearic acid (such as calcium stearate and sodium stearyl fumarate), mineral salts (such as talc), inorganic salts (such as sodium chloride), organic salts (such as sodium benzoate, sodium acetate, and sodium oleate) and polyvinyl alcohols. A preferred lubricant is magnesium stearate.

Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the COMPOUND A in admixture with filler such as lactose, binders such as starches, and/or lubricants such as talc or magnesium stearate and, optionally, stabilizers. In soft capsules, the COMPOUND A may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the COMPOUND A is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The COMPOUND A may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the COMPOUND A in water-soluble form. Additionally, suspensions of the COMPOUND A may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the COMPOUND A to allow for the preparation of highly concentrated solutions.

The COMPOUND A may be in powder form for constitution with a suitable vehicle, e.g., sterile pyrogen-free water, before use.

The COMPOUND A may also be formulated in rectal compositions such as suppositories or retention enemas, e.g., containing conventional suppository bases such as cocoa butter or other glycerides.

In addition to the formulations described previously, the COMPOUND A may also be formulated as a depot preparation. Such long acting formulations may be administered by implantation (for example subcutaneously or intramuscularly) or by intramuscular injection. Thus, for example, the COMPOUND A may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the COMPOUND A may be delivered using a sustained-release system, such as semipermeable matrices of solid hydrophobic polymers containing the therapeutic agent. Various forms of sustained-release materials have been established and are well known by those skilled in the art. Sustained-release capsules may, depending on their chemical nature, release the COMPOUND A for a few hours up to over 100 days.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

The COMPOUND A is administered in an amount effective to treat lupus, i.e., an amount effective to prevent, alleviate, or ameliorate symptoms of the disease, prolong survival of the subject being treated, and/or favorably impact lupus-related biomarkers in the subject. Determination of the effective amount of COMPOUND A is well within the capability of those skilled in the art in light of the detailed disclosure and examples provided herein. The effective amount can vary depending on such factors as the size of the subject, the severity of the lupus disease, the frequency of administration (e.g., once daily vs. multiple times per day), the manner of administration of the compound, the health and co-morbid conditions of the subject, the judgment and experience of the prescribing physician (e.g., with the same or similar drugs), the mode of administration, the bioavailability characteristics of the dosage form administered, the dose regimen selected, and the kind of concurrent treatment (e.g., glucocorticoids). For example, the effective amount of COMPOUND A for monotherapy may be a higher dose than the amount of COMPOUND A that is effective when COMPOUND A is used together in combination with other lupus therapies. Effective doses can be extrapolated from dose-response curves derived from in vitro or animal model test systems, and may be based on the surface area or weight of the subject.

Treatment can be initiated with smaller dosages which are less than the optimum dose of the compound. Thereafter, the dosage can be increased by small increments until the optimum effect under the circumstances is reached. The total daily dosage may be divided and administered in portions during the day if desired. To optimize the dosing regimen, the effectiveness of COMPOUND A can be monitored by monitoring the effect of treatment on various biomarkers in a subject undergoing treatment. Useful biomarkers include those listed in the Examples section herein (e.g., antinuclear antibodies, cytokines such as IFNα and IL-12, proteinuria, JAK2 inhibition, etc.). Two especially convenient biomarkers for monitoring the effectiveness of lupus treatment are proteinuria and antinuclear antibodies. An effective dose of COMPOUND A will alter the biomarker(s) in the desired way as compared to the biomarker level prior to treatment (e.g., decrease proteinuria, decrease antinuclear antibodies, decrease pSTAT3, etc.). Thus, an effective dose of COMPOUND A can be optimized by starting at a low dose, and then titrating up whilst monitoring one or more of these biomarkers. In general, it is preferable to obtain the initial assessment of the biomarker(s) (e.g., proteinuria or antinuclear antibodies) from the patient prior to beginning therapy and one or more additional assessments at different time points during treatment. In such a use, a baseline determination prior to therapy is determined and then changes in biomarker(s) (e.g., proteinuria or antinuclear antibodies) are determined during the course of therapy. Alternatively, two or more successive determinations can be made during treatment without the need of a pre-treatment baseline measurement. In such a use, the first assessment of biomarker(s) (e.g., proteinuria or antinuclear antibodies) should be made from the subject as a baseline level for determining whether the level is increasing or decreasing.

In preferred embodiments, the subject undergoing treatment with COMPOUND A experiences a desirable change in one or more biomarkers associated with lupus disease. Suitable biomarkers associated with lupus include lymphomegaly, splenomegaly, spleen leucocyte counts, serum IL-12, serum C3, kidney glomerular cellularity, kidney interstitial infiltration, kidney pSTAT3, spleen plasma cells, serum antinuclear antibodies, serum anti-dsDNA antinuclear antibodies, serum IFNα, proteinuria, lung infiltrates, serum IL-17A, serum IL-6, serum CCL3/MIP-1α, serum CXCL10/IP-10, serum CXCL9/MIG, serum IL-4, serum IL-13, serum TNFα, serum KC/IL-8, and serum CTx. Therefore, in one embodiment the subject experiences a decrease in lymphomegaly during treatment with COMPOUND A. In another embodiment, the subject experiences a decrease in splenomegaly during treatment with COMPOUND A. In another embodiment, the subject experiences a decrease in spleen leucocyte counts during treatment with COMPOUND A. In another embodiment, the subject experiences a decrease in serum IL-12 during treatment with COMPOUND A. In another embodiment, the subject experiences an increase in serum C3 during treatment with COMPOUND A. In another embodiment, the subject experiences a decrease in kidney glomerular cellularity during treatment with COMPOUND A. In another embodiment, the subject experiences a decrease in kidney interstitial infiltration during treatment with COMPOUND A. In another embodiment, the subject experiences a decrease in kidney pSTAT3 during treatment with COMPOUND A. In another embodiment, the subject experiences a decrease in spleen plasma cells during treatment with COMPOUND A. In another embodiment, the subject experiences a decrease in serum antinuclear antibodies during treatment with COMPOUND A. In another embodiment, the subject experiences a decrease in serum anti-dsDNA antinuclear antibodies during treatment with COMPOUND A. In another embodiment, the subject experiences a decrease in serum IFNα during treatment with COMPOUND A. In another embodiment, the subject experiences a decrease in proteinuria during treatment with COMPOUND A. In another embodiment, the subject experiences a decrease in lung infiltrates during treatment with COMPOUND A. In another embodiment, the subject experiences a decrease in serum IL-17A during treatment with COMPOUND A. In another embodiment, the subject experiences a decrease in serum IL-6 during treatment with COMPOUND A. In another embodiment, the subject experiences a decrease in serum CCL3/MIP-1α during treatment with COMPOUND A. In another embodiment, the subject experiences a decrease in serum CXCL10/IP-10 during treatment with COMPOUND A. In another embodiment, the subject experiences a decrease in serum CXCL9/MIG during treatment with COMPOUND A. In another embodiment, the subject experiences a decrease in serum IL-4 during treatment with COMPOUND A. In another embodiment, the subject experiences a decrease in serum IL-13 during treatment with COMPOUND A. In another embodiment, the subject experiences a decrease in serum TNFα during treatment with COMPOUND A. In another embodiment, the subject experiences a decrease in serum KC/IL-8 during treatment with COMPOUND A. In another embodiment, the subject experiences a decrease in serum CTx during treatment with COMPOUND A.

The regimen of administration of the COMPOUND A can vary depending on such factors as the pharmacokinetics of the dosage form, the type of lupus symptoms being treated or inhibited, the size of the subject, the severity of the lupus disease, and the effective dosage. The timing of administration of the COMPOUND A can be readily varied by the treating physician to optimize efficacy and minimize side effects in light of the above considerations and the present detailed disclosure.

There is wide flexibility in the dosing schedules for COMPOUND A according to present invention. In certain embodiments, the dosing schedules can be adapted from dosing schedules known to be suitable for other JAK inhibitors. For example, the JAK inhibitors tasocitinib (CP-690550) and INCB028050 were shown to be effective in rheumatoid arthritis at doses of 5-30 mg twice per day, or 4-10 mg once daily, respectively (Coombs, J. H. et al. 2010; www.medpagetoday.com/MeetingCoverage/ACR/23308). Even though the prior art JAK inhibitors were used to treat rheumatoid arthritis and not lupus, comparison is possible because effective JAK inhibition is responsible for treatment both diseases.

The COMPOUND A may be administered at any suitable dose. In one embodiment, the COMPOUND A is administered at a dose of about 0.01 mg/kg to about 1 g/kg of body weight. In another embodiment, the COMPOUND A is administered at a dose of about 0.1 mg/kg to about 200 mg/kg of body weight. In another embodiment, the COMPOUND A is administered at a dose of about 1 mg/kg to about 500 mg/kg of body weight. In another embodiment, the COMPOUND A is administered at a dose of about 1 mg/kg to about 100 mg/kg of body weight. In another embodiment, the COMPOUND A is administered at a dose of about 10 mg/kg to about 200 mg/kg of body weight. In another embodiment, the COMPOUND A is administered at a dose of about 10 mg/kg to about 100 mg/kg of body weight. In another embodiment, the COMPOUND A is administered at a dose of about 25 mg/kg to about 150 mg/kg of body weight. In another embodiment, the COMPOUND A is administered at a dose of about 50 mg/kg to about 100 mg/kg of body weight. In another embodiment, the COMPOUND A is administered at a dose of about 55 mg/kg to about 100 mg/kg of body weight. In another embodiment, the COMPOUND A is administered at a dose of about 1 mg/kg of body weight. In another embodiment, the COMPOUND A is administered at a dose of about 5 mg/kg of body weight. In another embodiment, the COMPOUND A is administered at a dose of about 10 mg/kg of body weight. In another embodiment, the COMPOUND A is administered at a dose of about 50 mg/kg of body weight. In another embodiment, the COMPOUND A is administered at a dose of about 100 mg/kg of body weight. In another embodiment, the COMPOUND A is administered at a dose of about 0.1 mg to about 1 g. In another embodiment, the COMPOUND A is administered at a dose of about 0.5 mg to about 500 mg. In another embodiment, the COMPOUND A is administered at a dose of about 1 mg to about 100 mg. In another embodiment, the COMPOUND A is administered at a dose of about 5 mg to about 50 mg. In another embodiment, the COMPOUND A is administered at a dose of about 5 mg to about 30 mg. In another embodiment, the COMPOUND A is administered at a dose of about 5 mg to about 20 mg. In another embodiment, the COMPOUND A is administered at a dose of about 1 mg. In another embodiment, the COMPOUND A is administered at a dose of about 5 mg. In another embodiment, the COMPOUND A is administered at a dose of about 10 mg. In another embodiment, the COMPOUND A is administered at a dose of about 20 mg. In another embodiment, the COMPOUND A is administered at a dose of about 30 mg. In another embodiment, the COMPOUND A is administered at a dose of about 40 mg. In another embodiment, the COMPOUND A is administered at a dose of about 50 mg. In another embodiment, the COMPOUND A is administered at a dose of about 100 mg. In another embodiment, the COMPOUND A is administered at a dose of about 200 mg. The preceding doses are suitable for any method of COMPOUND A administration, and are especially suitable for oral dosing.

The COMPOUND A may be administered at the above-described doses according to any suitable schedule. The COMPOUND A dose amounts may be constant or varied within the dosing schedule. The COMPOUND A dose may be maintained at a constant level during the schedule unless (a) desired biomarker(s) changes are not observed, in which case subsequent doses can be increased, or (b) significant drug-related toxicity is observed, in which case subsequent doses can be reduced, for example by about 20-30% in each case. A suitable COMPOUND A schedule will typically range from once-monthly dosing to multiple-daily dosing. In a preferred embodiment, the COMPOUND A is administered once-daily.

In another embodiment, the COMPOUND A is administered once weekly. In another embodiment, the COMPOUND A is administered twice daily. In another embodiment, the COMPOUND A is administered three times per day. In another embodiment, the COMPOUND A is administered four times per day.

One or more additional lupus treatments can be used in combination with the administration of the COMPOUND A. Such treatments include lupus agents including, but not limited to, glucocorticoids, hydroxchloroquine, mycophenolate mofetil (MMF), azathioprine (AZA), and cyclophosphamide (CTX). Appropriate doses of these agents are well known in the art.

Materials and Methods

Animals

Six week old lupus-prone, female, MRL/lpr (Jackson Labs, #000485) and non-lupus prone control MRL/MpJ (Jackson Labs, #000486) mice were obtained from Jackson Laboratories (Bar Harbor, Me.) at 6-weeks of age. Spontaneous SLE-prone NZBWF1/J (NZM) (catalog no. 100008) female mice and non-lupus prone (within time from of experiment) NZW/LacJ (catalog no. 001058) female mice were obtained from Jackson Laboratories (Bar Harbor, Me.) at 15-weeks of age. All mice were maintained on a 24 hour light/dark cycle, with food and water available ad libitum. All experimental animal procedures were approved by and in accordance to the regulations of the Institutional Animal Care and Use Committee (IACUC) of Cephalon, Inc; approved IACUC protocol #03-040 and #03-03-041.

MRL/lpr mice develop a rapid lymphoproliferative disease due an inactive Fas molecule preventing the proper apoptosis of self-reactive T and B cells in primary and secondary lymphoid tissues (deficiency in both central and peripheral tolerance mechanism). Due to this impaired tolerance mechanism, a percentage of all T and B cells that enter the periphery have a high likelihood of responding to self protein/tissues and thus initiate autoimmunity early in life. The MRL/lpr model mice develop several chronic inflammatory disease-like symptoms that are characteristic of early and late lupus including the generation of anti-nuclear antibodies, arthritis, dermatological manifestations, immunocomplex-mediated glomerulonephritis leading to proteinuria and eventual death. Lesser characterized phenomenon are CNS and cardiac manifestations, both of which are more common in humans. Previous optimization and validation studies clearly showed that disease only manifests in diseased MRL/lpr animals and not the control mice, MRL/Mp, and that antinuclear antibodies (ANAs) rapidly form between weeks 4-12 leading to the onset of lupus nephritis around weeks 18-25 with the presence of proteinuria. Mortality is higher in the females and occurs around 25 weeks of age, renal disease includes glomerulonephritis, glomerular infiltrates, sclerosis and vasculitis. Both splenomegaly and lymphomegaly associated with dermatitis can also be observed.

The NZM strain acts as a mouse model of genetically-driven, progressive, systemic lupus erythematosus (SLE). The evolution of the disease in NZM mice is characterized by an abnormal polyclonal B cell activation with a high production of various autoantibodies, including those directed against DNA and other nuclear antigens, and against cytoskeleton proteins. Elevated circulating immune complexes can lead to fatal glomerulonephritis in older mice.

Compound A

COMPOUND A was prepared in a manner analogous to the five-step method described below (see Example 35 of International Application No. PCT/US10/37363):

Step 1: To a solution of 1-(3-bromo-phenyl)-piperazine (about 1 g) and acetic acid (about 0.4 mL) in methanol (about 25 mL) is added 37% formaldehyde in water/methanol (about 56.7:37:6.3, water:formaldehyde:methanol; about 5 mL). The mixture is stirred at room temperature for about 18 hours. The suspension is cooled to about 5° C. in an ice/water bath and sodium cyanoborohydride (about 5 g) is added in small portions. The mixture is stirred and warmed to room temperature for about 18 hours. The mixture is slowly poured into saturated aqueous ammonium chloride (about 200 mL) and stirred for about 1 hour. The mixture is extracted with dichloromethane (3× about 75 mL). The combined organic layers are dried over magnesium sulfate, filtered and evaporated. The material is placed under high vacuum for about 18 hours to yield 1-(3-bromo-phenyl)-4-methyl-piperazine as a pale yellow oil (about 1 g). $^1$H NMR (400 MHz, CDCl$_3$, δ, ppm): 7.10 (dd, J=8.2, 8.2 Hz, 1H), 7.04 (dd, J=2.1, 2.1 Hz, 1H), 6.95 (ddd, J=7.8, 1.7, 0.7 Hz, 1H), 6.83 (ddd, J=8.3, 2.4, 0.6 Hz, 1H), 3.23-3.18 (m, 4H), 2.58-2.54 (m, 4H), 2.35 (s, 3H). MS=255, 257 (MH)+.

Step 2: To a solution of 3-bromo-pyridin-2-ylamine (about 10 g) in 1,4-dioxane (about 100 mL) is added dropwise ethoxycarbonyl isothiocyanate (about 7 mL). The mixture is stirred under an atmosphere of nitrogen for about 18 hours. The volatiles are evaporated to yield a waxy solid. The recovered material is triturated with hexane (about 250 mL). N-(3-bromo-2-pyridinyl)-N'-carboethoxy-thiourea is isolated and used without further purification. $^1$H NMR (400 MHz, (D$_3$C)$_2$SO, δ, ppm): 11.46 (s, 1H), 11.43 (s, 1H), 8.49 (dd, J=4.6, 1.5 Hz, 1H), 8.18 (dd, J=8.0, 1.5 Hz, 1H), 7.33 (dd, J=8.0, 4.7 Hz, 1H), 4.23 (q, J=7.1 Hz, 2H), 1.27 (t, J=7.2 Hz, 3H). MS=215 (MH)+.

Step 3: To a stirred suspension of hydroxylamine hydrochloride (about 17 g) and N,N-diisopropylethylamine (about 26 mL) in a mixture of methanol (about 70 mL) and ethanol (about 70 mL) is added N-(3-bromo-2-pyridinyl)-N'-carboethoxy-thiourea. The mixture is stirred for about 2 hours at room temperature then heated to about 60° C. for about 18 hours. The suspension is cooled to room temperature, filtered and rinsed with methanol, water then methanol. 8-Bromo-[1,2,4]triazolo[1,5-a]pyridin-2-ylamine is isolated as an off-white solid (about 8 g). $^1$H NMR (400 MHz, (D$_3$C)$_2$SO, δ, ppm): 8.58 (d, J=6.4 Hz, 1H), 7.73 (d, J=7.6 Hz, 1H), 6.80 (t, J=7.0 Hz, 1H), 6.25 (s, 2H). MS=213, 215 (MH)+.

Step 4: An oven dried tube is charged with palladium acetate (about 0.2 g) and triphenylphosphine (about 0.6 g). The tube is evacuated under high vacuum and backflushed under a stream of nitrogen for about 5 minutes. A suitable solvent such as 1,4-dioxane (about 10 mL) is added and the mixture is stirred under nitrogen for a suitable time (e.g., for about 10 minutes). 8-Bromo-[1,2,4]triazolo[1,5-a]pyridin-2-ylamine (about 0.75 g), (4-methylsulfonylphenyl)boronic acid (about 1 g), a suitable solvent, such as N,N-dimethylformamide (about 10 mL) and a suitable base, such as about 1.5 M of sodium carbonate in water (about 10 mL) are added. The mixture is stirred for about 2 minutes at room temperature under nitrogen then the tube is sealed and heated at about 80° C. for about 18 hours. The mixture is transferred to a round bottom flask and the volatiles are evaporated under reduced pressure. The product is isolated in a suitable manner. For example, water (about 100 mL) may be added and the mixture stirred. The solid may then be collected by filtration, and optionally rinsed with water, air dried, triturated with ether/dichloromethane (about 4:1; about 10 mL), filtered and rinsed with ether. 8-(4-methanesulfonyl-phenyl)-[1,2,4]triazolo[1,5-a]pyridin-2-ylamine is isolated as a tan solid (about 0.6 g). MP=236-239° C. $^1$H NMR (400 MHz, (D$_3$C)$_2$SO, δ, ppm):

8.63 (d, J=6.3 Hz, 1H), 8.38 (d, J=7.9 Hz, 2H), 8.03 (d, J=7.9 Hz, 2H), 7.84 (d, J=7.3 Hz, 1H), 7.03 (t, J=7.0 Hz, 1H), 6.21 (br s, 2H), 3.28 (s, 3H). MS=289 (MH)+.

Step 5: To an oven dried tube is added palladium acetate (about 10 mg) and 2,2'-bis-dicyclohexylphosphanyl-biphenyl (about 30 mg), 8-(4-methanesulfonyl-phenyl)-[1,2,4]triazolo[1,5-a]pyridin-2-ylamine (about 75 mg), 1-(3-bromophenyl)-4-methyl-piperazine (about 80 mg), a suitable base, such as cesium carbonate (about 270 mg) and a suitable solvent, such as 1,4-dioxane (about 5 mL). The tube is evacuated and backflushed with nitrogen three times. The tube is sealed and heated at about 80° C. for about 72 hours. The mixture is cooled to room temperature and the product isolated in a suitable manner. For example, the cooled mixture may be diluted with dichloromethane (about 10 mL), filtered through a plug of diatomaceous earth, rinsed with dichloromethane and evaporated. The material may then be purified, e.g., via chromatography, e.g., utilizing an ISCO automated purification apparatus (e.g., amine modified silica gel column 5%→100% ethyl acetate in hexanes). [8-(4-Methanesulfonyl-phenyl)-[1,2,4]triazolo[1,5-a]pyridin-2-yl]-[3-(4-methyl-piperazin-1-yl)-phenyl]-amine (i.e., COMPOUND A) is isolated as a yellow solid (about 0.07 g). MP=232-234° C. $^1$H NMR (400 MHz, CDCl$_3$, δ, ppm): 8.49 (d, J=7.2 Hz, 1H), 8.25 (d, J=7.5 Hz, 2H), 8.08 (d, J=7.9 Hz, 2H), 7.65 (d, J=7.7 Hz, 1H), 7.38 (s, 1H), 7.27-7.20 (m, 1H), 7.04-6.95 (m, 2H), 6.84 (s, 1H), 6.60 (d, J=8.0 Hz, 1H), 3.30-3.25 (m, 4H), 3.10 (s, 3H), 2.63-2.58 (m, 4H), 2.38 (s, 3H). MS=463 (MH)+.

Flow Cytometry

Antibodies used for flow cytometry consisted of anti-mouse CD138-APC (eBioscience, San Diego, Calif.), anti-mouse CD19-FITC (eBioscience, San Diego, Calif.), anti-mouse CD38-PE (eBioscience, San Diego, Calif.) and anti-mouse CD45R/B220-Cyc (eBioscience, San Diego, Calif.), Rat IgG$_1$-APC isotype control (eBioscience, San Diego, Calif.), Rat IgG$_{2a}$-PE isotype control (eBioscience, San Diego, Calif.). All samples were analyzed using an Accuri C6 Flow Cytometer. Complete media was used for all experiments involving the ex vivo culture of splenocytes for all Elispot experiments. Complete media consisted of RPMI1640 (Cellgro, Manassas, Va.), plus 1% Pen-Strep (Cellgro, Manassas, Va.), 1% L-Gln (Cellgro, Manassas, Va.), 1% NEAA (Cellgro, Manassas, Va.), β-ME (Cellgro, Manassas, Va.), plus 10% FBS (Cellgro, Manassas, Va.).

Washed, RBC-lysed splenocytes were stained for plasma cell markers as previously used in published reports (Neubert, Meister et al. 2008). As used herein the term "plasma cell" will refer to the following immunophenotype definition: Plasma cells were defined as live CD19-negative, CD45R/B220-negative, CD138-positive, CD38-positive events for the MRL/lpr model. A total of 200,000-500,000 events were collected per tube/sample. Insufficient sample limited plasma cell determination in bone marrow. Flow staining protocol was as follows, briefly, cells were suspended in complete medium (defined above) and 2.5 μg of anti-CD16/CD32 (FcBlock) with anti-CD19-FITC, anti-CD38-PE, anti-CD45R/B220-Cyc and anti-CD138-APC antibodies. After 20 minutes of staining on ice, samples were washed then fixed. All samples were replicated with appropriate, matched isotypes as described below.

Luminex Analysis of Serum Cytokine Samples

For the processing of serum samples for cytokine analysis, frozen plasma at −80° C. was thawed on ice, vortexed, and centrifuged for 10 minutes to remove debris and aggregates. A total of 25-50 μL of serum was used for Luminex® assays following the manufacturer's instructions. Ten different mouse cytokines were measured using the mouse cytokine 10-plex bead kit (Invitrogen, Carlsbad, Calif., no. LMC0001). Briefly, filter plates (Millipore, Billerica, Mass., no. MAIPSWU10), were pre-wet with 200 μL of wash solution (kit component) and 25 μL of beads were added per well. Serum samples were diluted and a total volume of 50 μL was added per well (ie, 25 μL of sample serum plus 25 μL of assay diluent as provided by the manufacturer). Plates with beads were incubated for 2 hours at room temperature (RT) on an orbital shaker in the dark. At the end of the incubation, plate(s) were washed twice in kit buffer, secondary biotinylated antibody was added at a 1:10 dilution (100 μL) in biotin diluent provided with the kit. Plates were incubated at RT for 1 hour in the dark then washed twice in kit buffer. Strepavidin in assay diluent was added at 100 μL per well, then incubated for 30 minutes at RT in the dark. The plates were washed 3 times then 100 μL of kit wash solution was added and agitated for 2-3 minutes at RT in the dark. Plates were run immediately following this incubation period on a Luminex xMAP 200 unit with data acquisition and analysis software (Invitrogen, San Diego, Calif., no. MAP0200). All bead washing was performed using a vacuum manifold unit (Pall, Ann Arbor, Mich. no. 5017). For all cytokine Luminex assays, values below the limit of detection set by the lowest point along the standard or set by the manufacturer were considered out of range and were not estimated, but assumed the lowest point along the standard curve for that particular assay.

Urinalysis

Urine samples were acid precipitated for total protein recovery and analysis. Samples for which enough urine remained were used for Uristix® leukouria analysis (MRL/lpr study only). Briefly, a standard protein solution was prepared from normal mouse sera and was used as a standard for mouse urinary protein assay by turbidity. Standard preparation was as follows: 0, 5, 10, 15, 20, 30, 40, and 50 μL of a 4 mg/mL mouse sera standard protein solution as provided in the kit were added in duplicate into two columns. PBS was added to individual wells to adjust the final volume to 50 μL. For urine sample preparation, urine samples were centrifuged at 9880×g for 3 minutes using a tabletop micro-centrifuge. Urine supernatant (1-50 μL) was added in duplicate. PBS was added to adjust the volume to 50 μL total. For the turbidity assay: 25 μL of 0.1 N HCl was added into blank columns and 250 μL of 3% sulfosalicyclic acid into the test columns. The microplate was incubated for 10 minutes at RT and plates were read using an ELISA reader with single beam at 450 nm. For the Uristix® strip assay, strips were laid out and labeled. Twenty microliters of urine were placed onto each test strip square and incubated for at least 30 seconds before the result was recorded. For all total urine analysis plate-based assays, values below the limit of detection set by the lowest point along the standard or set by the manufacturer were considered out of range and were not estimated, but assumed the lowest point along the standard curve for that particular assay.

Histology

Figure 8:
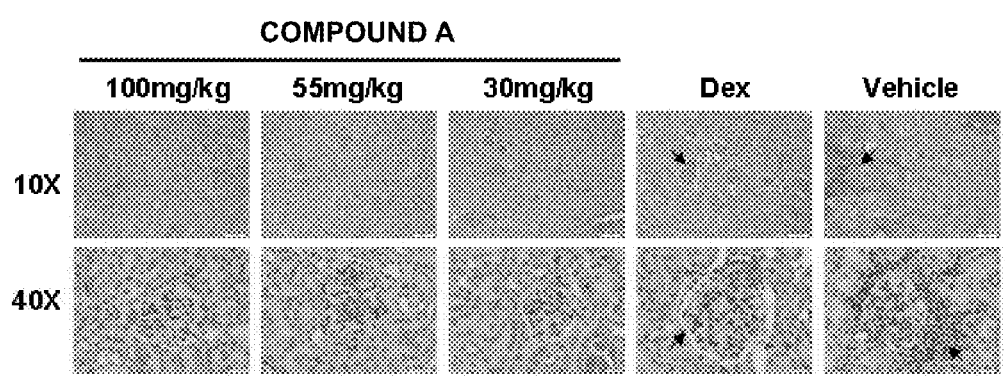
FIG. 8 depicts renal sections stained for leukocyte infiltration into the glomerulus in MRL/lpr mice. Greater glomerulonephritis is observed in the vehicle treated animals versus all three COMPOUND A treated animals at EOS. Black arrows show enlarged glomeruli and leukocytic infiltrations in both the dex and vehicle treated animals but absent from COMPOUND A treated animals.
Figure 19:
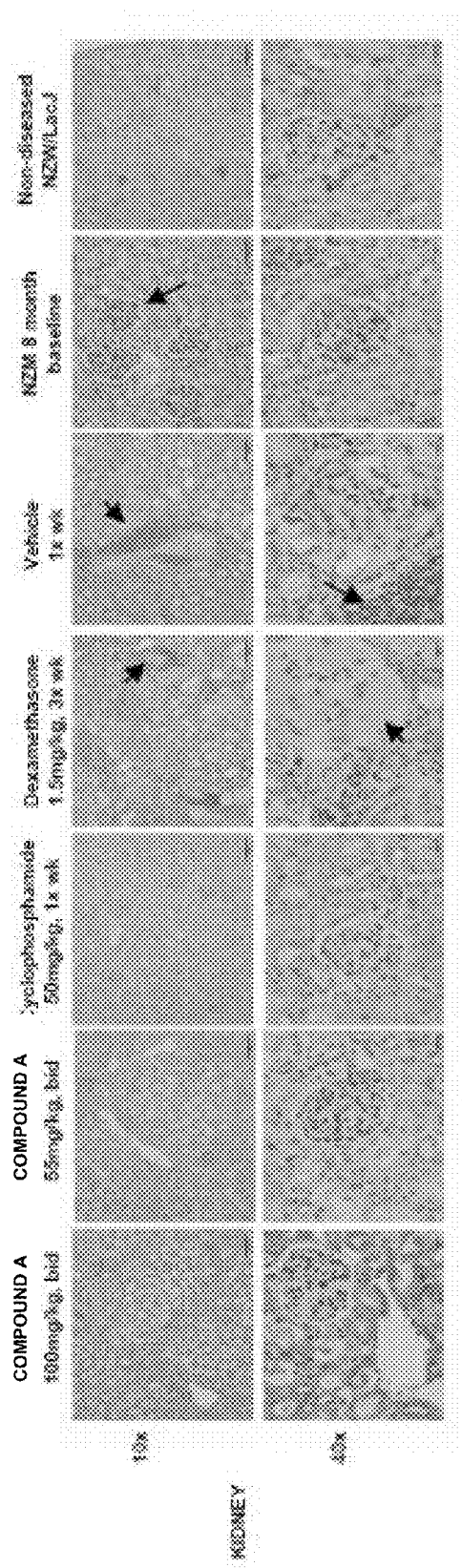
FIG. 19 depicts the renal histopathology of stained sections from NZM mice treated with various controls and COMPOUND A. The black arrows point to enlarged glomeruli and leukocytic infiltrates, which are absent in mice treated with COMPOUND A.
Figure 20:
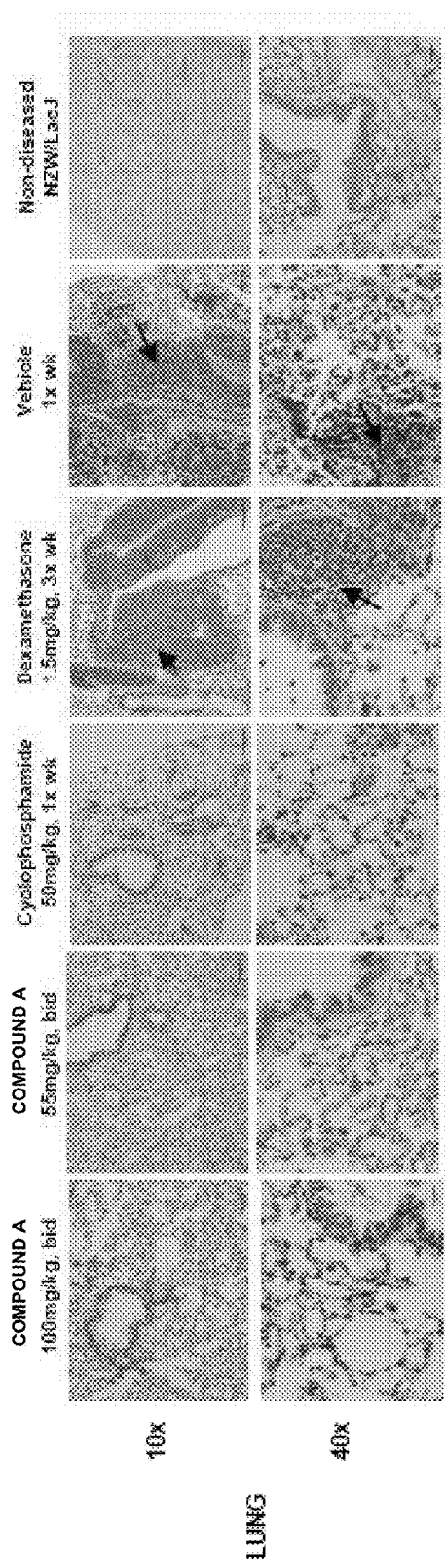
FIG. 20 depicts lung histopathology of stained sections from NZM mice treated with COMPOUND A. The black arrows point to adenomas, vasculitis and severe pulmonary inflammation associated with lupus. All three of these disease manifestations are missing in the CTX and COMPOUND A treated animals.

For histological analyses, the left kidney and lung (NZM model only) from each animal was removed and fixed in 10% buffered neutral 10% formalin (EMD) for 48 hours on an orbital rocker at 25° C., then washed overnight with running dH$_2$O and stored in 70% ethanol at 4° C. until ready to be processed. Kidney stains used for histological analyses included hematoxylin and eosin (H&E), Periodic Acid Schiff (PAS) and Trichrome stains (Wistar Institute, Philadelphia, Pa.). All 3 stained sections were used by the pathologist for scoring purposes. All histological scoring was performed blinded and by an independent board certified veterinary medical pathologist (Julie Engiles, VMD, DACVP; University of Pennsylvania). Multiple stains were used to determine score values. Images in FIGS. 8, 19 and 20 show worst affected area of section selected blindly by the pathologist.

Kidney IC-GN Scoring Method (Smith, Dong et al. 2007):
1. Glomerular cellularity—Score 1-5: Null, low, moderate, high, severe
2. Glomerular necrosis—Score 1-5: Null, low, moderate, high, severe
3. Glomerulosclerosis—Score 1-5: Null, low, moderate, high, severe
4. Interstitial infiltration—Score 1-5: Null, low, moderate, high, severe
5. Tubular atrophy—Score 1-5: Null, low, moderate, high, severe
6. Interstitial fibrosis—Score 1-5: Null, low, moderate, high, severe
7. Vasculitis—Score 1-5: Null, low, moderate, high, severe Specific Pathologist Definitions:
Necrosis was defined by the presence of nuclear debris/pyknosis within the glomerular tuft indicative of "necrosis." In many samples, this was a very mild, rare finding within only a very few segments of the glomerular tuft. Also considered effacement of the glomerular tuft by PAS positive, Trichrome negative material necrosis.
Glomerular sclerosis was defined by increased fibroplasia or fibrosis within the glomerular tuft or capsule. Sometimes glomerular sclerosis is considered an "end-stage" glomerular change, but here it is classified as those demonstrating "active" progressive fibrosis as glomerular "sclerosis."
Tubular atrophy was classified by increased luminal diameter and/or flattening of renal tubular epithelium, or drop-out of tubules.
Interstitial infiltration was considered as inflammatory infiltrates.
Vasculitis—A more loose definition of vasculitis to take into account non-inflammatory (degenerative/proliferative) vascular pathology. Most of the vascular changes were mild and could be considered "arteriosclerosis" characterized by proliferation of the smooth muscle cells, and hyalinization of the extracellular matrix. This change may reflect hypertension secondary to glomerular pathology. In very few animals was there overt "vasculitis." Most inflammatory changes were within the walls of the blood vessels, with little to no damage to the endothelium, and no overt hemorrhage/fibrin leakage. Many also have perivascular rims of fibroblasts.

Pharmacodynamic (PD) Analysis

Spleen and kidney were collected on day 118 (NZM model) or day 98 (MRL/lpr model) three hours post final dose administration and snap frozen on dry ice with cooled isopentene and stored at −80° C. Lysed spleen and kidney were processed using the following protocol. Seven hundred microliters "tissue extraction buffer" generated by combining protease inhibitor cocktail (Calbiochem, no. 539136) and Halt phosphatase inhibitor cocktail (Thermo scientific, no. 78420) or Roche phosphatase inhibitor cocktail (Roche, no. 04906837001) in tissue extraction reagent I (Invitrogen, no. FNN0071) were added to each sample. Samples were homogenized frozen using a PT 10-35 Polytron homogenizer (VWR, no. 97036-082). After homogenization the sample was centrifuged at 4° C. for 2000×g for 10 minutes, supernatant was re-centrifuged at 4° C. at maximum speed, 14,000×g, for 15 minutes. Supernatants were carefully removed to avoid picking up the top layer of lipids/adipose debris. Protein concentration was adjusted to 3 mg/ml using a BCA protein assay (Pierce, no. 83228). Spleen JAK/STAT (pSTAT1/3/5a/b) activity was analyzed using Luminex® 3-plex bead kit (Invitrogen). Both assays were performed per manufacture's instructions.

Pharmacokinetic (PK) Analysis

Plasma, kidney and spleen samples were submitted for quantitative analysis to determine compound concentrations. Blood samples were collected into heparinized tubes and placed on wet ice until centrifuged (16,000×g, 5 minutes) to separate the plasma. Supernatant was collected and stored at −20° C. pending analysis. At the time of analysis, two volumes of cold acetonitrile containing an internal standard (alprenolol) was added to each sample which was then vortexed and centrifuged. The supernatant was removed, placed into an auto-sampler vial and the amount of compound present in the samples was analyzed by liquid chromatograph/mass spectrometry (LC-MS-MS). The concentration of compound in the samples was quantified against a vehicle only (i.e., vehicle control group either spleen or kidney from vehicle group of that tested strain) standard curve (tissue specific) made via serial dilution in a concentration range from 5 to 20000 ng/mL. Samples containing concentrations greater than 10% above the top of the standard curve were diluted 1:10 with acetonitrile. The limit of detection for plasma, kidney and spleen was <10 ng/mL.

Antinuclear Antibody (ANA) ELISA Assays

The measurement of anti-dsDNA and anti-Smith antigen antibodies was done by an in-house generated custom ELISA assay. Chromatin coated plates were purchased from Inova Diagnostics, Inc. Purified bovine thymus dsDNA (Sigma, St. Louis, Mich.) or purified bovine Smith antigen (GenWay, San Diego, Calif.) were used as coating antigen for the detection of anti-dsDNA and anti-Smith Ag antibodies respectively. Coated plates were washed with Borate Sulfate Saline (BSS) and blocked with BSS containing 1% Bovine Serum Albumin (BSA) and 0.1% Tween-20 detergent. Standard curves were generated using mouse anti-chromatin antibody (Sigma, 2B1) or 25 week old MRL/lpr serum. Mouse anti-dsDNA antibody (Abcam, Cambridge, Mass.), or mouse anti-Smith antigen antibody (Abcam) were used as standards for each assay. Secondary antibody was purchased from Abcam (goat anti-mouse pAb-HRP), the substrate was purchased from Rockland (Gilbertsville, Pa.) (TMB), and stop reaction buffer was generated using 1 mL of concentrated sulfuric acid into 20 mL of $dH_2O$. Developed plates were read using a Victor-X4 spectrophotometer reading at 450 nM with a reference wavelength of 570 nM. For all ANA ELISA assays, values below the limit of detection set by the lowest point along the standard or set by the manufacturer were considered out of range and were not estimated, but assumed the lowest point along the standard curve for that particular assay.

Antibody Secreting B-Cell Elispot Assays

B-cell Elispot components were ordered from MabTech (Nacka Strand, Sweden) and nitrocellulose IP filter plates were ordered from Millipore (Billerica, Mass.). Elispot wells were coated with either purified bovine thymus dsDNA (Sigma), purified bovine Smith antigen (GenWay) or boiled filtered purified chicken chromatin from lysed chicken red blood cells (Rockland, Gilbertsville, Pa.) at 10 µg/mL. Spleens were processed using glass homogenization, filtered through a 60 µm sterile cell strainer and red blood cells (RBCs) lysed using BioLegend (San Diego, Calif.) lysis buffer. Processed splenocytes were added to each well in culture medium. To avoid skewing of true ex vivo frequencies of antibody secreting cell types (ASCs), cells were not stimulated with a polyclonal mitogen like LPS, but rather incubated in media alone to allow monitoring of genuine ex vivo antibody release. Anti-mouse pan-IgG was used as a positive control for total IgG producing ASCs and was used to normalize results. Frequencies for each antigen were identified in an initial test phase for each model. For chromatin and total IgG only, 30,000 splenocytes were added to each well; for Smith antigen and dsDNA, 500,000 cells were added to each well. Different numbers of splenocytes were added for different antigens due to saturation limits of spot frequencies per well. These limits were previously established. B-cell Elispots were incubated overnight at 37° C. To develop each assay, secondary antibody was added to each well, incubated, washed and alkaline phosphatase strepavidin was used as the conjugate; substrate used was BCIP-NBT. Plates were developed until spots were visible. All Elispot analyses were performed using an Immunospot C.T.L. scanner and Biospot software (Cellular Technology Ltd., Shaker Heights, Ohio). Results are shown as values from which media and cells only wells were subtracted.

Statistical Analysis

All statistics were performed using Graph Pad Prism 5.0 software. End-of-study analyses were analyzed using either two-tailed Mann-Whitney or paired Student's t-test (survival data) where stated in Figure legends. For graphs showing changes over time, 1-way ANOVA was used to compared between groups. For percent changes between groups for comparisons area-under-the-curve (AUC) was determined for each parameter the compared to vehicle for percent difference unless otherwise stated for EOS measurements.

EXAMPLES

Example 1

COMPOUND A Effectively Treats Lupus in MRL/lpr Mice

Protocol

MRL/lpr mice were first randomized, initial bleeds collected, and body weights recorded for baseline measurements (FIG. 1). All mice were individually ear tagged and were monitored throughout the entire experiment (e.g., "Group#-Cage letter-Mouse#", so "3B5"=Group 3 (G3), cage B, mouse#5). Mice were age-matched and treatment started at 6-8 weeks of age. Cheek bleeds and urine collection continued weekly throughout the experiment. Mice were individually tracked for several parameters including cytokine and ANA levels, proteinuria, body mass, lymphomegaly, general health, and mortality. All parameters were evaluated bi-monthly except mortality which was monitored daily. All groups consisted of a minimum of at least 10-12 mice per group. Ex vivo experiments included flow cytometry analyses for plasma cells, serum complement C3 and ANA levels; urine protein and leukocytes, serum cytokine profiling, renal histo pathology, and determination of compound levels (pharmacokinetics (PK)) in the spleen, kidney and plasma. Mice were tracked on an individual basis. For all data, mice were grouped into populations and data graphed as mean±SEM. Bi-monthly observations and data collected were recorded for each group, except mortality which was performed daily. End-stage readouts were analyzed as described in the MATERIALS AND METHODS section (above) and in FIG. 1. For treatment with COMPOUND A, mice were treated with COMPOUND A suspended in PEG400 plus 1% DMSO provided orally (p.o.) twice daily (b.i.d.) from 8 to 11 weeks of age (i.e., for the 100 mg/kg dose, animals were administered 100 mg/kg in AM, and 100 mg/kg in PM), then rested without treatment from 11 to 18 weeks of age, then started again COMPOUND A drug treatments p.o. with b.i.d. dosing for the remaining three weeks until 21 weeks of age. Standard of care included dexamethasone (DEX) provided at 1.5 mg/kg, three times per week, i.p. Vehicle was PEG400+1% DMSO given orally twice a day at the same time as the COMPOUND A drug treatment. Pharmacokinetic analysis of tissue retention for this model can be found in FIG. 2. Of note with respect to FIG. 2 is that the level of COMPOUND A in kidney was similar to the plasma exposure level. This is important because the kidney is an important site of disease pathology in lupus.

Lymphomegaly, Splenomegaly, and Leucocyte Counts

Figure 3:
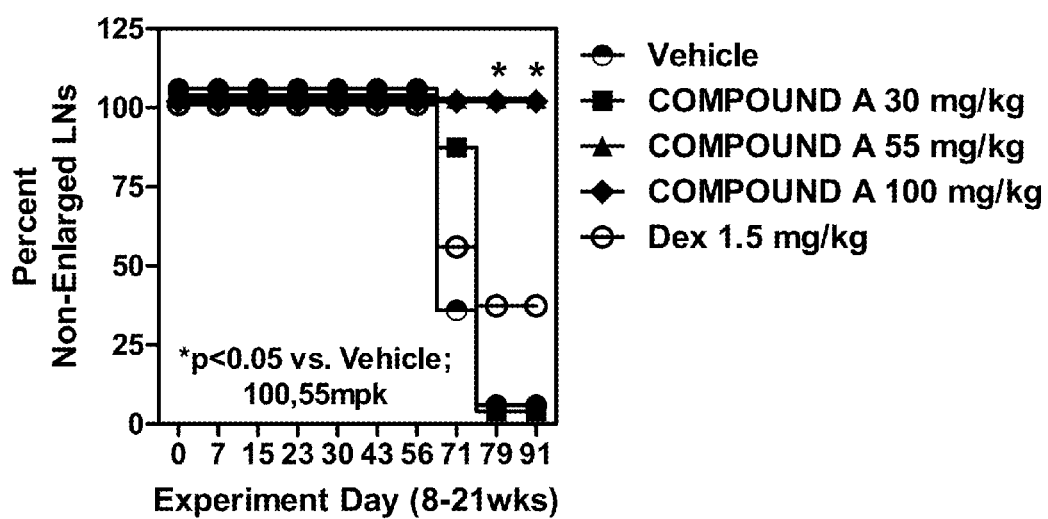
FIG. 3 depicts the reduced incidence of lympomegaly in COMPOUND A treated MRL/lpr mice.

MRL/lpr mice treated with COMPOUND A exhibited reduced lymphomegaly for the 55 mg/kg and 100 mg/kg, but not 30 mg/kg, doses (100% without lymphomegaly for 100 and 55 mg/kg, 0% for vehicle; p<0.05) (FIG. 3). MRL/lpr mice treated with COMPOUND A exhibited splenomegaly (i.e., spleen mass) at the 100 mg/kg and 55 mg/kg doses (p<0.001 and p<0.05 respectively) as compared to vehicle (49.4% decrease for 55 mg/kg and 74.1% decrease for 100 mg/kg vs. vehicle) (FIG. 4, top panel). At 100 mg/kg, COMPOUND A decreased spleen mass to the level of a non-lupus control animal (MRL/Mp; 98 mg) (FIG. 4, top panel). MRL/lpr mice treated with COMPOUND A exhibited reduced total leukocyte counts compared to vehicle at both the 55 mg/kg and 100 mg/kg doses (p<0.05), but not as low as a non-lupus MRL/Mp animal (FIG. 4, bottom panel).

These results are important because splenomegaly (spleen swelling), lymphomegaly (lymph node swelling), and hyperproliferation of T and B cells are indicative of lupus disease in MRL/lpr mice. Therefore, the reduction in general lymphocyte numbers, and thus spleen and lymph node size, indicates that COMPOUND A partially controlled systemic autoimmune responses during treatment. Moreover, the fact that the spleen mass and total cell number did not fall below the non-lupus historical controls suggests that COMPOUND A did not cause overt immunosuppression, which might be expected from a complete JAK kinase blockade. Therefore, COMPOUND A is advantageous in that it provides a desirable therapeutic effect without unfavorable side effects.

Tolerability

Figure 5:
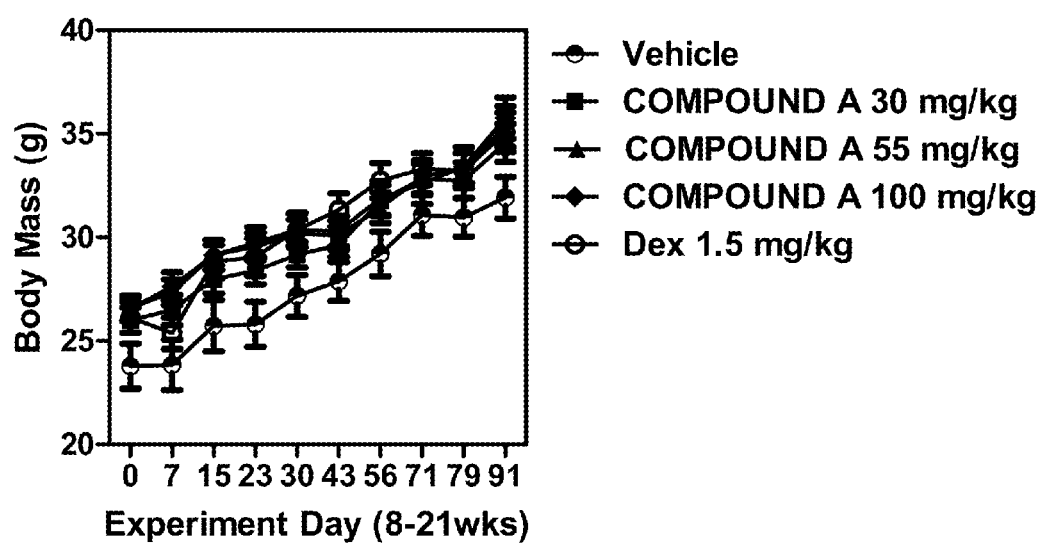
FIG. 5 depicts the change in body mass of MRL/lpr mice treated with COMPOUND A.

MRL/lpr mice treated with COMPOUND A exhibited no significant change in body mass (FIG. 5). For each dose tested overt toxicity was not observed, and body mass actually increased, suggesting improvement in overall health as compared to vehicle.

IL-12

Figure 6:
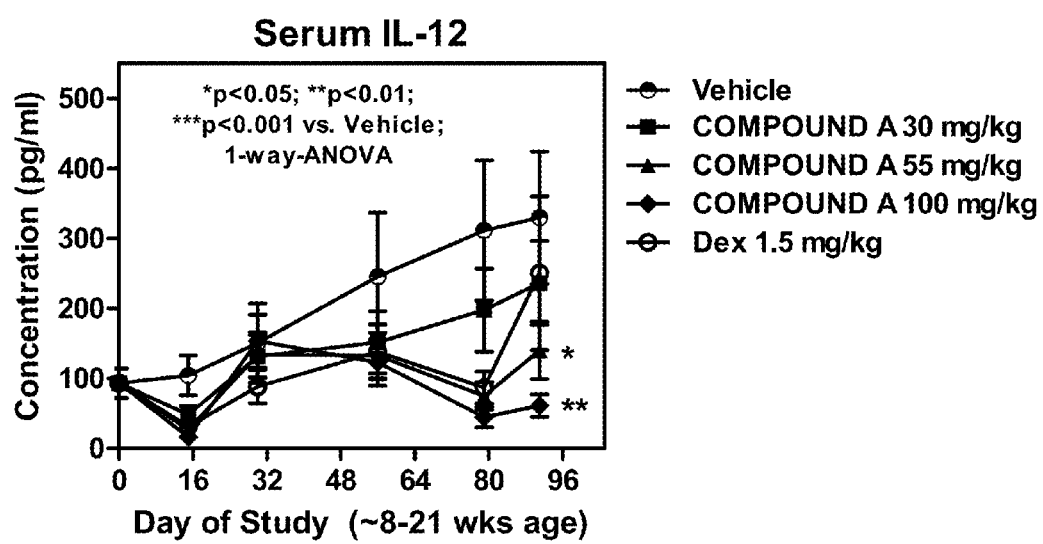
FIG. 6 depicts the levels of circulating IL-12 cytokine with and without treatment with COMPOUND A at various doses in MRL/lpr mice.

MRL/lpr mice treated with COMPOUND A exhibited falling IL-12 cytokine levels during treatment phases from 8-11 weeks of age and from 18-21 weeks of age, but rising levels during treatment holidays, 12-20 weeks of age (FIG. 6; *p<0.05, **p<0.01; 56.1% decrease for 100 mg/kg and 50.7% decrease for 55 mg/kg compared to vehicle).

This data is important because it supports the conclusion that COMPOUND A blocks inflammatory cytokine cascades involved in lupus, such as IL-12.

C3

Figure 7:
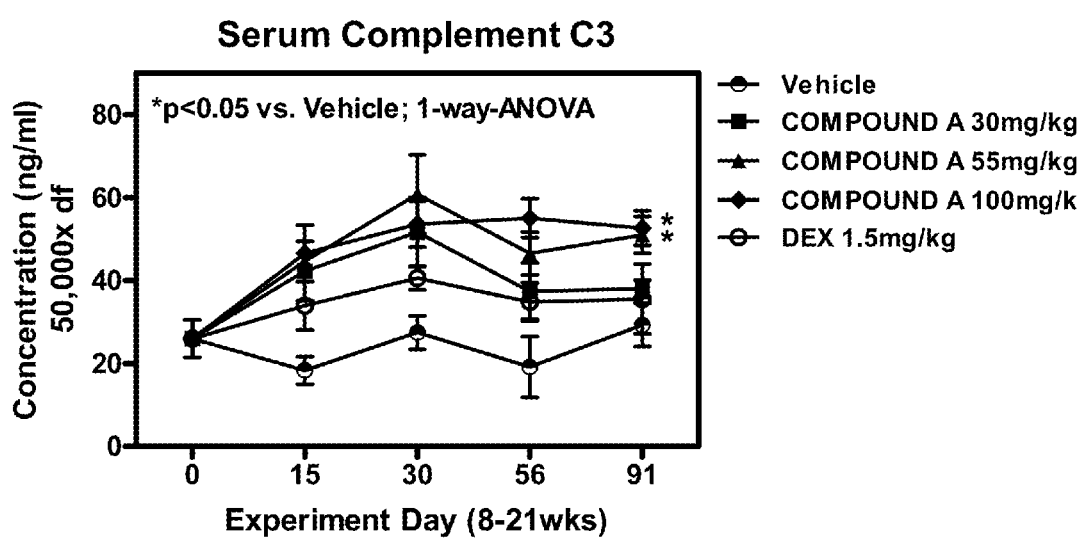
FIG. 7 depicts complement C3 levels in MRL/lpr mice treated with COMPOUND A.

MRL/lpr mice treated with COMPOUND A exhibited significantly increased serum C3 concentration relative to vehicle at the 55 mg/kg and 100 mg/kg doses (52.5% increase for 100 mg/kg and 51.4% increase for 55 mg/kg over vehicle; p<0.05) (FIG. 7).

This data is important because the level of C3 in the serum is indirectly correlated to the magnitude or extent of inflammation. SLE patients show reduced levels of C3 and C4 over time, which is indicative of increased systemic inflammation, which results in tissue organ damage. But with treatment these factors rebound, indicating that the treatment is reducing systemic inflammation and thus effectively treating the disease. Therefore, an increase in serum C3 is indicative of lupus disease resolution and treatment (Boumpas, Furie et al. 2003).

Lupus Nephritis

End-stage lupus nephritis was evaluated by histopathology and scored by a board certified pathologist for the assessment of total renal damage in diseased animals (FIG. 8; Table 1). MRL/lpr mice treated with COMPOUND A exhibited decreases in both cellular infiltrations/glomerulonephritis and glomerular size in hematoxylin and eosin (H&E) stained renal sections as compared to both the dexamethasone and vehicle treatment groups (FIG. 8). MRL/lpr mice treated with COMPOUND A exhibited significant reductions in glomerular cellularity (33.3% decrease; $p<0.01$), interstitial infiltration (40% decrease; $p<0.01$) and vasculitis (46.1% decrease; $p<0.01$) as compared to vehicle at the 100 mg/kg dose, similar to dexamethasone (Table 1). At the 55 mg/kg dose, COMPOUND A decreased interstitial infiltration (33.3% decrease; $p<0.05$) as compared to vehicle (Table 1).

These results are important because they show that treatment of MRL/lpr mice with COMPOUND A can slow and/or prevent the development of lupus nephritis in lupus-prone mice.

TABLE 1

MRL/lpr Kidney Scores (score grade: 0-5; mean ± SD)

| Group | Glomerular Cellularity | Glomerular Necrosis | Glomerulo-sclerosis | Interstitial Infiltration | Tubular Atrophy | Interstitial Fibrosis | Vasculitis |
|---|---|---|---|---|---|---|---|
| Vehicle | 3.60 ± 0.55 | 2.60 ± 0.55 | 2.40 ± 0.89 | 3.00 ± 0.71 | 2.00 ± 0.00 | 2.00 ± 0.00 | 2.60 ± 0.55 |
| COMPOUND A 30 mg/kg | 2.60 ± 0.55[1] | 1.80 ± 0.45 | 1.60 ± 0.55 | 2.20 ± 0.45 | 1.20 ± 0.45 | 1.60 ± 0.55 | 1.80 ± 0.45 |
| COMPOUND A 55 mg/kg | 3.20 ± 0.45 | 1.80 ± 0.45 | 2.00 ± 0.00 | 2.00 ± 0.71[1] | 2.20 ± 0.45 | 1.20 ± 0.45 | 2.00 ± 0.00 |
| COMPOUND A 100 mg/kg | 2.40 ± 0.55[2] | 1.8 ± 0.45 | 2.20 ± 0.84 | 1.80 ± 0.84[2] | 1.40 ± 0.55 | 1.40 ± 0.55 | 1.40 ± 0.55[2] |
| Dex 1.5 mg/kg | 3.00 ± 0.71 | 2.00 ± 0.00 | 2.00 ± 0.00 | 1.60 ± 0.55[3] | 1.20 ± 0.45 | 1.20 ± 0.45 | 1.40 ± 0.55[2] |

Compared to Vehicle
[1] $p < 0.05$
[2] $p < 0.01$
[3] $p < 0.001$
1-way ANOVA

Pharmacodynamics

Figure 9:
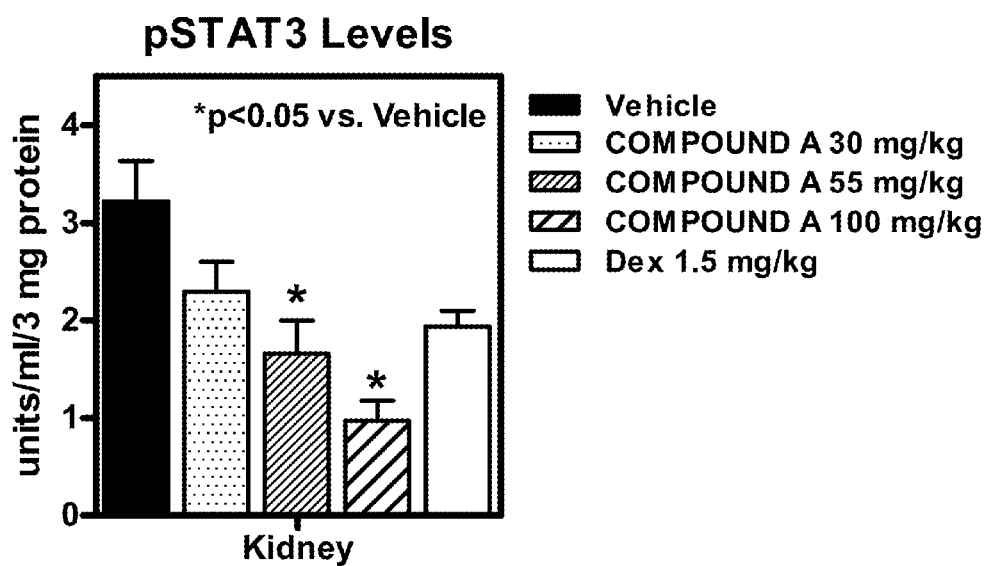
FIG. 9 depicts reduced levels of a JAK2 target, pSTAT3 in diseased kidneys of MRL/lpr mice.

Inhibition of phosphorylated STAT-3 (pSTAT3) was used as a downstream pharmacodynamic (PD) marker of JAK2 inhibition. Significant reductions in renal pSTAT3 were observed for both the 55 mg/kg and 100 mg/kg doses of COMPOUND A in MRL/lpr mice four hours after final dosing of drug at end-of-study (EOS) day 147 of age (day 91 of study) (FIG. 9).

This data is important because it shows that COMPOUND A was effectively inhibiting JAK2 at a location of particular importance to lupus—the kidney.

Plasma Cells

Figure 10A:
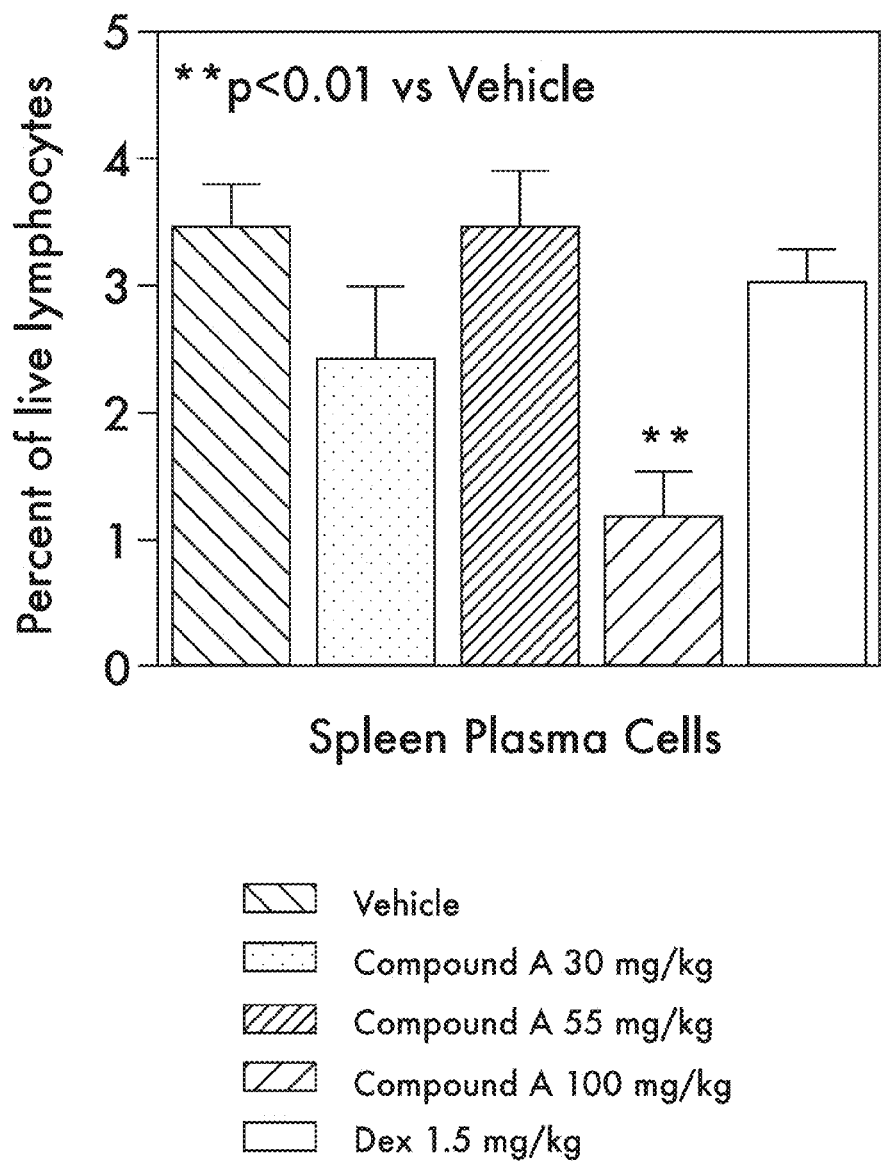
Figure 11:
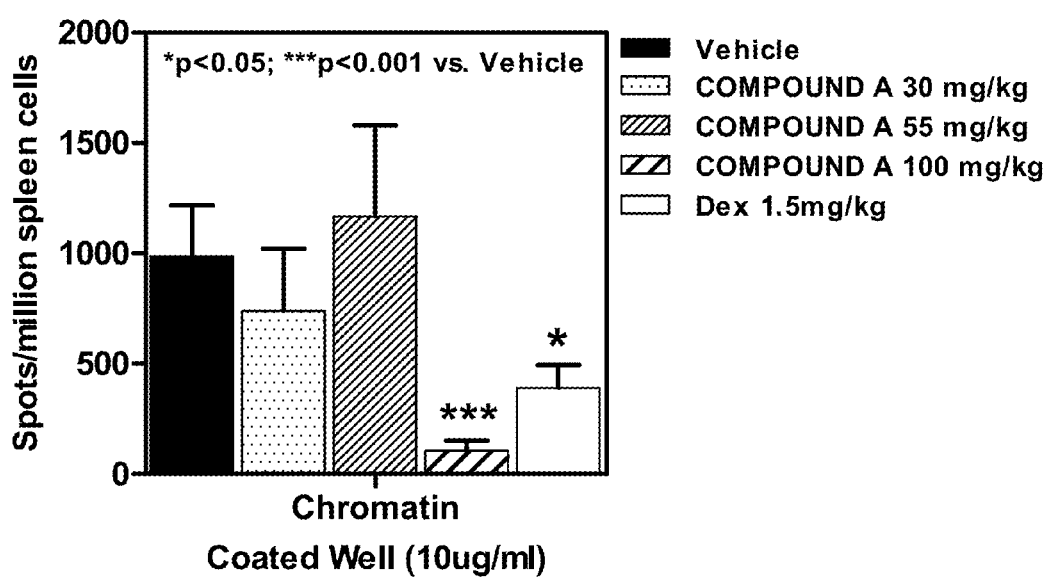
FIG. 11 depicts reduced levels of ASCs in the spleens of COMPOUND A treated MRL/lpr mice. The reduction in ASCs secreting anti-chromatin antibodies for the 100 mg/kg dose correlates well with the reduction in PC proportions in the spleen as measured by flow cytometry at the same dose (FIG. 10).

MRL/lpr mice treated with COMPOUND A exhibited decreased spleen plasma cells at the 100 mg/kg dose as compared to vehicle (65.5% decrease; $p<0.01$) (FIG. 10). MRL/lpr mice treated with COMPOUND A exhibited reduced frequency of anti-chromatin antibody secreting cells (ASCs) in the spleen at the 100 mg/kg dose as compared to vehicle (89.1% decrease; $p<0.001$) (FIG. 11).

This data is important because plasma cells are responsible for the generation of autoantibodies, and long-lived plasma cells are thought to be one of the root propagators of contin-ued lupus pathogenesis in humans (Espeli, Bokers et al.; Neubert, Meister et al. 2008). Long-lived plasma cells (LL-PCs) primarily populate the bone marrow (BM), but can also be found in the spleen at sites of inflammation, and are known to be resistant to cyclophosphamide, one accepted therapy for treating lupus nephritis (Chevrier, Genton et al. 2009).

Example 2

COMPOUND A Effectively Treats Lupus in NZM Mice

Protocol

Figure 12:
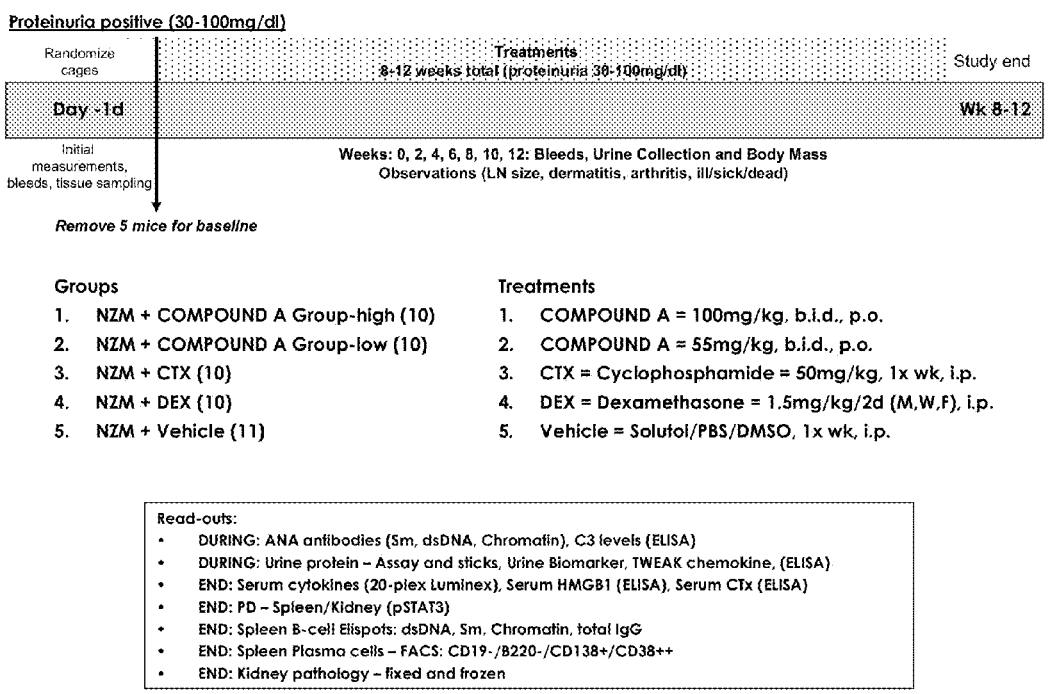
FIG. 12 depicts an overview of how COMPOUND A was tested in the slow spontaneous NZM mouse model for human lupus.

Age mated, female, NZM or NZW/LacJ, mice were matured for the study of lupus nephritis for a total of 7 months or 210 days at which time urine was collected for proteinuria detection. Mice with 0.5-1.0 mg/ml of urine protein as determined by an optical density-based total protein precipitation assay and cross-checked for 30-300 mg/dl of protein as determined by a stick assay were considered proteinuria positive and selected for study entry. Groups were normalized to contain a Gaussian distribution of proteinuria positive animals (i.e., ⅓ low proteinuria, ⅓ medium, ⅓ high) then randomized between groups before ear marking and taking baseline measures including urine and serum collections. A total of five mice from the total population were randomly selected for baseline kidney histology evaluation. Treatments and tests for each group are as described in FIG. 12. Briefly, with a minimum of 10 mice per group, COMPOUND A was administered at 100 mg/kg or 55 mg/kg, both twice a day and orally. For standards of care, cyclophosphamide (CTX) was provided at 50 mg/kg, once weekly, ip and dexamethasone provided at 1.5 mg/kg, three times a week, ip. Vehicle included 3% DMSO, 10% Solutol and 87% PBS. Treatments started on day of age, 212, some mice died shortly after treatment but all animals regardless of health status were counted against the total group size from time of dosing. End-stage lupus nephritis was evaluated by histopathology and scored by a board certified pathologist for the assessment of total renal damage in diseased animals using the scoring method described by Smith et al (Smith, Dong et al. 2007). It is important to note, that all graphs shown in the relevant Figures show day-0 as being the "start of treatment" and thus represents 212 days of age. Day-98 or "end of treatment/study" represents 310 days of age for the NZM animals. All graphs show time as "day on study" with day on study starting at 212 days of age and ending at 310 days of age.

Survival

Figure 13:
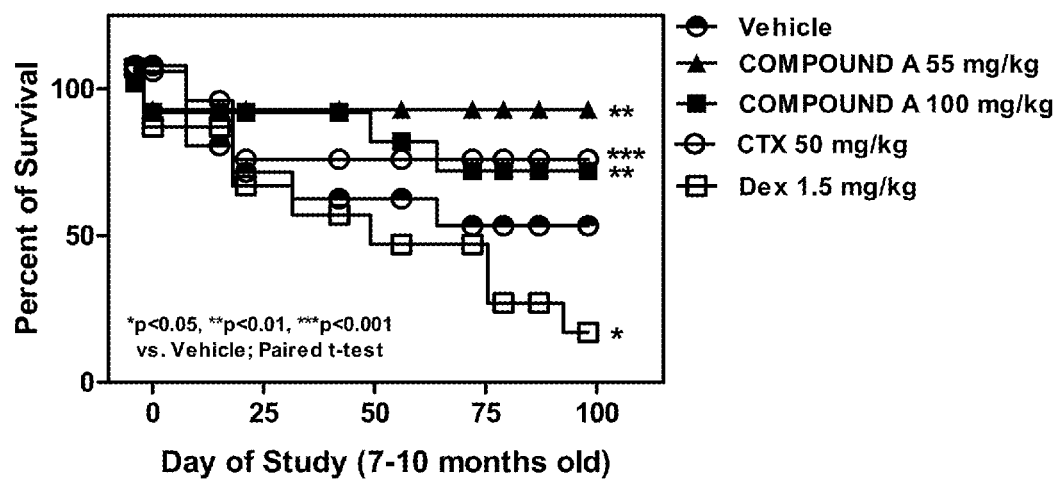
FIG. 13 depicts the increased survival of NZM mice treated with COMPOUND A over that of vehicle or Dex.

NZM mice treated with COMPOUND A exhibited significantly increased survival relative to vehicle at the 55 mg/kg and 100 mg/kg doses (70% survival for 100 mg/kg and 90% survival for 55 mg/kg at EOS; p<0.01). Survival was comparable to standard of care agent CTX (70% survival at EOS; p<0.001) (FIG. 13). Along with MMF and Azathioprine, Cyclophosphamide is a current treatment option for patients suffering from lupus nephritis as it acts as a potent immunosuppressive agent, however, due to its severe side-effects it is used only in the most severe cases.

Antinuclear Antibodies (ANAs)

Figure 14:
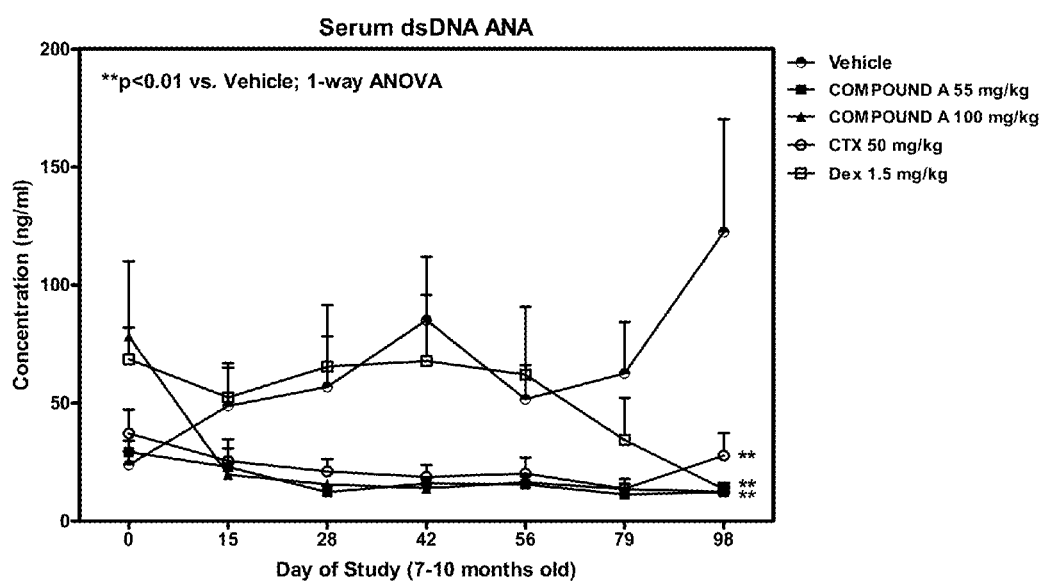
FIG. 14 depicts the levels of serum anti-dsDNA ANAs over time with COMPOUND A treatment in NZM mice.
Figure 15:
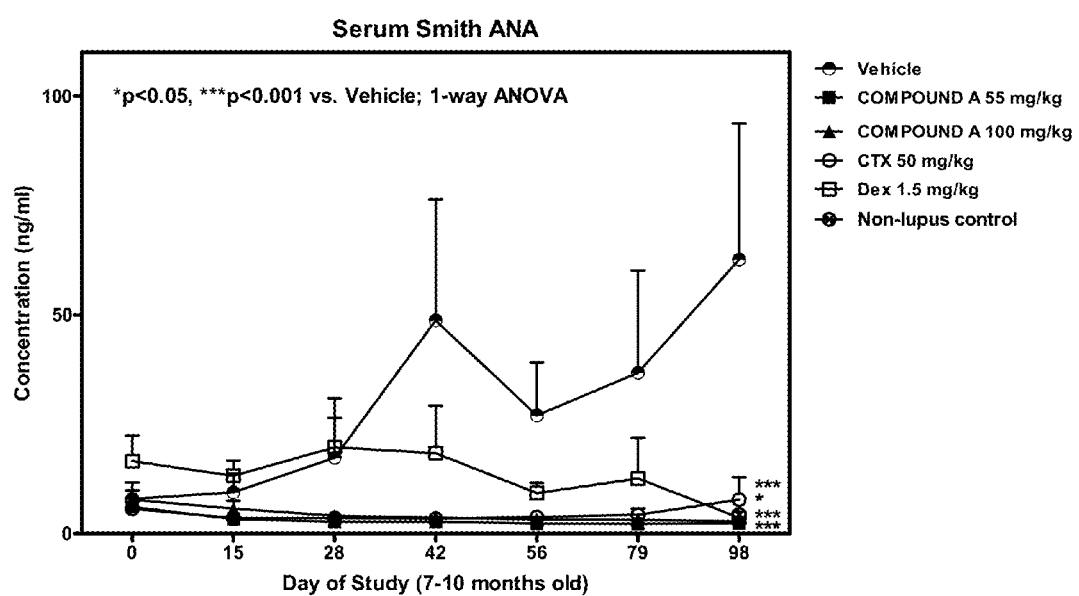
FIG. 15 depicts the levels of serum anti-smith ANAs over time with COMPOUND A treatment in NZM mice.

NZM mice treated with COMPOUND A exhibited reduced overall levels of serum anti-dsDNA ANAs throughout the course of disease (73.9% decrease for 100 mg/kg, 67.0% decrease for 55 mg/kg as compared to the vehicle; p<0.01). Reduction in anti-dsDNA ANAs by COMPOUND A was on par with standard of care agent CTX (65.3% decrease as compared to vehicle; p<0.001) (FIG. 14). Treatment with COMPOUND A (and CTX) also significantly reduced anti-smith antigen ANAs (p<0.05) (FIG. 15).

This data is important because the presence of anti-dsDNA antibodies is associated with a poor prognosis of lupus and is strongly associated with developing, and often fatal, lupus nephritis (Egner 2000; Kiss, Lakos et al. 2009).

IFNα

Figure 16:
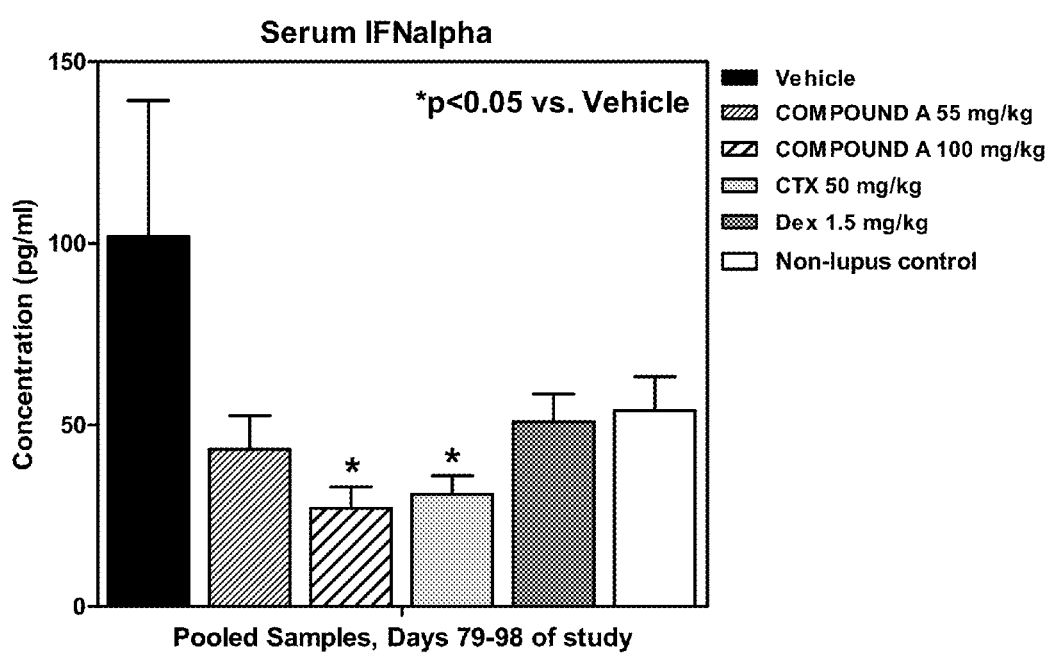
FIG. 16 depicts the levels of IFNalpha cytokine in the serum at EOS for the NZM mice treated with COMPOUND A.

NZM mice treated with COMPOUND A exhibited modest but significant reduction in serum IFNα as compared to vehicle (73.2% decrease for 100 mg/kg and 70.2% decrease for 55 mg/kg; p<0.05) (FIG. 16). Neither standard of care agent (i.e., CTX or DEX) exhibited a significant reduction.

This data is important because the type I IFN cytokine, IFNα, has been strongly linked to the pathogenesis of lupus and is one of the earliest bursts of cytokines leading to lupus manifestations in humans (Niewold, Hua et al. 2007). In fact, lupus therapies are currently being developed that specifically target IFNα to neutralize circulating IFNα in lupus patients (e.g., MedImmune, MEDI-545). Decrease of this 'IFNα signature' in lupus patients is one biomarker used in determining the efficacy of a tested experimental medicine (Sozzani, Bosisio et al.).

Proteinuria

Figure 17:
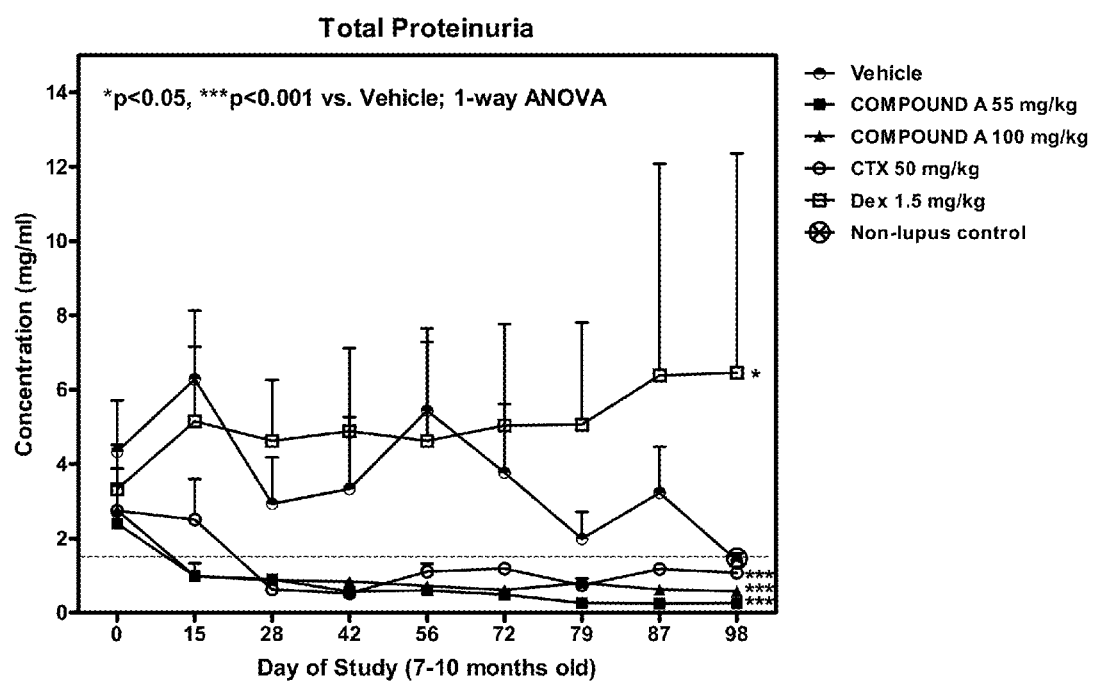
FIG. 17 depicts total urine protein measured over time with treatment with COMPOUND A in NZM mice.
Figure 18A:
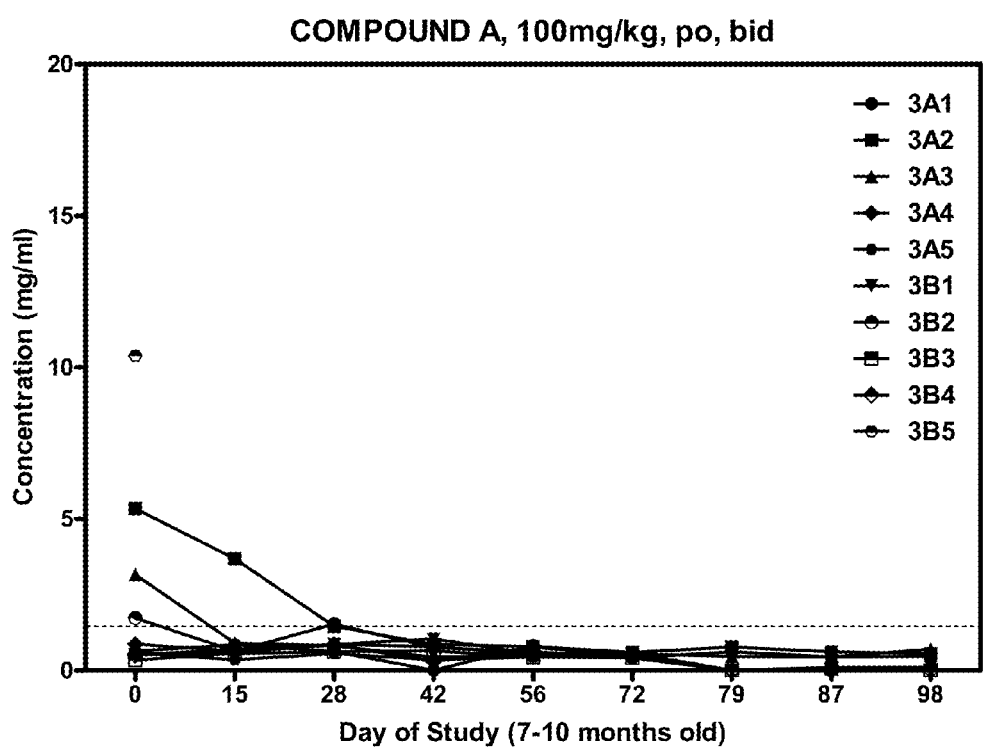
FIGS. 18A to E depict the levels of total urine protein measured by individual NZM mice over time with treatment with COMPOUND A.
Figure 18B:
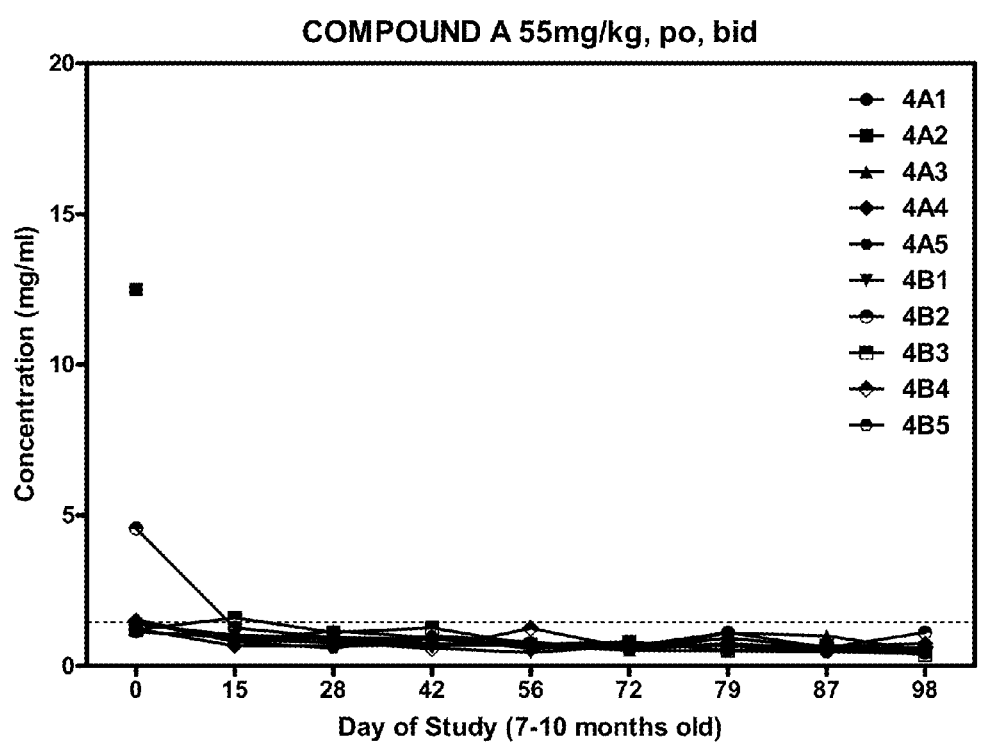
Figure 18C:
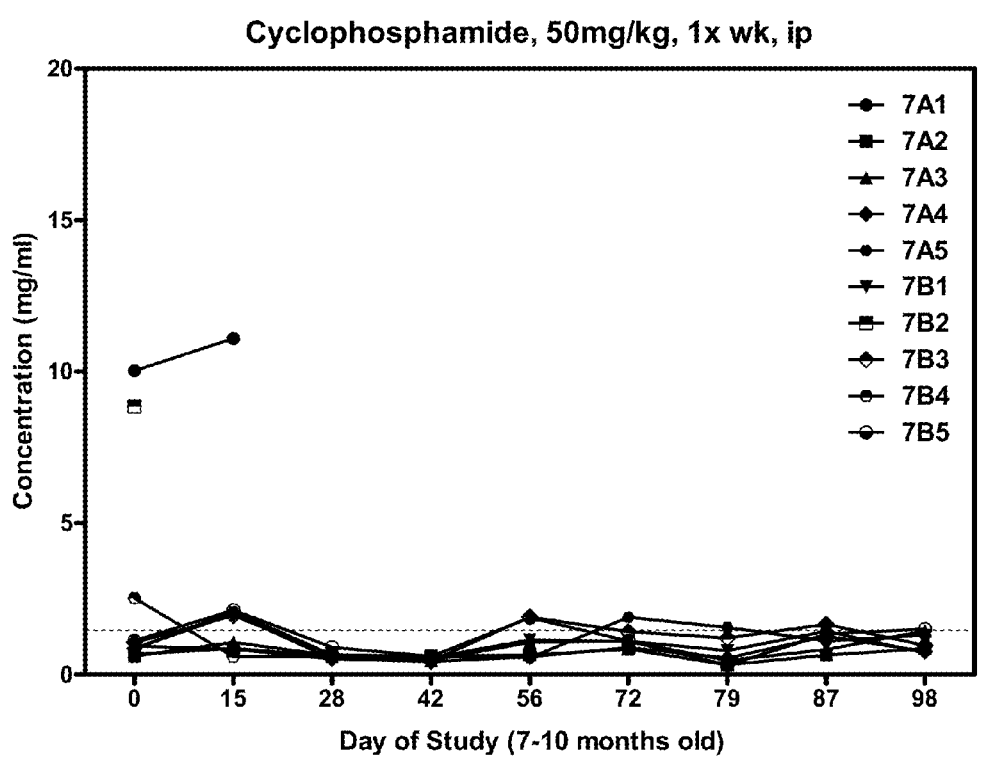
Figure 18D:
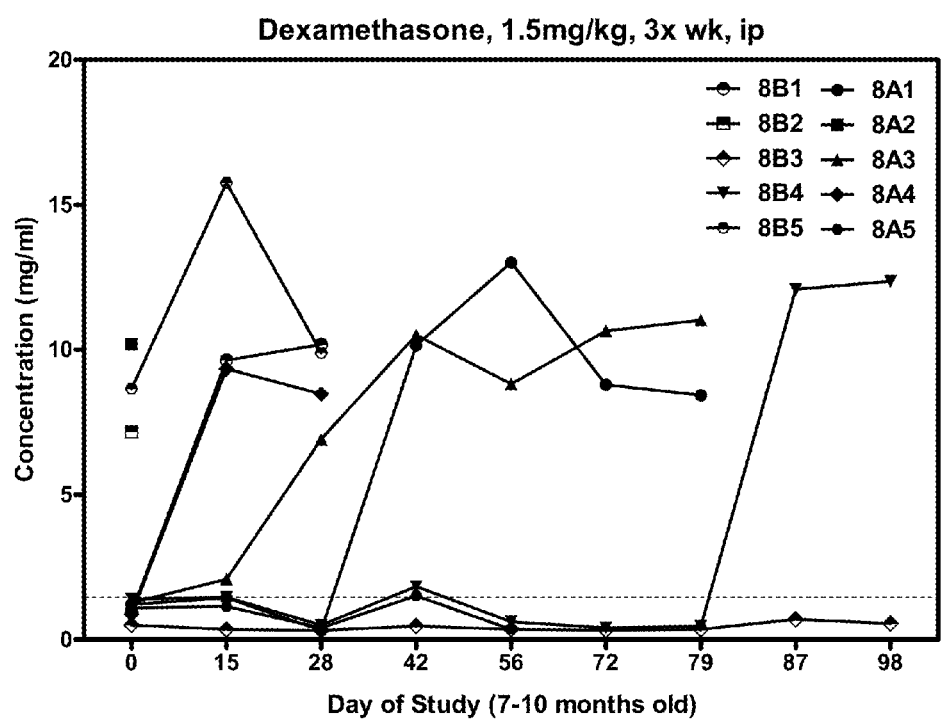
Figure 18E:
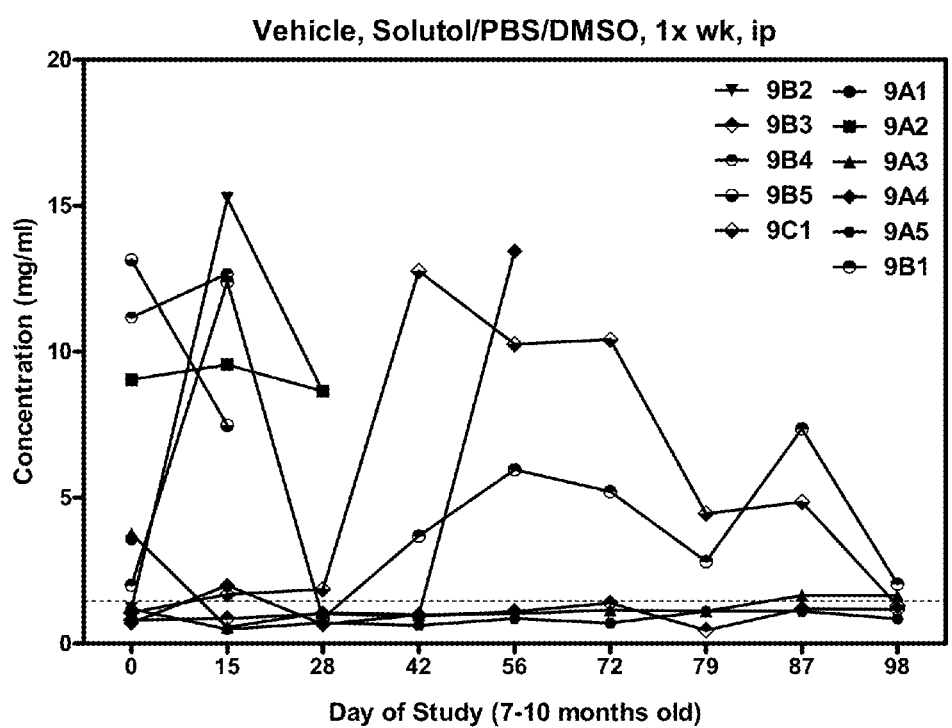

NZM mice treated with COMPOUND A exhibited significantly reduced total urine protein over the course of disease for both treatment groups, 55 mg/kg and 100 mg/kg, relative to vehicle (76.25 decrease and 81.8% decrease as compared to vehicle respectively; p<0.001). (FIG. 17). The reduction was comparable to standard of care agent CTX (67.1% decrease; p<0.001). The data for individual mice in each treatment group is shown in FIGS. 18A to 18E. NZM mice treated with COMPOUND A exhibited reduced proteinuria as compared to DEX or vehicle (e.g., less variable magnitude and duration of response), comparable to CTX. Treatment with COMPOUND A brought protein levels to below the protein levels of age-matched, non-lupus control mice (FIG. 17; dotted line).

These results are important because an increase in urine protein (proteinuria) is the direct result of renal damage associated with lupus nephritis. Moreover, the fact that COMPOUND A reduced urine protein levels to below the levels of historical non-lupus control animals indicates that COMPOUND A was not merely protecting the animals from disease advancement, but was actually reversing the lupus disease.

Glomerulonephritis, Lung Damage

NZM mice treated with COMPOUND A exhibited decreased glomerular cellularity at the 55 mg/kg and 100 mg/kg doses as compared to vehicle (59.3% decrease and 56.2% decrease respectively; p<0.001) (Table 2). NZM mice treated with COMPOUND A at the 55 mg/kg and 100 mg/kg doses exhibited reduced interstitial fibrosis and vasculitis as compared to vehicle (58.3% and 8.3% decrease respectively; p<0.05) (Table 2). NZM mice treated with COMPOUND A exhibited decreased renal pathologies, comparable to those of a non-diseased NZW/LacJ parental age-matched control (FIG. 19). NZM mice treated with COMPOUND A at the 55 mg/kg and 100 mg/kg doses (and CTX) prevented lung infiltrates as compared to dexamethasone and vehicle treated animals (FIG. 20).

TABLE 2

NZM Kidney Scores (score grade: 0-5; mean ± SD)

| Group | Glomerular Cellularity | Glomerular Necrosis | Glomerulosclerosis | Interstitial Infiltration | Tubular Atrophy | Interstitial Fibrosis | Vasculitis |
|---|---|---|---|---|---|---|---|
| Vehicle | 3.22 ± 0.83 | 2.11 ± 0.60 | 2.55 ± 1.33 | 2.44 ± 1.33 | 2.66 ± 1.22 | 2.44 ± 1.33 | 1.20 ± 0.44 |
| COMPOUND A 55 mg/kg | 1.33 ± 0.50[3] | 1.22 ± 0.44 | 1.00 ± 0.0[1] | 1.11 ± 0.33 | 1.22 ± 0.44 | 1.0 ± 0.0[1] | 1.11 ± 0.33[1] |
| COMPOUND A 100 mg/kg | 1.44 ± 0.52[3] | 1.44 ± 0.72 | 1.22 ± 0.66 | 1.22 ± 0.44 | 1.33 ± 0.50 | 1.22 ± 0.44 | 1.44 ± 0.52 |
| CTX 50 mg/kg | 2.0 ± 0.70[1] | 1.77 ± 0.83 | 2.11 ± 1.16 | 1.55 ± 1.01 | 2.00 ± 1.32 | 1.55 ± 1.01 | 1.33 ± 0.50 |
| Dex 1.5 mg/kg | 3.0 ± 0.81 | 3.0 ± 0.81 | 3.42 ± 1.27 | 2.71 ± 0.47 | 3.14 ± 1.46 | 2.71 ± 1.25 | 2.42 ± 1.13 |
| NZM 8 mos baseline | 2.50 ± 1.00 | 1.50 ± 0.57 | 2.00 ± 0.81 | 1.50 ± 1.00 | 2.00 ± 1.41 | 2.00 ± 1.41 | 1.75 ± 0.50 |
| Non-lupus control | 1.40 ± 0.89[2] | 1.20 ± 0.44 | 1.20 ± 0.44 | 1.20 ± 0.44 | 1.40 ± 0.89 | 1.20 ± 0.44 | 1.20 ± 0.44 |

Compared to Vehicle
[1] p < 0.05
[2] p < 0.01
[3] p < 0.001
2-way ANOVA

Figure 21:
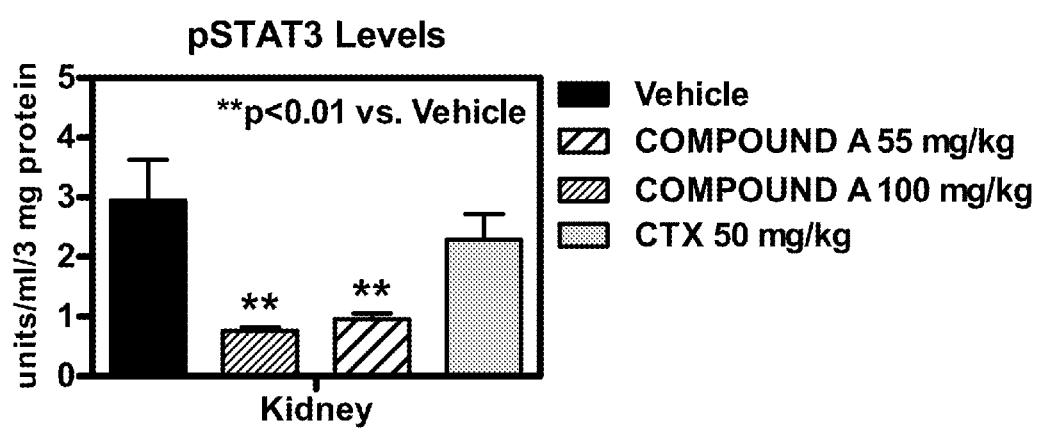
FIG. 21 depicts reduced levels of the JAK2 target pSTAT3 in the lupus disease tissue, kidney, post oral dosing of COMPOUND A in NZM mice.
Figure 22:
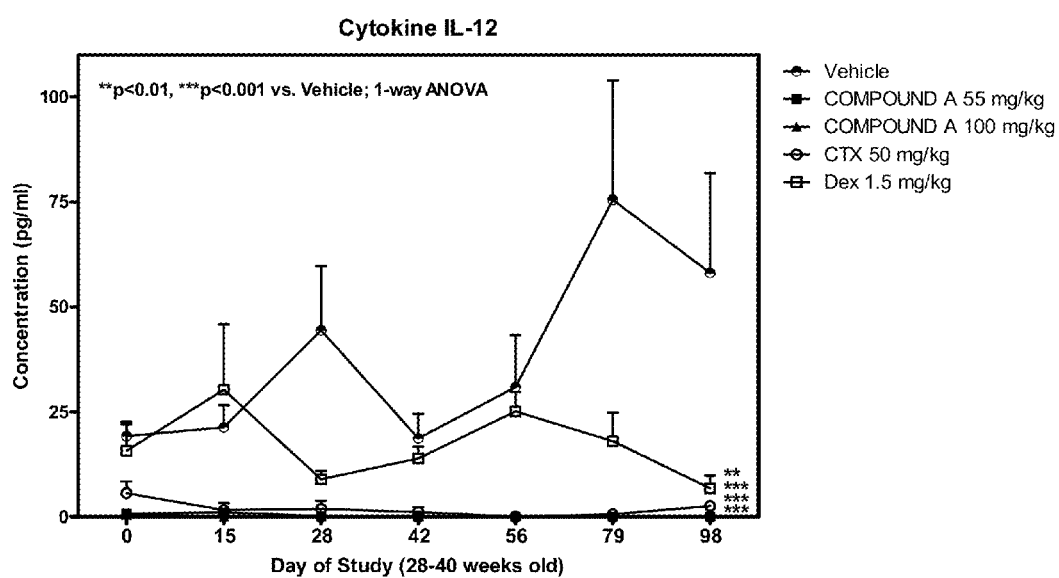
FIG. 22 depicts the levels of IL-12 cytokine measured over time with treatment of COMPOUND A in NZM mice.
Figure 23:
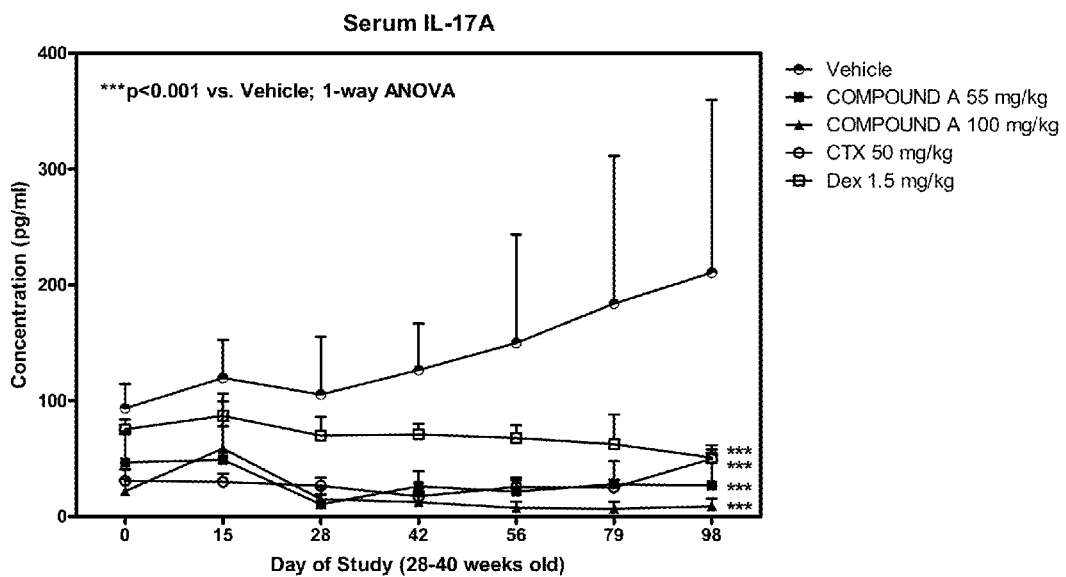
FIG. 23 depicts the levels of IL-17A cytokine measured over time with treatment of COMPOUND A in NZM mice.
Figure 24:
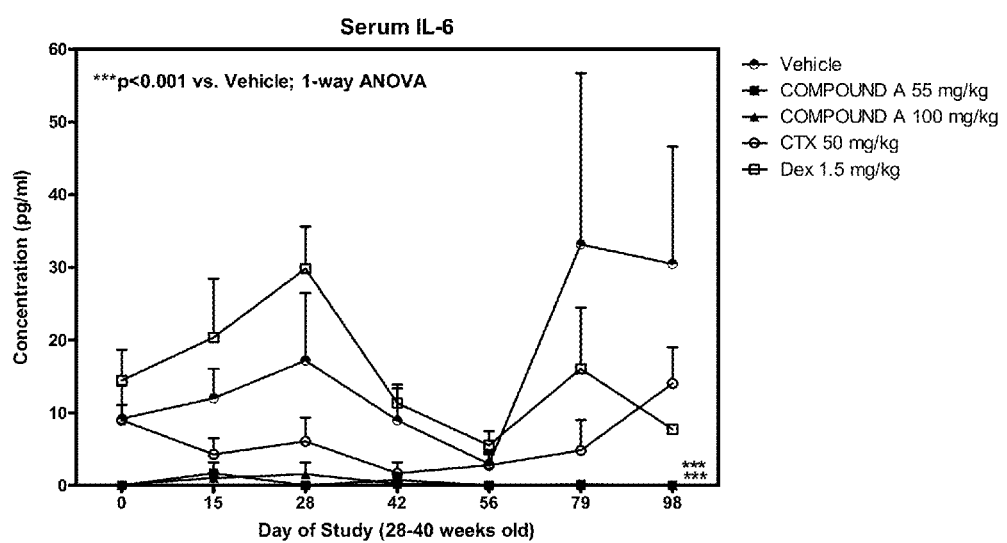
FIG. 24 depicts the levels of IL-6 cytokine measured over time with treatment of COMPOUND A in NZM mice.
Figure 25:
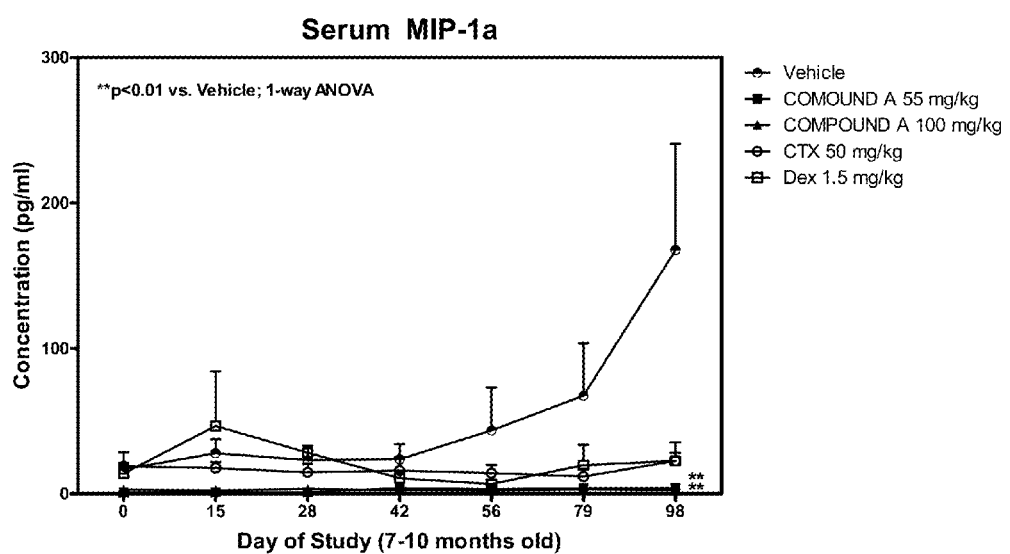
FIG. 25 depicts the levels of MIP-1alpha chemokine measured over time with treatment of COMPOUND A in NZM mice.
Figure 26:
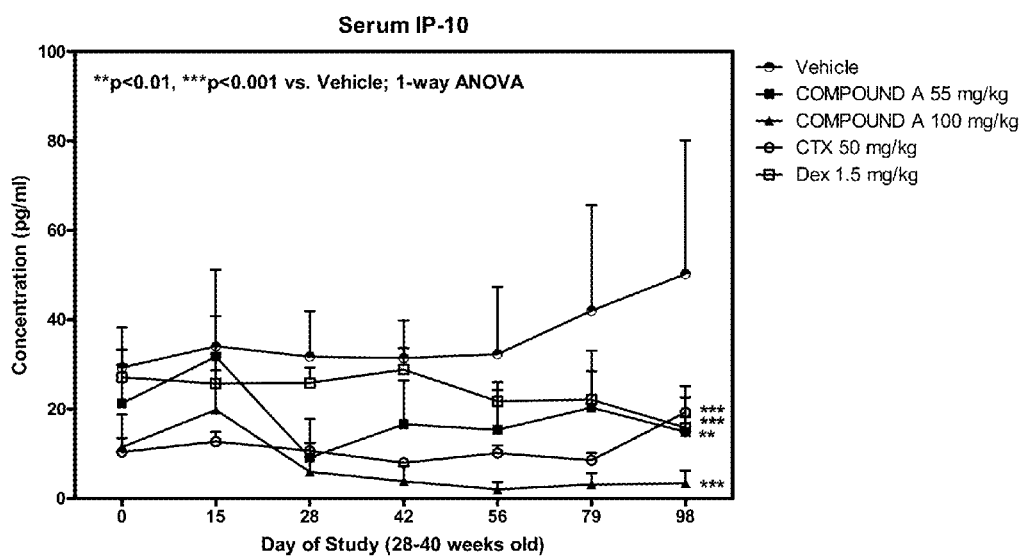
FIG. 26 depicts the levels of chemokine CXCL10/IP-10 measured in the serum over time with treatment of COMPOUND A in NZM mice.
Figure 27:
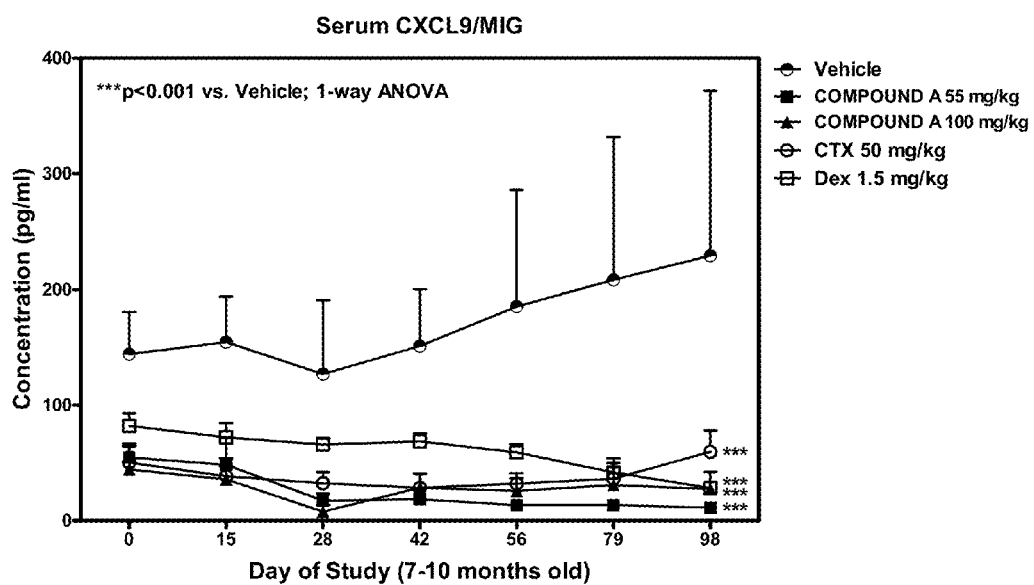
FIG. 27 depicts the levels of chemokine CXCL9/MIG measured in the serum over time with treatment of COMPOUND A in NZM mice.
Figure 28:
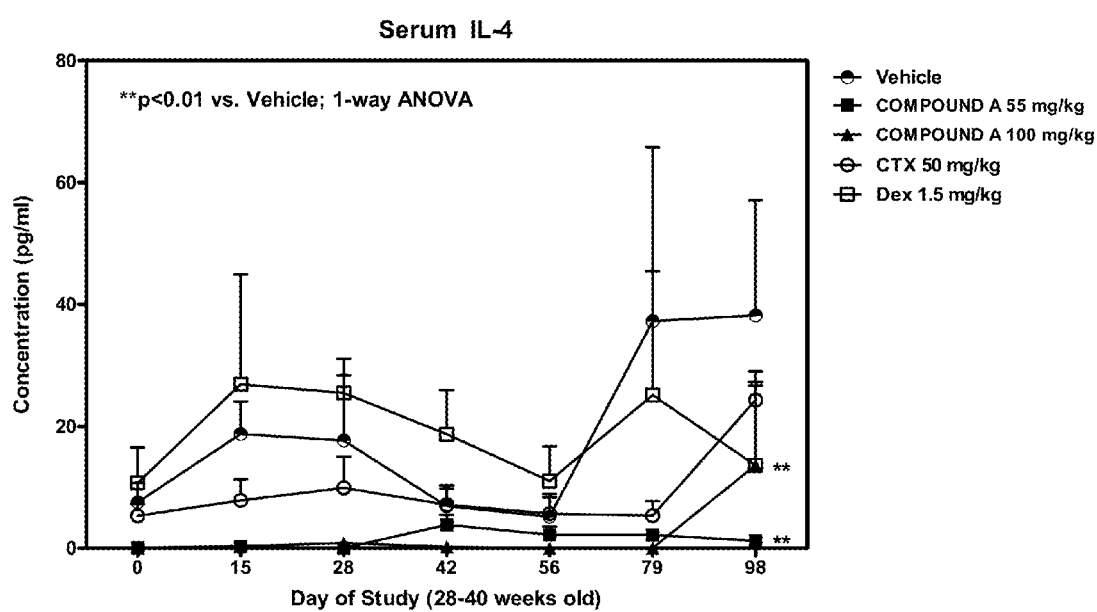
FIG. 28 depicts the levels of cytokine IL-4 measured in the serum over time with treatment of COMPOUND A in NZM mice.
Figure 29:
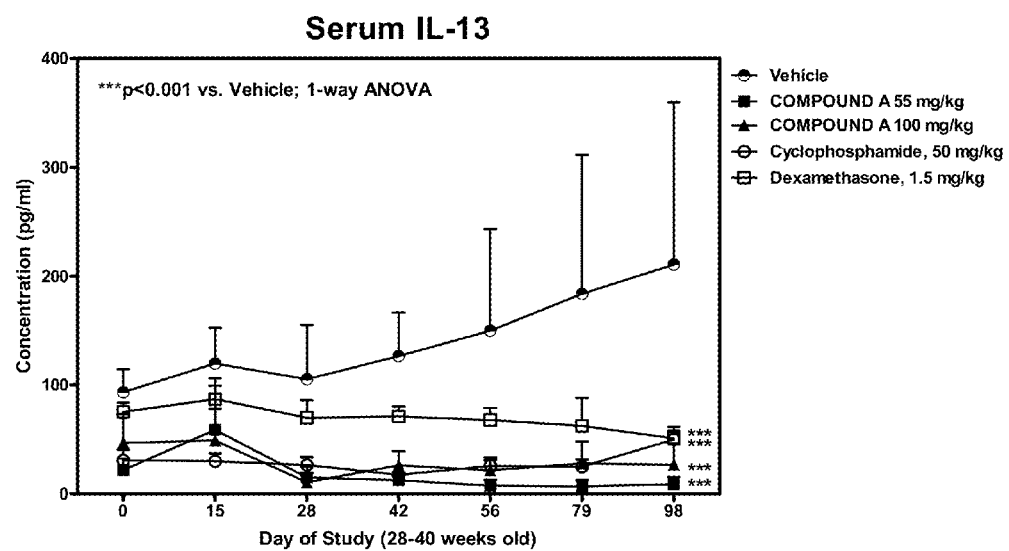
FIG. 29 depicts the levels of cytokine IL-13 measured in the serum over time with treatment of COMPOUND A in NZM mice.
Figure 30:
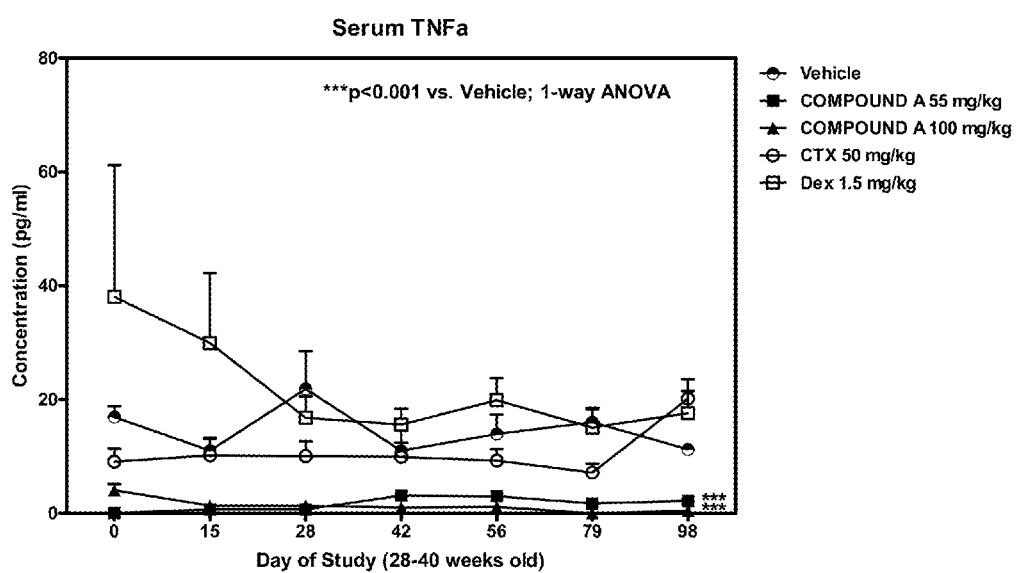
FIG. 30 depicts the levels of TNFalpha measured in the serum over time with treatment of COMPOUND A in NZM mice.
Figure 31:
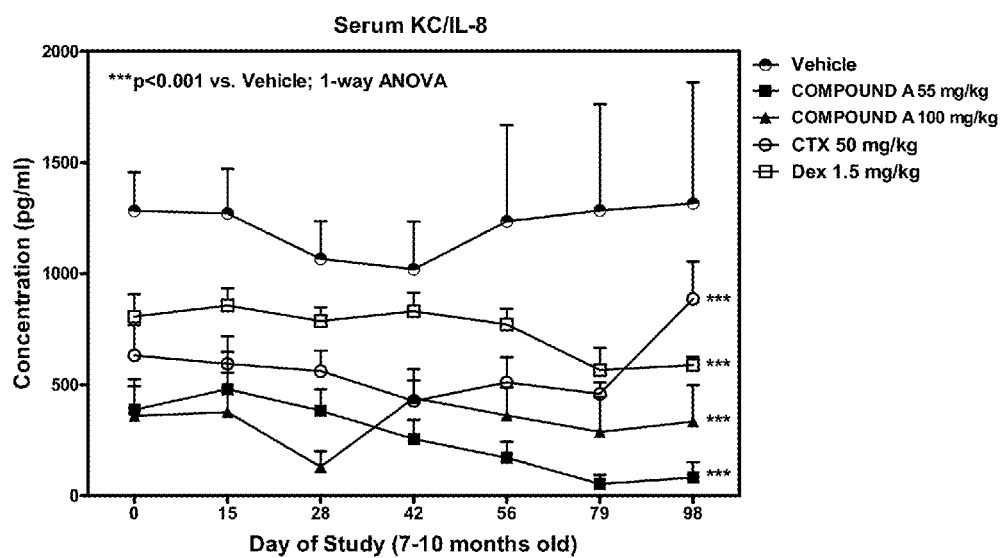
FIG. 31 depicts the levels of chemokine KC/IL-8 measured in the serum over time with treatment of COMPOUND A in NZM mice.

This data is important because glomerular cellularity, interstitial fibrosis, and vasculitis are indicators of glomerulonephritis associated with lupus. The fact that COMPOUND A was able to not only prevent an increase in these factors, but to reduce them as compared to the 7-month baseline NZM mice, indicates that COMPOUND A was going beyond merely protecting the animals from disease progression and actually reversing the course of disease. In addition, pulmonary edema or pulmonary vasculitis and pleura effusions can lead to upper respiratory complications such as pneumonia. The ability of COMPOUND A to preventing lung vasculitis and inflammation is an advantage of the present invention, since these are common complications of lupus disease Pharmacodynamics Using the pharmacodynamic marker phosphor-STAT3 for JAK2 inhibition, levels of pSTAT3 in the kidneys of treated mice were significantly lower than those in either vehicle or CTX (% change; $p<0.01$) (FIG. 21).

This data is important because it shows that COMPOUND A was effectively inhibiting JAK2 at a location of particular importance to lupus—the kidney.

Cytokines

NZM mice treated with COMPOUND A exhibited significantly reduced serum levels of several cytokines associated with lupus progression as compared to vehicle (FIGS. 22-31). For example, the 55 mg/kg and 100 mg/kg doses of COMPOUND A significantly reduced IL-12 (99.4% and 99.9% decrease; $p<0.001$) (FIG. 22), IL-17A (79.1% and 86.2% decrease; $p<0.001$) (FIG. 23), IL-6 (98.2% and 97.0% decrease; $p<0.001$) (FIG. 24), CCL3/MIP-1α (94.5% decrease for both doses; $p<0.01$) (FIG. 25), CXCL10/IP-10 (47.3% and 80.0% decrease; $p<0.01$) (FIG. 26), CXCL9/MIG (83.7% and 85.7% decrease; $p<0.001$) (FIG. 27), IL-4 (98.7% and 91.8% decrease; $p<0.01$) (FIG. 28), IL-13 (86.2% and 79.5% decrease; $p<0.001$) (FIG. 29), TNFα (92.3% and 88.3% decrease; $p<0.001$) (FIG. 30), and KC/IL-8 (78.0% and 72.9% decrease; $p<0.001$) (FIG. 31) as compared to vehicle.

These results are important because these cytokines are elevated in lupus patients, and are involved in the augmentation of lupus flares and ongoing immune responses to self antigens perpetuating the disease (Chun, Chung et al. 2007; Tucci, Lombardi et al. 2008). Reduction or modulation in these cytokine profiles can provide a favorable benefit for patients and provides an indirect indicator of disease resolution. (Morimoto, Tokano et al. 2001; Aringer and Smolen 2004; Chun, Chung et al. 2007; Niewold, Hua et al. 2007; Fu, Chen et al. 2008; Tucci, Lombardi et al. 2008).

Splenomegaly

Figure 32:
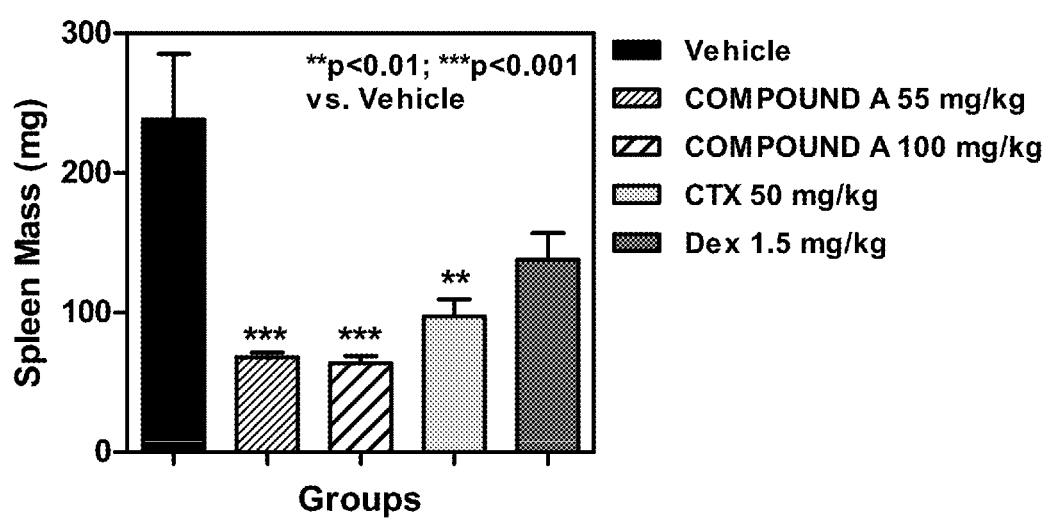
FIG. 32 depicts the spleen mass of NZM mice treated with COMPOUND A at EOS.

NZM mice treated with COMPOUND A exhibited significantly reduced total end of study (EOS) spleen mass as compared to vehicle (73.5% decrease for 100 mg/kg and 71.8% decrease for 55 mg/kg; $p<0.001$). (FIG. 32). The decrease in spleen mass observed for COMPOUND A was comparable to CTX.

This data is important because splenomegaly (spleen swelling) is indicative of lupus disease in NZM mice.

Tolerability

Figure 33:
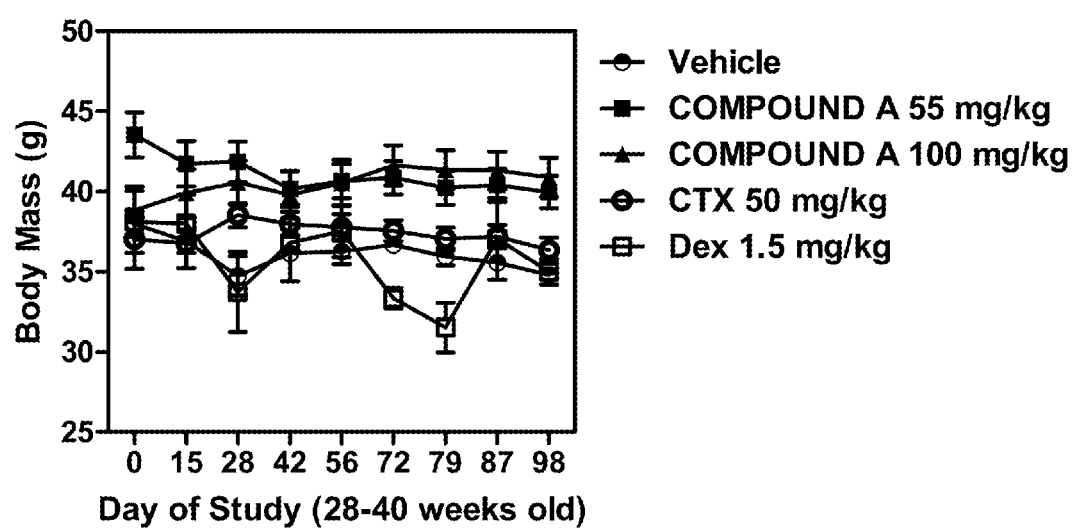
FIG. 33 depicts the average body mass measured over time in NZM mice treated with COMPOUND A.

NZM mice treated with COMPOUND A exhibited no change in body mass at either dose (FIG. 33).

Osteoclast Activity

Figure 34:
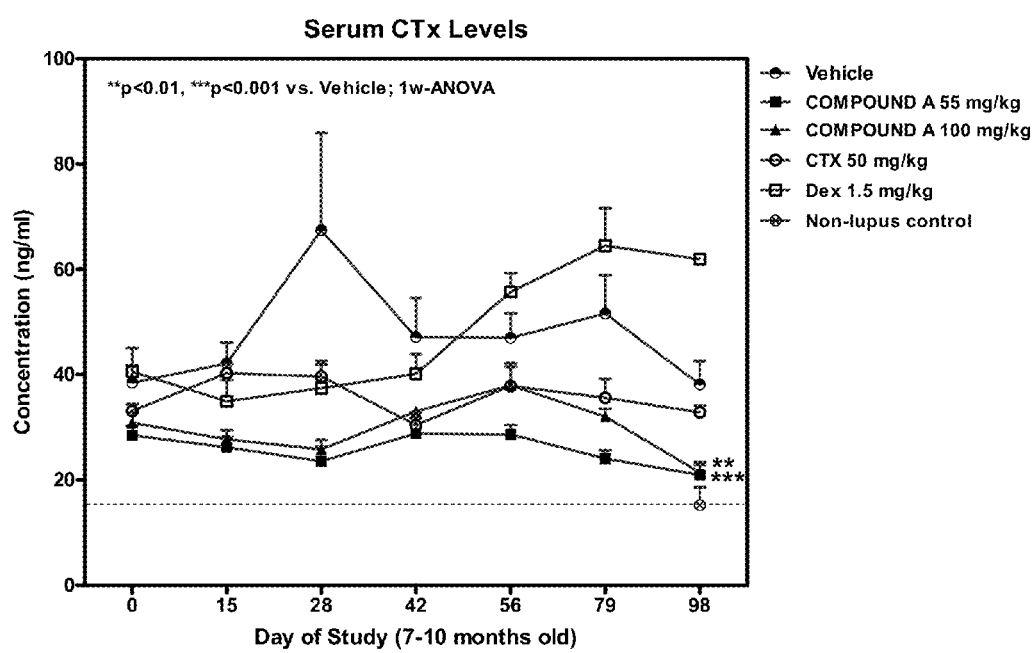
FIG. 34 depicts the average levels of bone resorption biomarker CTx measured over time in the serum of NZM mice treated with COMPOUND A.

NZM mice treated with COMPOUND A exhibited significantly reduced bone resorption as measured using a biomarker of osteoclast activity (i.e., c-telopeptide collagen type I cross-linker; CTx) (Bouzid, Bahlous et al.). COMPOUND A reduced the levels of serum CTx in treated NZM mice (46.7% decrease for 100 mg/kg and 37.8% decrease for 55 mg/kg vs. vehicle; $p<0.01$) (FIG. 34).

This data is important because it suggests that COMPOUND A may impact the activity of osteoclasts and/or impact cytokines involved in bone remodeling during chronic inflammatory diseases such as SLE. The ability of COMPOUND A to reduce osteoclast activity is important because osteoclast activity is enhanced during lupus, which causes bone demineralization and general loss of bone mass, leading to increased fractures, injuries and the need for joint replacements. (Kamen and Alele) The standard of care for lupus treatment, glucocorticoids such as dexamethasone, methylprednisolone and prednisone, can exacerbate this problem and further lead to bone loss via the imbalance of osteoclast over osteoblast cellular activity (Cunningham 2007). Consequently, lupus patients with bone demineralization are often treated with bisphosphonates to restore bone loss; but this treatment is toxic to the renal system and thus are counterproductive when treating lupus patients with developing lupus nephritis (Body, Diel et al. 2004). Thus the ability of COMPOUND A to treat lupus and also reduce osteoclast activity could reverse lupus-associated bone loss and may actually help repair joint damage caused by the disease.

Plasma Cells

Figure 35B:
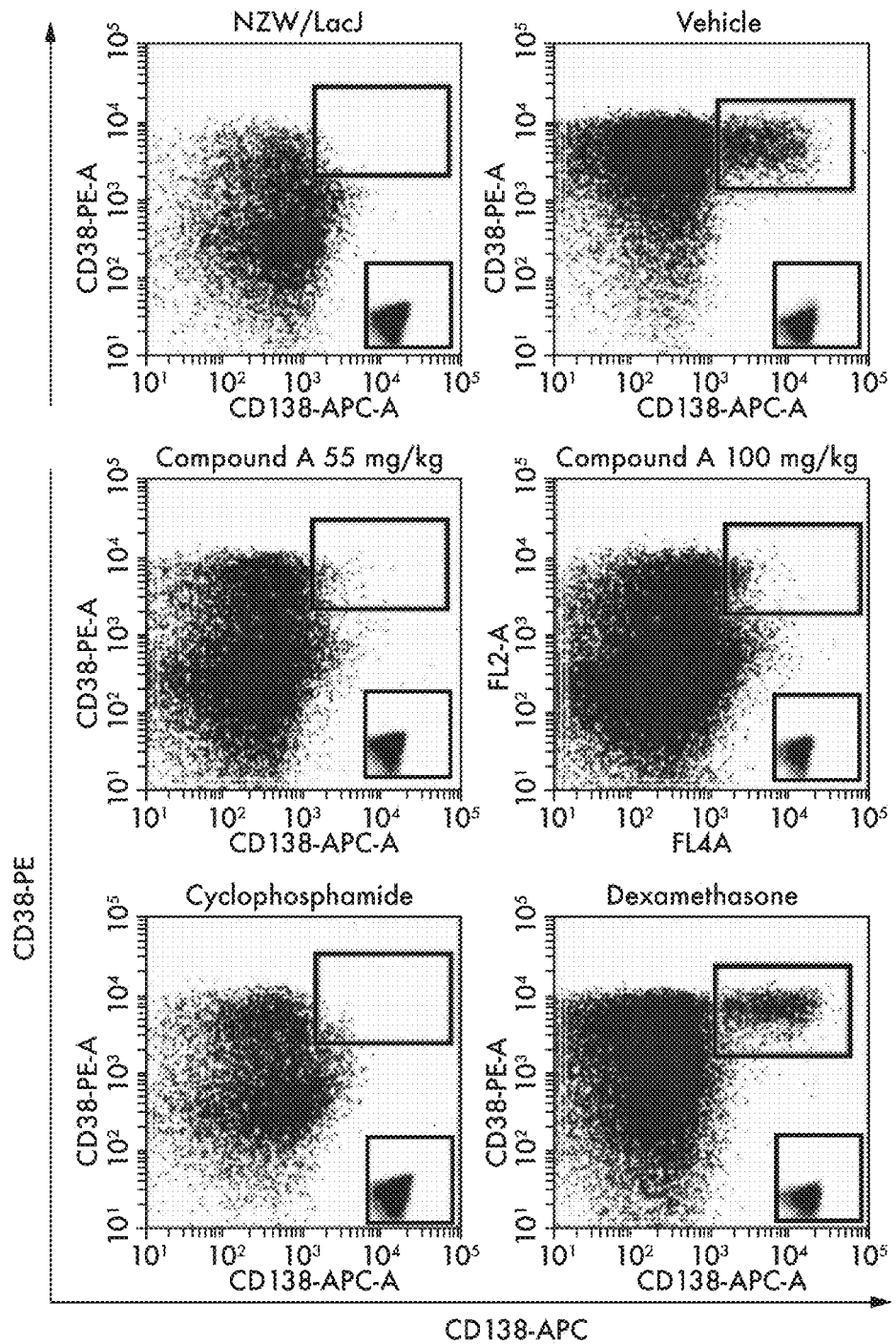
Figure 36:
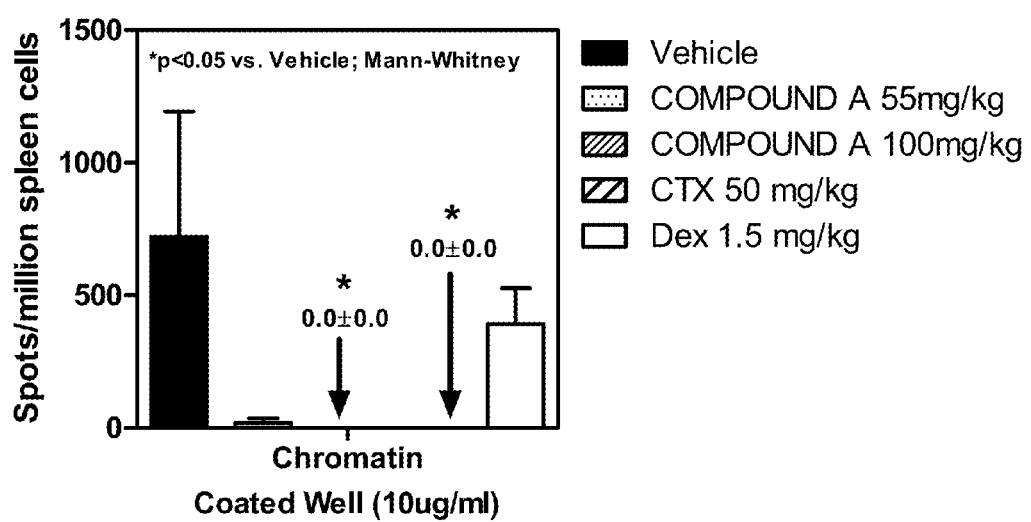
FIG. 36 depicts the frequency of ASC cells secreting anti-chromatin ANA antibody from spleens of NZM mice treated with COMPOUND A.
Figure 37:
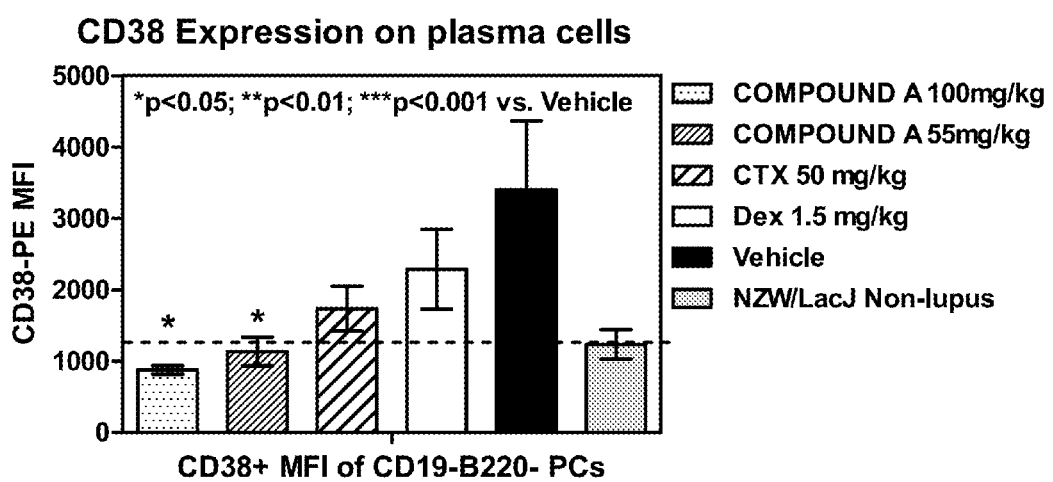
FIG. 37 depicts the average expression of marker CD38 in NZM mice treated with COMPOUND A.

NZM mice treated with COMPOUND A exhibited a reduction in spleen plasma cells at both the 100 mg/kg and 55 mg/kg doses as compared to vehicle (52.9% and 57.6% decrease; $p<0.05$), and the reduction provided by COMPOUND A was similar to the non-lupus control animals (58.4% decrease; $p<0.05$) (FIG. 35). NZM mice treated with COMPOUND A exhibited a decrease in expression of cyclic ADP ribose hydrolase, CD38, at both the 100 mg/kg and 55 mg/kg doses to the level of non-lupus control mice (74.2% and 66.6% decrease; $p<0.05$) (FIG. 37). Although both dexamethasone and cyclophosphamide also reduced the levels of spleen plasma cells, the decrease was not significant (FIG. 35). NZM mice treated with COMPOUND A exhibited reduced levels of ASCs specific for chromatin, on par with cyclophosphamide (97.4% decrease for 55 mg/kg and 100% decrease for 100 mg/kg vs. 100% decrease for CTX; $p<0.05$) (FIG. 36).

This data is important because plasma cells are responsible for the generation of autoantibodies, and long-lived plasma cells are thought to be one of the root propagators of continued lupus pathogenesis in humans (Neubert, Meister et al. 2008). Long-lived plasma cells (LL-PCs) primarily populate the bone marrow (BM), but can also be found in the spleen at sites of inflammation, and are known to be resistant to cyclophosphamide, one accepted therapy for treating lupus nephritis (Alperovich, Rama et al. 2007; Houssiau and Ginzler 2008; Lacotte, Dumortier et al. 2010). The ability of COMPOUND A to reduce the levels of long-lived plasma cells is important because these cells are difficult to kill, are usually chemo- and radio-resistant, can survive for many decades within the bone marrow architecture, and produce the majority of autoantibodies during lupus. It is also important to note that spleen plasma cell proportions did not dip below that of the non-lupus control mice but rather down to a level comparable, suggesting that blockade of JAK2 with COMPOUND A restores the normal proportions of plasma cells frequencies to that of a normal aged matched control mouse.

SUMMARY

Mouse to mouse individual changes and summary of all histopathological results can be found in Table 3. As Table 3 shows, survival correlates well with marked changes in renal score, anti-dsDNA ANA levels, and proteinuria. These results clearly demonstrate the ability of COMPOUND A to treat lupus by protecting the animals from disease progression, and even reversing the course of lupus disease.

TABLE 3

NZM Comprehensive Results

| Group | Mouse | Age (d) | A | B | C | D | E | F | G | H | I |
|---|---|---|---|---|---|---|---|---|---|---|---|
| Parental control | NZW/LacJ-1 | 310 | 54.1 | − | − | − | − | − | − | − | 1.51 |
| | NZW/LacJ-2 | 310 | 125.0 | − | − | − | − | − | − | − | 1.61 |
| | NZW/LacJ-3 | 310 | 27.8 | − | − | − | − | − | − | − | 1.76 |
| | NZW/LacJ-4 | 310 | 65.9 | − | − | − | − | − | − | − | 1.00 |
| MEAN ± SD | | 310 ± 0.0 | 68.2 ± 41.0 | | | | | | | | 1.47 ± 0.32 |
| Vehicle | 9A1 | 212 | ND | ND | ND | ND | ND | ND | ND | ND | 3.58 |
| | 9A2 | 240 | 51.4 | ++ | + | − | − | − | − | + | 8.64 |
| | 9A3 | 310 | 32.0 | ++ | + | +++ | +++ | +++ | +++ | + | 1.64 |
| | 9A4 | 268 | ND | +++ | + | + | − | ++ | + | − | 13.44 |
| | 9A5 | 310 | 16.7 | + | − | − | − | − | − | + | 0.85 |
| | 9B1 | 310 | 95.2 | ND | ND | ND | ND | ND | ND | ND | 2.04 |
| | 9B2 | 240 | 27.0 | ++ | + | ++ | + | ++ | ++ | ++ | 8.63 |
| | 9B3 | 310 | 253.2 | + | + | − | + | + | − | + | 1.17 |
| | 9B4 | 227 | ND | +++ | ++ | +++ | +++ | +++ | +++ | ++ | 12.67 |
| | 9B5 | 227 | 57.0 | +++ | ++ | ++ | ++ | + | + | + | 7.48 |
| | 9C1 | 310 | 214.8 | +++ | + | +++ | +++ | +++ | +++ | ++ | 1.30 |
| MEAN ± SD | | 269.5 ± 41.0 | 93.4 ± 90.5 | | | | | | | | 5.58 ± 4.7 |
| CMPD A 100 mpk bid | 3A1 | 310 | 13.4 | − | − | − | − | − | − | − | 0.48 |
| | 3A2 | 310 | 18.2 | − | + | − | + | + | + | − | 0.55 |
| | 3A3 | 310 | 9.6 | − | − | − | − | − | − | − | 0.70 |
| | 3A4 | 268 | 13.8 | − | − | − | − | − | − | − | 0.53 |
| | 3A5 | 268 | 11.5 | − | − | − | − | − | − | − | 0.44 |
| | 3B1 | 310 | 6.6 | + | + | − | − | + | − | + | 0.11 |
| | 3B2 | 310 | 20.5 | + | ++ | ++ | − | + | + | + | 0.00 |
| | 3B3 | 310 | 5.1 | + | − | − | − | − | − | + | 0.00 |
| | 3B4 | 310 | 26.5 | + | − | − | + | − | − | + | 0.00 |
| | 3B5 | 212 | 19.2 | ND | ND | ND | ND | ND | ND | ND | 10.39 |
| MEAN ± SD | | 291.8 ± 33.0 | 14.4 ± 6.6\*\* | | | | | | | | 1.32 ± 3.1\*\* |
| CMPD A 55 mpk bid | 4A1 | 310 | 20.6 | + | − | − | − | + | − | − | 0.41 |
| | 4A2 | 212 | 39.4 | ND | ND | ND | ND | ND | ND | ND | 0.41 |
| | 4A3 | 310 | 9.4 | + | + | − | − | − | − | − | 0.50 |
| | 4A4 | 310 | 12.6 | + | + | − | − | − | − | − | 0.74 |
| | 4A5 | 310 | 12.7 | − | − | − | − | − | − | − | 0.48 |
| | 4B1 | 310 | 7.5 | − | − | − | − | − | − | − | 0.52 |
| | 4B2 | 310 | 15.2 | − | − | − | − | − | − | − | 1.11 |
| | 4B3 | 310 | 16.7 | − | − | − | − | − | − | − | 0.37 |
| | 4B4 | 310 | 19.3 | − | − | − | − | − | − | + | 0.61 |
| | 4B5 | 310 | 10.8 | − | − | − | − | − | − | − | 0.48 |
| MEAN ± SD | | 300.2 ± 30.9 | 16.4 ± 9.0\*\* | | | | | | | | 0.56 ± 0.22\*\*\* |
| CTX 50 mpk 1 × wk | 7A1 | 227 | 13.4 | ++ | ++ | +++ | + | ++++ | +++ | + | 11.09 |
| | 7A2 | 310 | 6.9 | + | − | − | − | − | − | − | 0.86 |
| | 7A3 | 310 | 22.2 | + | + | ++ | − | + | − | − | 1.44 |
| | 7A4 | 310 | 13.2 | ++ | + | ++ | +++ | ++ | + | − | 0.76 |
| | 7A5 | 310 | 40.3 | + | − | ++ | − | − | + | − | 1.30 |
| | 7B1 | 310 | 9.6 | + | ++ | + | − | − | − | + | 0.71 |
| | 7B2 | 212 | 65.1 | ND | ND | ND | ND | ND | ND | ND | 8.84 |
| | 7B3 | 310 | 52.4 | + | + | − | − | + | − | − | 0.96 |
| | 7B4 | 240 | 24.3 | − | − | + | + | − | − | − | 0.58 |
| | 7B5 | 310 | 61.9 | − | − | − | − | − | − | + | 1.50 |
| MEAN ± SD | | 284.9 ± 40.9 | 30.9 ± 22.2 | | | | | | | | 2.8 ± 3.8 |
| Dex 1.5 mpk 3 × wk | 8A1 | 291 | 27.2 | ++ | ++ | +++ | ++ | +++ | +++ | + | 8.43 |
| | 8A2 | 212 | 18.9 | | | | | | | | 10.19 |
| | 8A3 | 291 | 20.0 | ++ | ++ | +++ | ++ | +++ | ++ | + | 11.02 |
| | 8A4 | 240 | 79.5 | ND | ND | ND | ND | ND | ND | ND | 8.47 |
| | 8A5 | 268 | 167.5 | + | + | − | − | − | − | − | 0.35 |
| | 8B1 | 240 | ND | ND | ND | ND | ND | ND | ND | ND | 10.19 |

TABLE 3-continued

NZM Comprehensive Results

| Group | Mouse | Age (d) | A | B | C | D | E | F | G | H | I |
|---|---|---|---|---|---|---|---|---|---|---|---|
| | 8B2 | 212 | 27.8 | ++ | ++ | +++ | ++ | +++ | ++ | + | 7.16 |
| | 8B3 | 310 | 16.2 | + | + | ++ | − | − | − | + | 0.55 |
| | 8B4 | 310 | 10.9 | +++ | +++ | ++ | +++ | +++ | ++ | +++ | 12.36 |
| | 8B5 | 240 | 17.1 | +++ | +++ | ++++ | +++ | +++ | +++ | +++ | 9.89 |
| MEAN ± | | 261.4 ± | 42.7 ± | | | | | | | | 7.86 ± |
| SD | | 37.6 | 51.0 | | | | | | | | 4.1 |

A: Anti-dsDNA IgG,
B: Glomerular Cellularity,
C: Glomerular Necrosis,
D: Glomerular Sclerosis,
E: Interstitial Infiltration,
F: Tubular Atrophy,
G: Interstitial Fibrosis,
H: Vasculitis,
I: Proteinuria
*p < 0.05,
**p < 0.01,
***p < 0.001 vs. Vehicle, two-tailed Mann-Whitney t-test
Proteinura "0.00" = BQL, x > 1 mg/mL in bold
Scores = '−' no disease (1), '+' mild (2), '++' moderate (3), '+++' high (4), '++++' severe disease (5)

Example 3

Figure 42A:
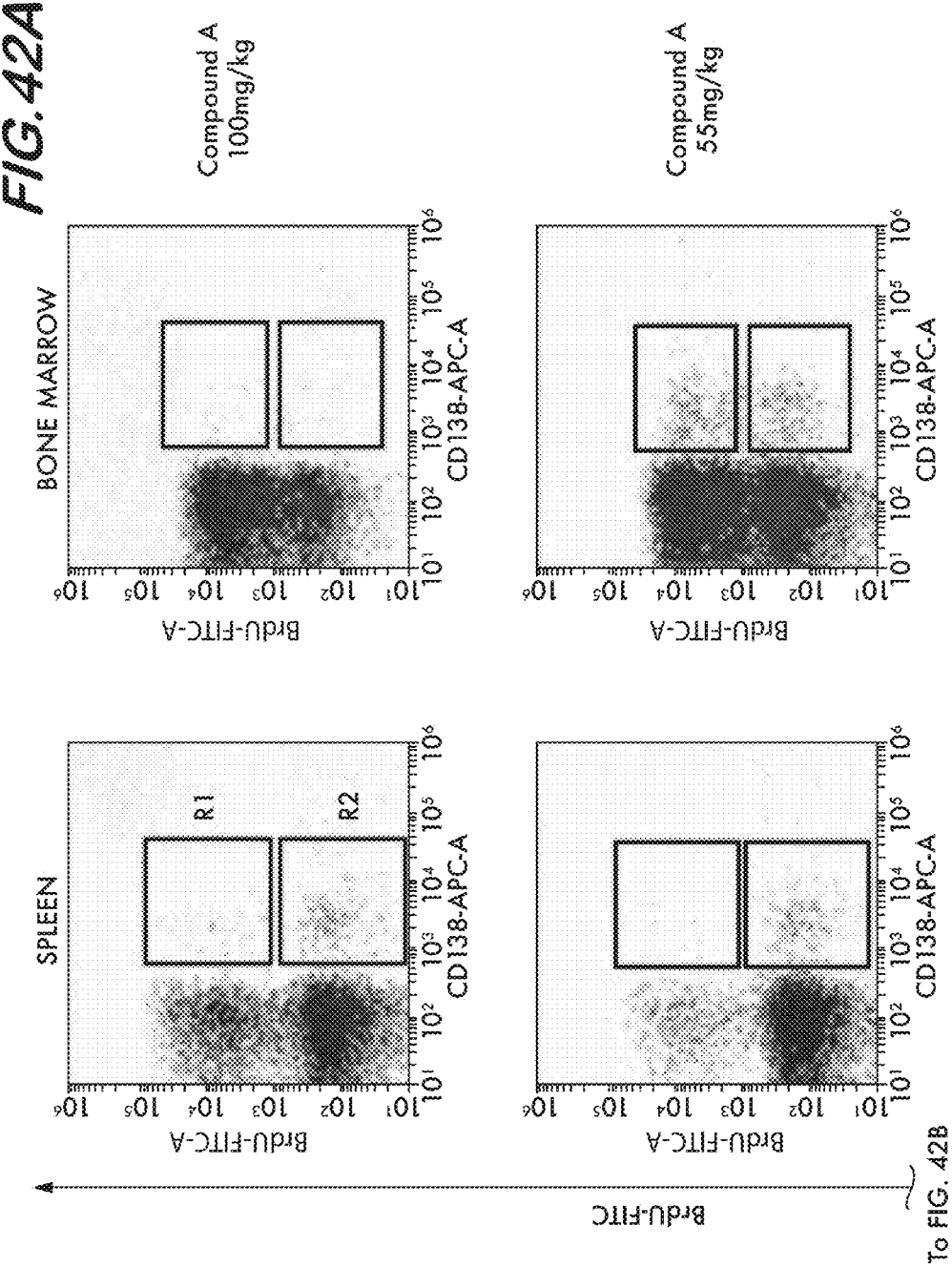

COMPOUND A Reduces the Frequency of Pathogenic, Radio/Chemo-Resistant, Lupus-Promoting, Bone Marrow Long-Lived Plasma Cells Fifteen week old, lupus-prone, NZM mice were administered 100, 55, or 30 mg/kg of COMPOUND A orally, b.i.d., standard of care reference agent cyclophosphamide at 50 mg/kg, once a week, i.p. in saline, or vehicle (PEG400), orally, b.i.d., for a total of two weeks. Twenty-four hours before the end of the study each mouse was injected i.p. with 2 mg of thymidine analog, bromodeoxyuridine (BrdU). BrdU (Cat#550891) and an anti-BrdU-FITC staining kit (Cat#559619) were obtained from BD Biosciences (Franklin Lakes, N.J.). Twenty-four hours after BrdU injection spleen and bone marrow were individually processed to isolate leukocytes for flow staining. Cells were surface stained with anti-CD19-Cyc, anti-CD38-PE and anti-CD138-APC (all obtained from eBioscience in San Diego, Calif.) as well as anti-BrdU-FITC (from the BrdU kit). Analysis included gating on live SSC/FSC populations, CD19-negative, CD38-positive and gating on CD138-positive, BrdU-negative (non-cycling, long-lived plasma cells, region R2) or BrdU-positive (cycling, short-lived plasma cells, region R1) as shown in FIG. 42. All samples were analyzed using an Accuri C6 Flow Cytometer. Complete media (R10) was used for all experiments involving the ex vivo culture of splenocytes for all Elispot experiments. Complete media consisted of RPMI1640 (Cellgro, Manassas, Va.), plus 1% Pen-Strep (Cellgro, Manassas, Va.), 1% L-Gln (Cellgro, Manassas, Va.), 1% NEAA (Cellgro, Manassas, Va.), β-ME (Cellgro, Manassas, Va.), plus 10% FBS (Cellgro, Manassas, Va.).

Figure 38:
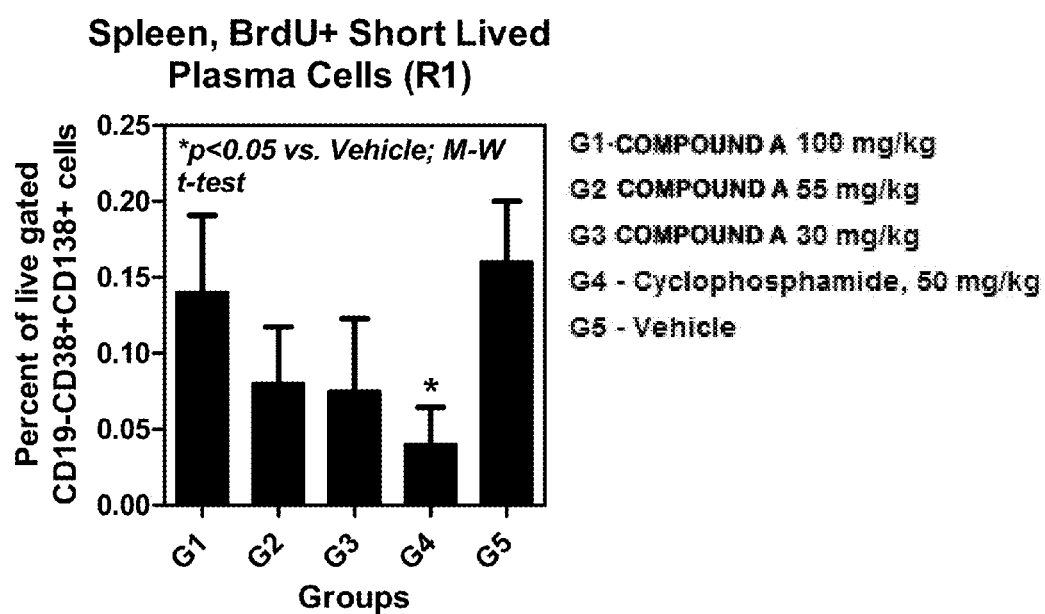
FIG. 38 depicts the percent of live spleen short lived plasma cells in NZM mice treated with COMPOUND A.
Figure 40:
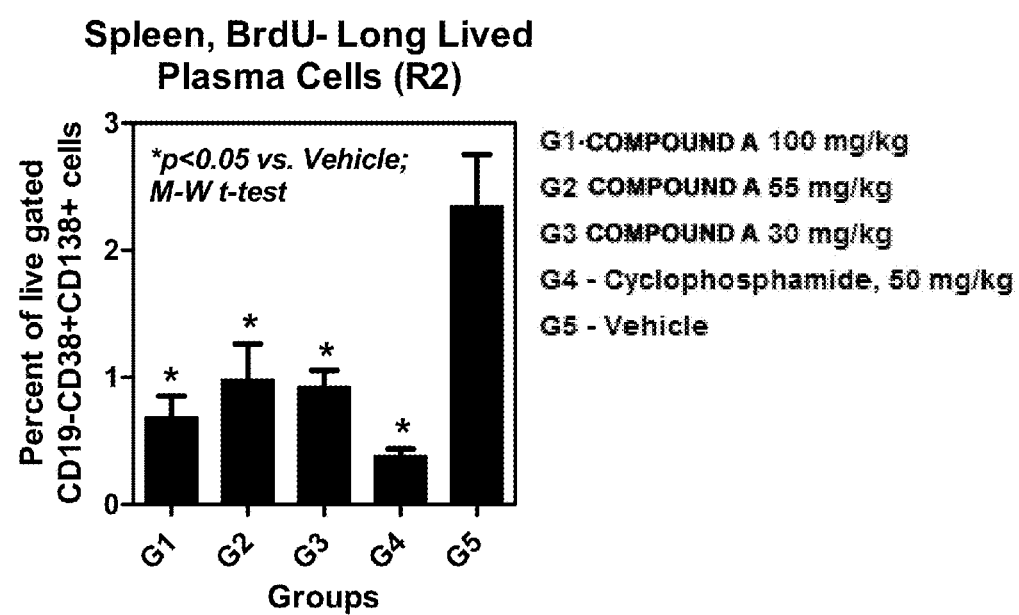
FIG. 40 depicts the percent of live spleen long lived plasma cells in NZM mice treated with COMPOUND A.
Figure 41:
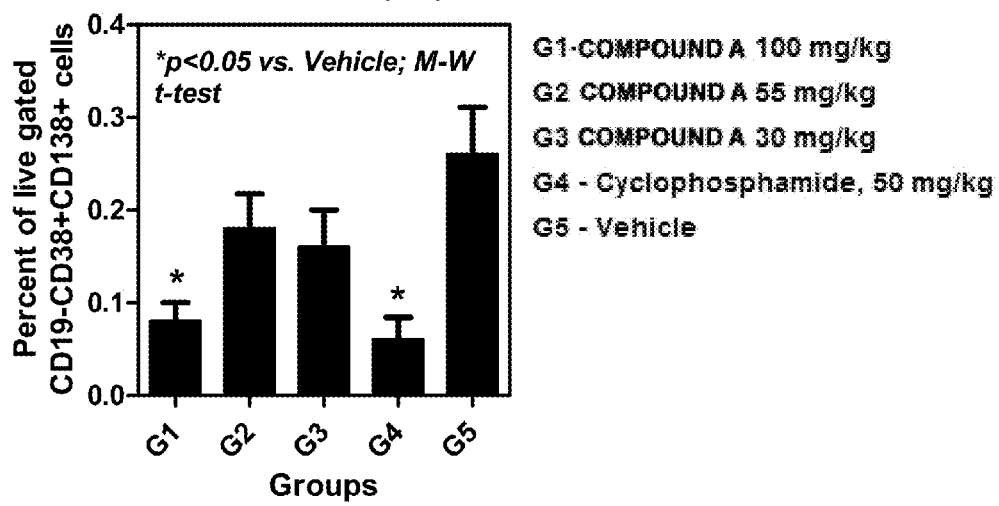
FIG. 41 depicts the percent of live bone marrow long lived plasma cells in NZM mice treated with COMPOUND A.

The Figures depict spleen short-lived plasma cells (FIG. 38), bone marrow isolated short-lived plasma cells (FIG. 39), spleen long-lived plasma cells (FIG. 40), and bone marrow isolated long-lived plasma cells (FIG. 41). Also depicted are representative dot plots providing gating examples and short-lived plasma cells, R1, and long-lived plasma cells, R2, gates (FIG. 42). Graphs show mean±SEM, statistical test included two-tailed, Mann-Whitney t-test, *p<0.05 was considered significant. All events shown were originally size gated on live cells, graphs show CD19-negative, CD38/CD138-double positive populations that had either incorporated BrdU (cycling, thus short-lived plasma cells, see region R1) or not incorporated BrdU (non-cycling, thus long-lived plasma cells, see region R2).

Figure 39:
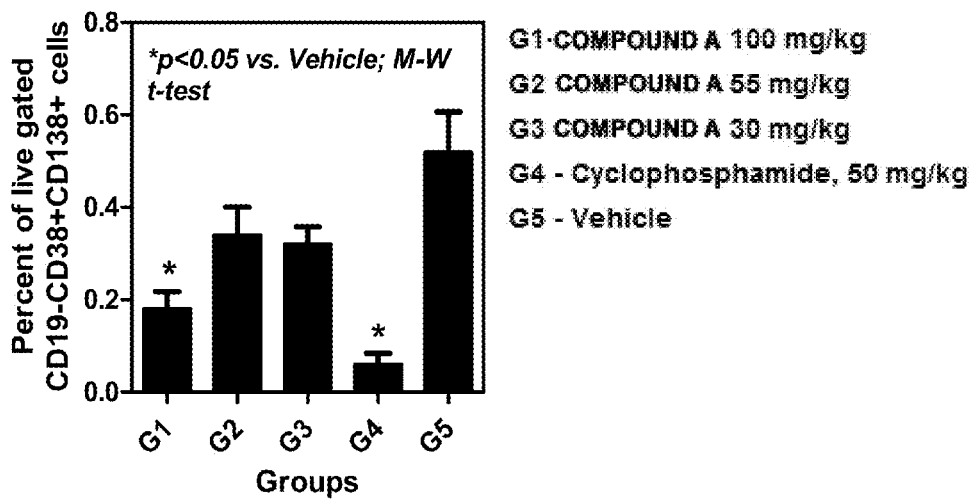
FIG. 39 depicts the percent of live bone marrow short lived plasma cells in NZM mice treated with COMPOUND A.

COMPOUND A reduced long-lived, usually radio- and chemo-resistant, plasma cells from NZM lupus-prone mice. As shown in FIGS. 38-42 both cycling (short-lived, region R1) and non-cycling (long-lived, region R2) CD138+ plasma cells decrease upon treatment with COMPOUND A. The 100 mg/kg dose of COMPOUND A impacted both short and long lived plasma cells in the bone marrow (FIGS. 39 and 41). All three doses impacted long lived plasma cells in the spleen (FIG. 40). Targeting long-lived plasma cells is important because these cells are difficult to kill, are usually chemo- and radio-resistant, can survive for many decades within the bone marrow architecture and produce the majority of autoantibodies during SLE.

PREFERRED EMBODIMENTS

Preferred embodiments of the present invention include:

Embodiment 1

A method for treating lupus in a subject, comprising the step of administering to the subject COMPOUND A.

Embodiment 2

A method for treating lupus in a subject, comprising the step of administering to the subject an effective amount of COMPOUND A.

Embodiment 3

Use of COMPOUND A in the manufacture of a medicament for treating lupus in a subject.

Embodiment 4

COMPOUND A for use in treating lupus in a subject.

Embodiment 5

The method, use, or compound of any of Embodiments 1 to 4, wherein the COMPOUND A is administered orally.

Embodiment 6

The method, use, or compound of any of Embodiments 1 to 5, wherein the COMPOUND A is administered at a dose of about 0.01 mg/kg to about 1,000 mg/kg.

Embodiment 7

The method, use, or compound of any of Embodiments 1 to 5, wherein the COMOPUND A is administered at a dose of about 1 mg/kg to about 500 mg/kg.

Embodiment 8

The method, use, or compound of any of Embodiments 1 to 5, wherein the COMPOUND A is administered at a dose of about 10 mg/kg to about 200 mg/kg.

Embodiment 9

The method, use, or compound of any of Embodiments 1 to 5, wherein the COMPOUND A is administered at a dose of about 25 mg/kg to about 150 mg/kg.

Embodiment 10

The method, use, or compound of any of Embodiments 1 to 5, wherein the COMPOUND A is administered at a dose of about 50 mg/kg to about 100 mg/kg.

Embodiment 11

The method, use, or compound of any of Embodiments 1 to 5, wherein the COMPOUND A is administered at a dose of about 55 mg/kg to about 100 mg/kg.

Embodiment 12

The method, use, or compound of any of Embodiments 1 to 5, wherein the COMPOUND A is administered at a dose of about 1 mg/kg.

Embodiment 13

The method, use, or compound of any of Embodiments 1 to 5, wherein the COMPOUND A is administered at a dose of about 5 mg/kg.

Embodiment 14

The method, use, or compound of any of Embodiments 1 to 5, wherein the COMPOUND A is administered at a dose of about 10 mg/kg.

Embodiment 15

The method, use, or compound of any of Embodiments 1 to 5, wherein the COMPOUND A is administered at a dose of about 50 mg/kg.

Embodiment 16

The method, use, or compound of any of Embodiments 1 to 5, wherein the COMPOUND A is administered at a dose of about 100 mg/kg.

Embodiment 17

The method, use, or compound of any of Embodiments 1 to 5, wherein the COMPOUND A is administered at a dose of about 0.1 mg to about 1 g.

Embodiment 18

The method, use, or compound of any of Embodiments 1 to 5, wherein the COMPOUND A is administered at a dose of about 0.5 mg to about 500 mg.

Embodiment 19

The method, use, or compound of any of Embodiments 1 to 5, wherein the COMPOUND A is administered at a dose of about 1 mg to about 100 mg.

Embodiment 20

The method, use, or compound of any of Embodiments 1 to 5, wherein the COMPOUND A is administered at a dose of about 5 mg to about 50 mg.

Embodiment 21

The method, use, or compound of any of Embodiments 1 to 5, wherein the COMPOUND A is administered at a dose of about 5 mg to about 30 mg.

Embodiment 22

The method, use, or compound of any of Embodiments 1 to 5, wherein the COMPOUND A is administered at a dose of about 5 mg to about 20 mg.

Embodiment 23

The method, use, or compound of any of Embodiments 1 to 5, wherein the COMPOUND A is administered at a dose of about 1 mg.

Embodiment 24

The method, use, or compound of any of Embodiments 1 to 5, wherein the COMPOUND A is administered at a dose of about 5 mg.

Embodiment 25

The method, use, or compound of any of Embodiments 1 to 5, wherein the COMPOUND A is administered at a dose of about 10 mg.

Embodiment 26

The method, use, or compound of any of Embodiments 1 to 5, wherein the COMPOUND A is administered at a dose of about 20 mg.

Embodiment 27

The method, use, or compound of any of Embodiments 1 to 5, wherein the COMPOUND A is administered at a dose of about 30 mg.

Embodiment 28

The method, use, or compound of any of Embodiments 1 to 5, wherein the COMPOUND A is administered at a dose of about 40 mg.

Embodiment 29

The method, use, or compound of any of Embodiments 1 to 5, wherein the COMPOUND A is administered at a dose of about 50 mg.

Embodiment 30

The method, use, or compound of any of Embodiments 1 to 5, wherein the COMPOUND A is administered at a dose of about 100 mg.

Embodiment 31

The method, use, or compound of any of Embodiments 1 to 5, wherein the COMPOUND A is administered at a dose of about 200 mg.

Embodiment 32

The method, use, or compound of any of Embodiments 1 to 31, wherein the subject experiences a decrease in lymphomegaly during treatment.

Embodiment 33

The method, use, or compound of any of Embodiments 1 to 32, wherein the subject experiences a decrease in splenomegaly during treatment.

Embodiment 34

The method, use, or compound of any of Embodiments 1 to 33, wherein the subject experiences a decrease in spleen leucocyte counts during treatment.

Embodiment 35

The method, use, or compound of any of Embodiments 1 to 34, wherein the subject experiences a decrease in serum IL-12 during treatment.

Embodiment 36

The method, use, or compound of any of Embodiments 1 to 35, wherein the subject experiences an increase in serum C3 during treatment.

Embodiment 37

The method, use, or compound of any of Embodiments 1 to 36, wherein the subject experiences a decrease in kidney glomerular cellularity during treatment.

Embodiment 38

The method, use, or compound of any of Embodiments 1 to 37, wherein the subject experiences a decrease in kidney interstitial infiltration during treatment.

Embodiment 39

The method, use, or compound of any of Embodiments 1 to 38, wherein the subject experiences a decrease in kidney pSTAT3 during treatment.

Embodiment 40

The method, use, or compound of any of Embodiments 1 to 39, wherein the subject experiences a decrease in spleen plasma cells during treatment.

Embodiment 41

The method, use, or compound of any of Embodiments 1 to 40, wherein the subject experiences a decrease in serum antinuclear antibodies during treatment.

Embodiment 42

The method, use, or compound of any of Embodiments 1 to 41, wherein the subject experiences a decrease in serum anti-dsDNA antinuclear antibodies during treatment.

Embodiment 43

The method, use, or compound of any of Embodiments 1 to 42, wherein the subject experiences a decrease in serum IFNα during treatment.

Embodiment 44

The method, use, or compound of any of Embodiments 1 to 43, wherein the subject experiences a decrease in proteinuria during treatment.

Embodiment 45

The method, use, or compound of any of Embodiments 1 to 44, wherein the subject experiences a decrease in lung infiltrates during treatment.

Embodiment 46

The method, use, or compound of any of Embodiments 1 to 45, wherein the subject experiences a decrease in serum IL-17A during treatment.

Embodiment 47

The method, use, or compound of any of Embodiments 1 to 46, wherein the subject experiences a decrease in serum IL-6 during treatment.

Embodiment 48

The method, use, or compound of any of Embodiments 1 to 47, wherein the subject experiences a decrease in serum CCL3/MIP-1α during treatment.

Embodiment 49

The method, use, or compound of any of Embodiments 1 to 48, wherein the subject experiences a decrease in serum CXCL10/IP-10 during treatment.

Embodiment 50

The method, use, or compound of any of Embodiments 1 to 49, wherein the subject experiences a decrease in serum CXCL9/MIG during treatment.

Embodiment 51

The method, use, or compound of any of Embodiments 1 to 50, wherein the subject experiences a decrease in serum IL-4 during treatment.

Embodiment 52

The method, use, or compound of any of Embodiments 1 to 51, wherein the subject experiences a decrease in serum IL-13 during treatment.

Embodiment 53

The method, use, or compound of any of Embodiments 1 to 52, wherein the subject experiences a decrease in serum TNFα during treatment.

Embodiment 54

The method, use, or compound of any of Embodiments 1 to 53, wherein the subject experiences a decrease in serum KC/IL-8 during treatment.

Embodiment 55

The method, use, or compound of any of Embodiments 1 to 54, wherein the subject experiences a decrease in serum CTx during treatment.

Embodiment 56

The method, use, or compound of any of Embodiments 1 to 55, wherein the subject is a human.

Embodiment 57

The method, use, or compound of any of Embodiments 1 to 56, wherein the COMPOUND A is administered once per day.

Embodiment 58

The method, use, or compound of any of Embodiments 1 to 56, wherein the COMPOUND A is administered twice per day.

Embodiment 59

The method, use, or compound of any of Embodiments 1 to 56, wherein the COMPOUND A is administered three times per day.

Embodiment 60

The method, use, or compound of any of Embodiments 1 to 56, wherein the COMPOUND A is administered four times per day.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

All publications referenced herein are incorporated by reference in their entireties for all purposes.

REFERENCES

Alperovich, G., I. Rama, et al. (2007). "New immunosuppresor strategies in the treatment of murine lupus nephritis." Lupus 16(1): 18-24.

Aringer, M. and J. S. Smolen (2004). "Tumour necrosis factor and other proinflammatory cytokines in systemic lupus erythematosus: a rationale for therapeutic intervention." Lupus 13(5): 344-7.

Bertsias, G. and D. T. Boumpas (2008). "Update on the management of lupus nephritis: let the treatment fit the patient." Nat Clin Pract Rheumatol 4(9): 464-72.

Body, J. J., I. Diel, et al. (2004). "Profiling the safety and tolerability of bisphosphonates." Semin Oncol 31(5 Suppl 10): 73-8.

Boumpas, D. T., R. Furie, et al. (2003). "A short course of BG9588 (anti-CD40 ligand antibody) improves serologic activity and decreases hematuria in patients with proliferative lupus glomerulonephritis." Arthritis Rheum 48(3): 719-27.

Bouzid, K., A. Bahlous, et al. "C-telopeptides of type I collagen in postmenopausal women: an experience in a Tunisian clinical laboratory." Tunis Med 88(7): 467-9.

Chevrier, S., C. Genton, et al. (2009). "CD93 is required for maintenance of antibody secretion and persistence of plasma cells in the bone marrow niche." Proc Natl Acad Sci USA 106(10): 3895-900.

Chun, H. Y., J. W. Chung, et al. (2007). "Cytokine IL-6 and IL-10 as biomarkers in systemic lupus erythematosus." J Clin Immunol 27(5): 461-6.

Coombs, J. H., B. J. Bloom, et al. (2010). "Improved pain, physical functioning and health status in patients with rheumatoid arthritis treated with CP-690,550, an orally active Janus kinase (JAK) inhibitor: results from a randomised, double-blind, placebo-controlled trial." Ann Rheum Dis 69(2): 413-6.

Cunningham, J. (2007). "Pathogenesis and prevention of bone loss in patients who have kidney disease and receive long-term immunosuppression." J Am Soc Nephrol 18(1): 223-34.

Egner, W. (2000). "The use of laboratory tests in the diagnosis of SLE." J Clin Pathol 53(6): 424-32.

Espeli, M., S. Bokers, et al. "Local Renal Autoantibody Production in Lupus Nephritis." J Am Soc Nephrol.

Fairhurst, A. M., A. E. Wandstrat, et al. (2006). "Systemic lupus erythematosus: multiple immunological phenotypes in a complex genetic disease." Adv Immunol 92: 1-69.

Fu, Q., X. Chen, et al. (2008). "Association of elevated transcript levels of interferon-inducible chemokines with disease activity and organ damage in systemic lupus erythematosus patients." Arthritis Res Ther 10(5): R112.

Houssiau, F. A. and E. M. Ginzler (2008). "Current treatment of lupus nephritis." Lupus 17(5): 426-30.

Kamen, D. L. and J. D. Alele "Skeletal manifestations of systemic autoimmune diseases." Curr Opin Endocrinol Diabetes Obes 17(6): 540-5.

Kiss, E., G. Lakos, et al. (2009). "Anti-nuscleosome antibody, a reliable indicator for lupus nephritis." *Autoimmunity* 42(5): 393-8.

Lacotte, S., H. Dumortier, et al. (2010). "Identification of new pathogenic players in lupus: autoantibody-secreting cells are present in nephritic kidneys of (NZBxNZW)F1 mice." *J Immunol* 184(7): 3937-45.

Meister, S., U. Schubert, et al. (2007). "Extensive immunoglobulin production sensitizes myeloma cells for proteasome inhibition." *Cancer Res* 67(4): 1783-92.

Morel, L. "Genetics of SLE: evidence from mouse models." *Nat Rev Rheumatol* 6(6): 348-57.

Morimoto, S., Y. Tokano, et al. (2001). "The increased interleukin-13 in patients with systemic lupus erythematosus: relations to other Th1-, Th2-related cytokines and clinical findings." *Autoimmunity* 34(1): 19-25.

Muller, S., J. Dieker, et al. (2008). "Pathogenic anti-nucleosome antibodies." *Lupus* 17(5): 431-6.

Neubert, K., S. Meister, et al. (2008). "The proteasome inhibitor bortezomib depletes plasma cells and protects mice with lupus-like disease from nephritis." *Nat Med* 14(7): 748-55.

Niewold, T. B., J. Hua, et al. (2007). "High serum IFN-alpha activity is a heritable risk factor for systemic lupus erythematosus." *Genes Immun* 8(6): 492-502.

Obeng, E. A., L. M. Carlson, et al. (2006). "Proteasome inhibitors induce a terminal unfolded protein response in multiple myeloma cells." *Blood* 107(12): 4907-16.

Sanz, I. and F. E. Lee (2010). "B cells as therapeutic targets in SLE." *Nat Rev Rheumatol* 6(6): 326-37.

Smith, D. L., X. Dong, et al. (2007). "A female preponderance for chemically induced lupus in SJL/J mice." *Clin Immunol* 122(1): 101-7.

Smith-Bouvier, D. L., A. A. Divekar, et al. (2008). "A role for sex chromosome complement in the female bias in autoimmune disease." *J Exp Med* 205(5): 1099-108.

Sozzani, S., D. Bosisio, et al. "Type I interferons in systemic autoimmunity." *Autoimmunity* 43(3): 196-203.

Tucci, M., L. Lombardi, et al. (2008). "Overexpression of interleukin-12 and T helper 1 predominance in lupus nephritis." *Clin Exp Immunol* 154(2): 247-54.

What is claimed:

1. A method for treating lupus in a subject, comprising the step of administering to the subject a therapeutically effective amount of COMPOUND A

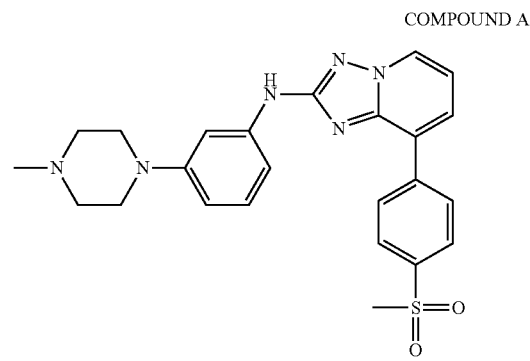 [SMILES: CN1CCN(c2cccc(Nc3nc4c(-c5ccc(S(C)(=O)=O)cc5)cccn4n3)c2)CC1]

COMPOUND A or a pharmaceutically acceptable salt thereof.

2. The method of claim 1, wherein the subject is a human.

3. The method of claim 2, wherein the COMPOUND A is administered orally.

4. The method of claim 1, wherein the COMPOUND A is administered once per day.

5. The method of claim 1, wherein the COMPOUND A is administered twice per day.

6. The method of claim 1, wherein the COMPOUND A is administered at a dose in the range of about 1 mg/kg to about 100 mg/kg.

7. The method of claim 1, wherein the COMPOUND A is administered at a dose of about 50 mg/kg to about 100 mg/kg.

8. The method of claim 1, wherein the COMPOUND A is administered at a dose of about 50 mg/kg.

9. The method of claim 1, wherein the COMPOUND A is administered at a dose of about 1 mg to about 1 g.

10. The method of claim 1, wherein the COMPOUND A is administered at a dose of about 5 mg to about 100 mg.

11. The method of claim 1, wherein the COMPOUND A is administered at a dose of about 5 mg to about 30 mg.

12. The method of claim 1, wherein the subject experiences a decrease in serum IL-12 during treatment.

13. The method of claim 1, wherein the subject experiences a decrease in kidney pSTAT3 during treatment.

14. The method of claim 1, wherein the subject experiences a decrease in spleen plasma cells during treatment.

15. The method of claim 1, wherein the subject experiences a decrease in serum antinuclear antibodies during treatment.

16. The method of claim 1, wherein the subject experiences a decrease in serum IFNα during treatment.

17. The method of claim 1, wherein the subject experiences a decrease in proteinuria during treatment.

* * * * *